(12) United States Patent
Wang et al.

(10) Patent No.: US 10,323,249 B2
(45) Date of Patent: *Jun. 18, 2019

(54) GOLD OPTIMIZED CAR T-CELLS

(71) Applicant: Chimera Bioengineering, Inc., Menlo Park, CA (US)

(72) Inventors: Benjamin Wang, Menko Park, CA (US); Gusti Zeiner, Pacifica, CA (US)

(73) Assignee: Chimera Bioengineering, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/151,138

(22) Filed: Oct. 3, 2018

(65) Prior Publication Data

US 2019/0024095 A1    Jan. 24, 2019

Related U.S. Application Data

(63) Continuation of application No. 15/692,440, filed on Aug. 31, 2017.

(60) Provisional application No. 62/382,565, filed on Sep. 1, 2016, provisional application No. 62/466,060, filed on Mar. 2, 2017, provisional application No. 62/533,858, filed on Jul. 18, 2017.

(51) Int. Cl.
| | |
|---|---|
| *C12N 15/63* | (2006.01) |
| *C12N 9/02* | (2006.01) |
| *C12N 9/96* | (2006.01) |
| *C12Q 1/6897* | (2018.01) |
| *C12Q 1/68* | (2018.01) |

(52) U.S. Cl.
CPC ......... *C12N 15/635* (2013.01); *C12N 9/0008* (2013.01); *C12N 9/96* (2013.01); *C12N 15/63* (2013.01); *C12Q 1/6897* (2013.01); *C12Y 102/01012* (2013.01)

(58) Field of Classification Search
CPC ......... C12N 9/0008; C12N 9/96; C12N 15/63
See application file for complete search history.

(56) References Cited

U.S. PATENT DOCUMENTS

| | | | |
|---|---|---|---|
| 2009/0048191 A1* | 2/2009 | Rakoczy | C12N 15/11 514/44 R |
| 2010/0316609 A1 | 12/2010 | Dewhurst et al. | |
| 2011/0003385 A1 | 1/2011 | Crabtree et al. | |
| 2014/0120622 A1 | 5/2014 | Gregory et al. | |
| 2014/0242701 A1 | 8/2014 | Shiku et al. | |
| 2014/0271583 A1 | 9/2014 | Allen-Hoffmann et al. | |
| 2014/0286987 A1 | 9/2014 | Spencer et al. | |
| 2014/0349402 A1 | 11/2014 | Cooper et al. | |
| 2018/0057822 A1* | 3/2018 | Wang | C12N 9/0008 |

FOREIGN PATENT DOCUMENTS

| | | |
|---|---|---|
| WO | WO 2015140268 | 9/2015 |
| WO | WO 2015142675 | 9/2015 |
| WO | WO 2015193406 | 12/2015 |
| WO | WO 2016028896 | 2/2016 |

OTHER PUBLICATIONS

Palmer et al.; Glucose metabolism regulatesT cell activation differentiation, and functions; Frontiers in Immunology; vol. 6, article 1, pp. 1-6, published Jan. 22, 2015 (Year: 2015).*
Christopherson et al.; Classification of AML Using a Monoclonal Antibody Microarray; pp. 241-251; (2006); In: Iland H., Hertzberg M., Marlton P. (eds) Myeloid Leukemia. Methods in Molecular Medicine™, vol. 125. Humana Press (Year: 2006).*
Iwamoto et al., A general chemical method to regulate protein stability in the mammalian nervous system, 2010, Chem & Biol vol. 17, pp. 981-988.
Rakhit et al, Evaluation of FKBP and DHFR based destabilizing domains in *Saccharomyces cerivisiae*, 2011, Bioorg & Med Chem Lett vol. 21, pp. 4965-4968.
Jena et al., Redirecting T-cell specificity by introducing a tumor-specific chimeric antigen receptor, 2010, Blood vol. 116, pp. 1035-1044.
Nielsen et al., Split-receptors in the tachykinin neurokinin-1 system, 1998, Eur. J. Biochem. vol. 251, pp. 217-226.
Adusumilli et al., Regional Delivery of Mesothelin-Targeted CAR T-cell Therapy Generates Potent . . . Tumor Immunity, Nov. 2014, Sci. Transl. Med. 6:261ra151.
Aranda et al., Adoptive Cell Transfer for Anticancer Immunotherapy, Apr. 2015, OncoImmunol. 3:5, e28344.
Auslander, et al., From Gene Switches to Mammalian Designer Cells: Present and Future Prospects, Mar. 2013, Trends Biotechnol. 31:155-168.
Baker et al., Structural and Dynamic Control of T-cell Receptor Specificity, Cross-Reactivity, and Binding Mechanism, 2012, Immunol. Rev. 250:10-31.
Beilstein, et al., Conditional Control of Mammalian Gene Expression by Tetracycline-Dependent Hammerhead Ribozymes, Sep. 2014, Synth. Biol. 4:526-534.
Berens, et al., RNA Aptamers as Genetic Control Devices: The Potential of Riboswitches as Synthetic Elements for Regulating Gene Expression, 2015, Biotechnol. 10:246-257.

(Continued)

*Primary Examiner* — Antonio Galisteo Gonzalez
(74) *Attorney, Agent, or Firm* — HelixIP LLP

(57) ABSTRACT

Control Devices are disclosed including RNA destabilizing elements (RDE), RNA control devices, and destabilizing elements (DE) combined with Chimeric Antigen Receptors (CARs) or other transgenes in eukaryotic cells. Multicistronic vectors are also disclosed for use in engineering host eukaryotic cells with the CARs and transgenes under the control of the control devices. These control devices can be used to optimize expression of CARs in the eukaryotic cells so that, for example, effector function is optimized. CARs and transgene payloads can also be engineered into eukaryotic cells so that the transgene payload is expressed and delivered after stimulation of the CAR on the eukaryotic cell.

14 Claims, 18 Drawing Sheets

Specification includes a Sequence Listing.

(56) References Cited

OTHER PUBLICATIONS

Bonifant, et al., Toxicity and Management in CAR T-cell Therapy, 2016, Oncolytics 3:16011.
Bray, et al., On-Site CAR Parking, 2015, Sci. Transl. Med. 7:275ra22.
Brayer et al., Developing Strategies in the Immunotherapy of Leukemias, Jan. 2013, Cancer Control 20:49-59.
Brentjens, et al., Adoptive Therapy of Cancer with T cells Genetically Targeted to Tumor Associated Antigens Through . . . , May 2011, Am Soc Gene Cell Therap., presentation.
Brudno et al., Allogenic T Cells That Express and Anti-CD19 Chimeric Antigen Receptor Induce Remissions of B-cell . . . , 2016, Am Soc Clin Oncol 34.
Buckley et al., Update on Antigen-Specific Immunotherapy of Acute Myeloid Leukemia, 2015, Curr. Hematol. Malig. Rep. 10:65-75.
Budde et al., Combining a CD20 Chimeric Antigen Receptor and an Inducible Caspace 9 Suicide Switch to Improve the Efficacy . . . , Dec. 2013, PLoS ONE 8:e82742.
Cantelmo, et al., Inhibition of the Glycolytic Activator PFKFB3 in Endothelium Induces Tumor Vessel Normalization . . . , Dec. 2016, Cancer Cell 30:968-985.
Caruso et al., Tuning Sensitivity of CAR to EGFR Density Limits Recognition of Normal Tissue While Maintaining . . . , 2015, Cancer Res. 75:3505-3518.
Chakravarti et al., Synthetic Biology in Cell-Based Cancer Immunotherapy, 2015, Trends Biotechnol. 33:449-461.
Chang et al., Posttranscriptional Control of T Cell Effector Function by Aerobic Glycolysis, Jun. 2013, Cell 153:1239-1251.
Chang et al., Identification and Selective Expansion of Functionally Superior T cells Expressing Chimeric Antigen Receptors, 2015, J. Transl. Med. 13:161.
Cheadle et al., CAR T cells: Driving the Road from the Laboratory to the Clinic, 2013, Immunol. Rev. 257:91-106.
Chen et al., Genetic Control of Mammalian T-cell Proliferation with Synthetic RNA Regulatory Systems, 2010, Proc. Natl Acad. Sci. 107:8531-8536.
Chen et al., Efficient Gene Editing in Primary Human T cells, Nov. 2015, Trends Immunol. 36:667-669.
Cooper et al., Moving from Tinkering in the Garage to Assembly Line Production: the Manufacture of Genetically Modified T cells . . . , 2015, Cancer Gene Therap. 22:64-66.
Darcy et al., Adoptive Immnotherapy: a New Era for the Treatment of Cancer, 2015, Immunotherap. 7:469-471.
Davila et al., Efficacy and Toxicity Management of 19-28z CAR T cell Therapy in B cell Acute Lymphoblastic Leukemia, Feb. 2014, Sci Transl Med 6:224ra25.
Di Stasi et al., Inducible Apoptosis as a Safety Switch for Adoptive Cell Therepy, 2011, N. Engl. J. Med. 265:1673-83.
Dotti et al., Design and Development of Therapies Using Chimeric Antigen Receptor-Expressing T cells, Jan. 2014, Immunol. Rev. 257:107-126.
Elert et al., Calling Cells to Arms, Dec. 2013, Nature 504:S2-S3.
Elfakess et al., Unique Translation Initiation of mRNAs-Containing TISU Element, Jun. 2011, Nucl. Acids. Res. 39:7598-7609.
Ellebrecht et al., Reengineering Chimeric Antigen Receptor T cells for Targeted Therapy of Autoimmune Disease, Jul. 2016, Science 353:179-184.
Farajnia et al., Development Trends for Generation of Single-Chain Antibody Fragments, Aug. 2014, Immunopharmacol. Immunotoxicol. 36:297-308.
Federov et al., PD-1 and CTLA-4 Based Inhibitory Chimeric Antigen Receptors (iCARs) Divert Off-Target Immunotherapy . . . , Dec. 2013, Sci. Transl. Med. 5:215ra172.
Festuccia et al., Allogenic Stem Cell Transplantation in Multiple Myeloma: Immunotherapy and New Drugs, Jun. 2015, Expert Opin. Biol. Therapy 15:857-872.
Garber et al., Adoptive T-cell Therapy for Leukemia, 2014, Molc. Cell. Therap. 2:25.

Garcia-Sanz et al., Translational Control: a General Mechanism for Gene Regulation During T cell Activation, 1998, FASEB J. 12:299-306.
Ghorashian et al., CD19 Chimeric Antigen Receptor T cell Therapy for Haematological Malignancies, Mar. 2015, Brit, J. Haematol. 169:463-478.
Grada et al., TanCAR: A Novel Bispecific Chimeric Antigen Receptor for Cancer Immunotherapy, 2013, Molc. Therap. Nucl. Acids 2:e105.
Hamilton et al., Delineation of a Novel Pathway that Regulates CD154 (CD40 Ligand) Expression, 2003, Molc. Cell. Biol. 23:510-525.
Hjelm et al., Mifepristone-Inducible Transgene Expression in Neural Progenitor Cells in vitro and in vivo, 2016, Gene Therap. 23:424-437.
Horton et al., Recent Advances in Acute Myeloid Leukemia Stem Cell Biology, 2012, Haematolog. 97:966-974.
Huang et al., Driving an Improved Car for Cancer Immunotherpy, 2016, J. Clin. Invest. 126:2795-2798.
Hudecek et al., The Nonsignaling Extracellular Spacer Domain of Chimeric Antigen Receptors is Decisive for In Vivo . . . , Sep. 2014, Cancer Immunol. Res. 3:125-135.
Hurton et al., Tethered IL-15 Augments Antitumor Activity and Promotes a Stem-Cell Memory Subset in Tumor-Specific T cells, Nov. 2016, Proc. Natl Acad Sci 113:E7788-E7797.
Hussaini et al., Targeting CD123 in AML Using a T-cell Directed Dual-Affinity Re-Targeting (DART) Platform, Nov. 2015, Blood 127:122-131.
Iwamoto et al., A General Chemical Method to Regulate Protein Stability in the Mammalian Central Nervous System, 2010, Chem Biol 17:981-988.
Jensen et al., Enhancing the IQ of CAR Modified T Cells, 2015, Powerpoint Slides.
Jensen et al., Mathematical Modeling of Chimeric TCR Triggering Predicts the Magnitude of target Lysis and its Impairment by TCR . . . , 2010, J. Immunol. 184:4284-4294.
Jensen et al., Design and Implementation of Adoptive Therapy with Chimeric Antigen Receptor-Modified T cells, 2014, Immunol. Rev. 257:127-144.
Jensen, Synthetic Immunobiology Boosts the IQ of T cells, Oct. 2015, Science 350:514-515.
Jensen et al., Designing Chimeric Antigen Receptors to Effectively and Safely Target Tumors, 2015, Curr. Opin. Immunol. 33:9-15.
Johnson et al., Rational Development and Characterization of Humanized Anti-EGFR Variant III Chimeric Antigen Receptor . . . , Feb. 2015, Sci. Transl. Med. 7:275ra22.
Juillerat et al., Design of Chimeric Antigen Receptors with Intergrated Controllable Transient Functions, 2016, Sci. Rep. 6:18950.
June, Drugging the Undruggable Ras—Immunotherapy to the Rescue? 2016, N. Eng. J. Med. 375:2286-2289.
Kakarla et al., CAR T cells for Solid Tumors: Armed and Ready to Go? Mar.-Apr. 2014, Cancer J. 20:151-155.
Kalos et al., Adoptive T cell Transfer for Cancer Immunotherapy in the Era of Synthetic Biology, Jul. 2013, Immunity 39:49-60.
Kawalekar et al., Distinct Signaling of Coreceptors Regulates Specific Metabolism Pathways and Impacts Memory Development . . . , 2016, Immunity 44:380-390.
Kebriaei et al., Future of Therapy in Acute Lymphoblastic Leukemia (ALL)—Potential Role of Immune-Based Therapies, 2015, Curr. Hematol. Malig. Rep. 10:76-85.
Kebriaei et al., Phase I Trials Using Sleeping Beuaty to Generate CD19-Specific CAR T cells, 2016, J. Clin. Invest. 126:3363-3376.
Kershaw et al., Clinical Application of Genetically Modified T cells in Cancer Therapy, May 2014, Clin. Transl. Immunol. 3:e16.
Kim et al., Highly Efficient RNA-Guided Genome Editing in Human Cells Via Delivery of Purified Cas9 Ribonucleoproteins, Jun. 2014, Gen. Res. 24:1012-1019.
Kis et al., Mammalian Synthetic Biology: Emerging Medical Applications, Mar. 2015, J. R. Soc. Interface 12:20141000.
Kochenderfer et al., Chemotherapy-Refractory Diffuse Large B-cell Lymphoma and Indolent B-cell Malignancies can be Effectively . . . , Aug. 2014, J. CLin. Oncol. 33:540-549.

(56) References Cited

OTHER PUBLICATIONS

Ledford, T-cell Therapy Extends Cancer Survival to Years, Dec. 2015, Nature 516:156.
Liang et al., Engineering Biological Systems with Synthetic RNA Molecules, 2011, Molc. Cell 43:915-926.
Lynn et al., Targeting of Folate Receptor-beta on Acute Myeloid Leukemia Blasts with Chimeric Antigen Receptor-Expressing T cells, May 2015, Blood 125:3466-3476.
Lindsten et al., Regulation of Lymphokine Messenger RNA Stability by a Surface-Mediated T Cell Activation Pathway, 1989, Science 244:339-343.
Liu et al., Affinity Tuned ErbB2 or EGFR Chimeric Antigen Receptor T Cells Exhibit an Increased Therapeutic Index Against Tumors in Mice, Sep. 2015, Cancer Res. 75:3596-3607.
Long et al., 4-1BB Cotimulation Ameliorates T cell Exhaustion Induced by Tonic Signaling of Chimeric Antigen Receptors, Jun. 2015, Nat Med 21:581-590.
Marcus et al., Allogenic Chimeric Antigen Receptor-Modified Cells for Adoptive Cell Therapy of Cancer, Mar. 2014, Expert Opin Biol Therap 14:947-954.
Mardiros et al., T cells Expressing CD123-Specific Chimeric Antigen Receptors Exhibit Specific Cytolytic Effector Functions . . . , Sep. 2013, Blood 122:3138-3148.
Maude et al., Chimeric Antigen Receptor T cells for Sustained Remissions in Leukemia, Mar. 2014, N. Eng. J. Med. 371:1507-1517.
Maus et al., Antibody-Modified T cells: CARs Take the Front Seat for Hematologic Malignancies, Apr. 2014, Blood 123:2625-2635.
Mayer, Nucleic Acid Aptamers: Selection, Characterization and Application, 2016, Humana Press, Springer Science.
Morgan et al., Case Report of a Serious Adverse Event Following the Administration of T cells Transduced with a Chimeric Antigen Receptor . . . , 2010, Molc Therap 18:843-851.
Nagy et al., Glyceraldehyde-3-phosphate Dehydrogenase Selectively Binds AU-Rich RNA in the NAD+-Binding Region, 1995, J Biol Chem 270:2755-2763.
Neeson, Lewis-Y Chimeric Antigen Receptor T cells Traffic and Persist in the Bone Marrow of Patients with Lewis-Y Positive AML, undated, Powerpoint SLides.
Nelson et al., Novel Immunotherapies for Hematologic Malignancies, Jan. 2015, Immunol. Rev. 263:90-105.
Newick et al., CAR T cell Therapy for Solid Tumors, Jul. 2016, Ann. Rev. Med. 68:3.1-3.14.
Norelli et al., Clinical Pharmacology of CAR-T cells: Linking Cellular Pharmacodynamics to Pharmacokinetics and Antitumor Effects, 2016, Biochim Biophys Acta 1865:90-100.
Okoye et al., The Protein LEM Promotes CD8+ T cell Immunity Through Effects on Mitochondrial Respiration, May 2015, Science 348:995-1001.
Paszkiewicz et al., Targeted Antibody-Mediated Depletion of Murine CD19 CAR T cells Permanently Reverses B cell Aplasia, 2016, J Clin Ivest 126:4262-4272.
Perales-Puchalt et al., Follicle-Stimulating Hormone Receptor is Expressed by Most Ovarian Cancer Subtypes and is a Safe . . . , 2016, Clin. Cancer Res.
Pizzitola et al., Chimeric Antigen Receptors Against CD33/CD123 Antigens Efficiently Target Primary Acute Myeloid Leukemia Cells in vivo, Aug. 2014, Leukemia 28:1596-1605.
Poirot et al., Multiplex Genome-Edited T-cell Manufacturing Platform for "Off-the-Shelf" Adoptive T-cell Immunotherapies, 2015, Cancer Res 75:3853-3864.
Posey et al., Engineered CAR T cells Targeting the Cancer-Associated Tn-Glycoform of the Membrane Mucin MUC1 Control Adenocarcinoma, 2016, Immunity 44:1444-1454.
Qin et al., Systematic Comparison of Constitutive Promoters and the Doxycycline-Inducible Promoter, 2010, PLoS ONE 5:e10611.
Rakhit et al., Chemical Biology Strategies for Posttranslational Control of Protein Function, Sep. 2014, Chem Biol 21:1238-1252.
Reddy, Changing Landscape of Immuno-Oncology: CAR-T Therapy and PD1/PDL1 Blockade, 2016, Boston University Theses.

Renert, Novel Immunotherapeutic Approaches to the Treatment of Cancer: Drug Development and Clinical Application, 2016, Springer International Publishing.
Rodgers et al., Switch-Mediated Activation and Retargeting of CAR-T cells for B-cell Malignancies, 2016, Proc Natl Acad Sci 113:E459-E468.
Rosenberg, Cell Transfer Immunotherapy for Metastataic Solid Cancer—What Clinicians Need to Know, 2011, Nat Rev Clin Oncol 8:577-585.
Rosenberg et al., Adoptive Cell Transfer as Personalized Immunotherapy for Human Cancer, Apr. 2015, Science 348:62-68.
Roybal et al., Precision Tumor Recognition by T cells with Combinatorial Antigen-Sensing Circuits, 2016, Cell 164:770-779.
Roybal et al., Engineering T cells with Customized Therapeutic Response Programs Using Synthetic Notch Receptors, 2016, Cell 167:1-14.
Sadelain et al., Sage Harbours for the Integration of New DNA in the Human Genome, 2012, Nat. Rev. 12:51-58.
Sandberg et al., In Cancer Immunotherapy Legal Battle, It's Now Juno v. Novartis, Feb. 2014, Pharma MedTech Bus Intell. 2014900027.
Shi et al., Chimeric Antigen Receptor for Adoptive Immunotherapy of Cancer: Latest Research and Future Prospects, Sep. 2014, Molc Cancer 13:219.
Sommermeyer et al., Chimeric Antigen Receptor-Modified T cells Derived from Defined CD8+ and CD4+ Subsets Confer Superior Antitumor . . . , Feb. 2016 Leukemia 30:492-500.
Srivastava et al., Engineering CAR-T cells: Design Concepts, Aug. 2015, Trends Immunol 36:494-502.
Sun et al., The Quest for Spatio-Temporal Control of CAR T cells, Dec. 2015, Cell Res. 25:1281-1282.
Tettamanti et al., CD123 AML Targeting by Chimeric Antigen Receptors: A Novel Magic Bullet for AML Therapeutics? May 2014, Oncolimmunol 3:e28835.
Till et al., Adoptive Immunotherapy for Idolent Non-Hodgkin Lymphoma and Mantle Cell Lymphoma Using Genetically Modified . . . , 2008, Blood 112:2261-2271.
Turatti et al., Redirected Activity of Human Antitumor Chimeric Immune Receptors is Governed by Antigen and Receptor Expression Levels . . . , 2007, J Immunotherap 30:684-693.
Turtle et al., CD19 CAR-T cells of Defined CD4+:CD8+ Composition in Adult B cell ALL Patients, 2016, J Clin Ivest 126:2123-2138.
Turtle et al., Immunotherapy of Non-Hodgkin's Lymphoma with a Defined Ratio of CD8+ and CD4+ CD19-Specific Chimeric Antigen Receptor . . . , 2016, Sci Transl Med 8:355ra116.
Vanderlugt et al., Epitope Spreading in Immune-Mediated Diseases: Implications for Immunotherapy, 2002, Nat Rev 2:85-95.
Vigano et al., Functional Avidity: a Measure to Predict the Efficacy of Effector T cells? 2012, Clin Develop Immunol 2012:153863.
Wang et al., ZAP-70: An Essential Kinase in T-cell Signaling, 2010, Cold Spring Barb Perspect Biol 2:a002279.
Wang et al., One-Step Generation of Mice Carrying Mutations in Multiple Genes by CRISPR/Cas-Mediated Genome Engineering, 2013, Cell 153:910-918.
Wang et al., Manufacture of tumor- and virus-specific T lymphocytes for adoptive cell therapies, Feb. 2015, Cancer Gene Therapy 22:85-94.
Watanabe et al., Target Antigen Density Governs the Efficacy of Anti-CD20-CD28-CD3 Zeta Chimeric Antigen Receptor-Modified . . . , Dec. 2014, J Immunol 194:911-920.
Weigand et al., Tetracycline Aptamer-Controlled Regulation of Pre-mRNA Splicing in Yeast, 2007, Nucl Acids Res 35:4179-4185.
Win et al., A Modular and Extensible RNA-Based Gene-Regulatory Platform for Engineering Cellular Function, 2007, Proc Natl Acad Sci 104:14283-14288.
Win et al., Frameworks for Programming Biological Function Through RNA Parts and Devices, 2009, Chem Biol 16:298-310.
Wu et al., Remote Control of Therapeutic T cells Through a Small Molecule-Gated Chimeric Receptor, Sep. 2015, Science 350:aab4077.
Xie et al., Mammalian Designer Cells: Engineering Principles and Biomedical Applications, Jul. 2015, Biotechnol J 10:1005-1018.
Xie et al., Synthetic Biology—Application-Oriented Cell Engineering, 2016, Curr. Opin. Biotechnol. 40:139-148.

(56) References Cited

OTHER PUBLICATIONS

Ye et al., Synthetic Mammalian Gene Circuits for Biomedical Applications, 2013, Curr. Opin. Chem Biol 17:910-917.

Zhao et al., Structural Design of Engineered Costimulation Determines Tumor Rejection Kinetics and Persistence of CAR T cells, Oct. 2015, Cancer Cell 28:415-428.

Zheng et al., Protein L: A Novel Reagent for the Detection of Chimeric Antigen Receptor (CAR) Expression by Flow Cytometry, 2012, J Transl Med 10:29.

Muti, ASH Conference Review, 2014.

Zhong et al., Rational Design of Aptazyme Riboswitches for Efficient Control of Gene Expression in Mammalian Cells, Nov. 2016, eLife 5:e18858.

Auslander et al., A ligand-dependent hammerhead ribozyme switch for controlling mammalian gene expression, Molc. Biosys. vol. 6, pp. 807-814 (2010).

Win et al., A modular and estensible RNA-based gene-regulatory platform for engineering cellular function, Proc. Natl Acad. Sci. vol. 104, pp. 14283-14286 (2007).

\* cited by examiner

GOLD OPTIMIZED CAR T-CELLS

This application is continuation of U.S. application Ser. No. 15/692,440 filed Aug. 31, 2017, which claims priority to U.S. provisional application Ser. No. 62/382,565 filed Sep. 1, 2016, U.S. provisional application Ser. No. 62/466,060 filed Mar. 2, 2017, and U.S. provisional application Ser. No. 62/533,858 filed Jul. 18, 2017.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CBIO024_ST25.txt", a creation date of Aug. 28, 2017, and a size of 9 kilobytes. The Sequence Listing filed via EFS-Web is part of the specification and is incorporated in its entirety by reference herein.

BACKGROUND OF THE INVENTION

Chimeric Antigen Receptors are human engineered receptors that may direct a T-cell to attack a target recognized by the CAR. For example, CAR T cell therapy has been shown to be effective at inducing complete responses against acute lymphoblastic leukemia and other B-cell-related malignancies and has been shown to be effective at achieving and sustaining remissions for refractory/relapsed acute lymphoblastic leukemia (Maude et al., NEJM, 371:1507, 2014). However, dangerous side effects related to cytokine release syndrome (CRS), tumor lysis syndrome (TLS), B-cell aplasia and on-tumor, off-target toxicities have been seen in some patients.

There are currently two extant strategies to control CAR technology. The first is an inducible "kill switch." In this approach, one or more "suicide" genes that initiate apoptotic pathways are incorporated into the CAR construct (Budde et al. PLoS1, 2013 doi:10.1371/journal.pone.0082742). Activation of these suicide genes is initiated by the addition of AP1903 (also known as rimiducid), a lipid-permeable tachrolimus analog that initiates homodimerization of the human protein FKBP12 (Fv), to which the apoptosis-inducing proteins are translationally fused. In the ideal scenario, these kill switches endeavor to sacrifice the long-term surveillance benefit of CAR technology to safeguard against toxicity. However, in vivo, these suicide switches are not likely to realize this goal, as they are operating against powerful selection pressures for CAR T-cells that do not respond to AP1903, a situation worsened by the inimical error-prone retroviral copying associated with the insertion of stable transgenes into patient T-cells. In this scenario, non-responsive CAR T-cell clones will continue to proliferate and kill target cells in an antigen-dependent manner. Thus, kill switch technology is unlikely to provide an adequate safeguard against toxicity.

The second CAR regulatory approach is transient CAR expression, which can be achieved in several ways. In one approach, T-cells are harvested from unrelated donors, the HLA genes are deleted by genome-editing technology and CAR-encoding transgenes are inserted into the genome of these cells. Upon adoptive transfer, these CAR T-cells will be recognized by the recipient's immune system as being foreign and destroyed, thus the CAR exposure in this system is transient. In another transient CAR exposure approach, mRNA of a CAR-encoding gene is introduced into harvested patient T-cells (Beatty, G L 2014. Cancer Immunology Research 2 (2): 112-20. doi:10.1158/2326-6066.CIR-13-0170). As mRNA has a short half-life and is not replicated in the cell or stably maintained, there is no permanent alteration of the CAR-expressing T-cell, thus the CAR expression and activity will be for a short period of time. However, as with the kill-switch approach, these transient CAR exposure approaches sacrifice the surveillance benefit of CARs. Additionally, with these transient systems acute toxicity can be difficult to control.

SUMMARY OF THE INVENTION

In an aspect, the description discloses a eukaryotic cell with a CAR, T-cell receptor, or other targeting polypeptide and a transgene under the control of an RNA Destabilizing Element (RDE). The RDE may control multiple transgenes or multiple RDEs may control multiple transgenes. The multiple transgenes may be arranged serially and/or as a concatemer and/or in other arrangements. Multiple RDEs may be used to regulate a transgene, and these multiple RDEs can be organized as a concatemer, interspersed within a region of the transcript, or located in different parts of the transcript. Multiple transgenes can be regulated by an RDE or a combination of RDEs. The RDEs can be localized in the 3'-UTR, the 5'-UTR and/or an intron. In an aspect, the RDE can be engineered to increase or decrease the binding affinity of RNA binding protein(s) that interact with the RDE. Altering the affinity of the RNA binding protein can change the timing and response of transgene expression as regulated by the RNA binding protein. In an aspect, the RNA binding protein binding at the RDE is altered by the metabolic state of the cell and changing the binding affinity of the RDE for the RNA binding protein alters the response to and/or timing of transgene expression with the metabolic state of the cell. In an aspect, the RNA binding protein binding at the RDE is altered by the redox state of the cell and changing the binding affinity of the RDE for the RNA binding protein alters the response to and/or timing of transgene expression with the redox state of the cell.

In an aspect, the CAR, T-cell receptor, B-cell receptor, innate immunity receptor, or other targeting receptor or targeting polypeptide recognizes an antigen at the target site (e.g., tumor cell or other diseased tissue/cell) and this activates the cell. The transgene can be another CAR that recognizes a second antigen at the target site and activation of the cell by the first CAR, T-cell receptor or other targeting polypeptide induces the second CAR allowing the eukaryotic cell to recognize the target site by a second antigen. In an aspect, the eukaryotic cell has a first CAR that recognizes an antigen at a target site and this activates a transgene (through an RDE) that encodes a polypeptide that directly or indirectly reduces the activation state of the cell. For example, the transgene may encode a second CAR that recognizes an antigen on healthy tissue so that when the first CAR reacts with antigen at a nontarget cell, the eukaryotic cell will be de-activated by the second CAR interaction with the healthy cell antigen (that is not present or is present in reduced amounts at the target site).

In some aspects, the eukaryotic cell is an immune cell, e.g., a T-cell, a natural killer cell, a B-cell, a macrophage, a dendritic cell, or other antigen presenting cell. In these aspects, activation of the cell by the CAR or changing the metabolic state of the immune cell in other ways can induce expression of the transgene through the RDE. The RDE that controls the transgene can have microRNA binding sites and can be engineered to remove one or more of these microRNA binding sites. The RDE can be bound by the Hu Protein R (HuR). Without wishing to be bound by theory it is expected that HuR can bind to some RDEs, and act to stabilize the mRNA, leading to enhanced translation. Some RDEs can be tied to the glycolytic state of the eukaryotic cell through the enzyme glyceraldehyde 3-phosphate dehydrogenase (GAPDH), other dehydrogenases, other oxidoreductases, or other glycolytic enzymes that can bind to an RDE when the eukaryotic cell is not activated (low glycolytic activity), quiescent, or at rest. When GAPDH or the other enzymes bind to the RDE this can reduce half-life of the RNA with the RDE. In this aspect, CAR activation of the eukaryotic cell (e.g., T-lymphocyte) can induce glycolysis in the cell which reduces GAPDH binding of the RNA, increases half-life of the RNA, which produces increased expression of the transgene encoded in the RNA and controlled by the RDE. Without wishing to be bound by theory, as GAPDH vacates the RDE, HuR or other RDE binding proteins may subsequently bind either the same RDE, or a previously inaccessible RDE (sterically hindered by presence of GAPDH), further stabilizing the mRNA, increasing half-life of the mRNA, and producing further increased expression of the transgene encoded by the RNA and controlled by said RDE. Thus, CAR activation can induce expression of the transgene. In other aspects, other activation of the immune cell can cause GAPDH to engage in glycolysis and so induce expression of the transgene under the control of the RDE.

Expression from the transcript with the RDE(s) can respond to the metabolic state of the cell. For example, the RDE can be bound by metabolic or glycolytic enzymes which couples expression of the transgene to the activation state of the cell through these metabolic or glycolytic enzymes. Some metabolic or glycolytic enzymes bind to RDEs in the transcript and degrade or target for degradation the transcript. When those metabolic or glycolytic enzymes become active, the enzymes no longer bind to the RDEs, the transcripts are stable for a longer period of time, and the transcripts can be translated for this longer period of time. Cells expressing transgenes under the control of such RDEs can also be engineered to express a CAR that can alter the metabolic state of the cell at desired times resulting in expression of the transgene at the desired time. Alternatively, other stimuli can be used to alter the metabolic state of the eukaryotic cell resulting in expression of the transgene. For example, the metabolic state of the cell can be altered to cause transgene expression (or to inhibit expression) by stimuli including, for example, small molecules (e.g., PMA/ionomycin), cytokines, a TCR and costimulatory domain engagement with ligand, oxygen levels, cellular stress, temperature, or light/radiation.

GAPDH binding to the RDE can be increased by introducing into the cell a small molecule that inhibits glycolysis such as, for example, rapamycin, 2-deoxyglucose, 3-bromophyruvic acid, iodoacetate, fluoride, oxamate, ploglitazone, dichloroacetic acid, or other metabolism inhibitors such as, for example, dehydroepiandrosterone. Other small molecules can be used to reduce GAPDH binding to the RDE. Such small molecules may block the RDE binding site of GAPDH including, for example, CGP 3466B maleate or Heptelidic acid (both sold by Santa Cruz Biotechnology, Inc.), pentalenolactone, or 3-bromopyruvic acid. Other small molecules can be used to analogously inhibit other enzymes or polypeptides from binding to RDEs. Other small molecules can be used to change the redox state of GAPDH, leading to an altered affinity of GAPDH for the RDE.

In an aspect, activation of the immune cell induces expression of the transgene that can encode a payload to be delivered at the target (activation) site. The transgene can encode a payload for delivery at the site of CAR activation and/or immune cell activation. The payload can be a cytokine, an antibody, a reporter (e.g., for imaging), a receptor (such as a CAR), or other polypeptide that can have a desired effect at the target site. The payload can remain in the cell, or on the cell surface to modify the behavior of the cell. The payload can be an intracellular protein such as a kinase, phosphatase, metabolic enzyme, an epigenetic modifying enzyme, a gene editing enzyme, etc. The payload can be a gene regulatory RNA, such as microRNAs, antisense RNA, ribozymes, and the like, or guide RNAs for use with CRISPR systems. The payload can also be a membrane bound protein such as GPCR, a transporter, etc. The payload can be an imaging agent that allows a target site to be imaged (target site has a desired amount of target antigen bound by the CAR). The payload can be a checkpoint inhibitor, and the CAR and/or other binding protein (e.g., T-cell receptor, antibody or innate immunity receptor) can recognize a tumor associated antigen so the eukaryotic cell preferentially delivers the checkpoint inhibitor at a tumor. The payload can be a cytotoxic compound including, for example, a granzyme, an apoptosis inducer, a cytotoxic small molecule, or complement. In some aspects, expression of the CAR is under the control of an inducible promoter, an RNA control device, a DE, a Side-CAR, and/or an RDE. The amount of CAR on the surface of the cell can allow the eukaryotic cell to be preferentially activated at the tumor site and not at normal tissue because the tumor displays higher amounts of target antigen (e.g., the amount of CAR can be adjusted to increase avidity at the tumor site versus healthy tissue). In addition, this regulatory control of CAR expression provides another level of control to the eukaryotic cell and its delivery of payload. In an aspect, the payload can remain in the cell or on the cell surface (rather than secreted to the target), to modify the behavior of the cell.

In some aspects, the expression of CAR, DE-CAR and/or Side-CAR polypeptide is controlled, at least in part, by an RDE that interacts with a glycolytic enzyme with RDE binding activity, e.g., GAPDH. The glycolytic enzyme can bind to the RDE and reduce production of the CAR, DE-CAR, Side-CAR polypeptide, and/or other transgene product. This reduction in polypeptide production can occur because of an inhibition of translation and/or an increase in the rate of mRNA degradation (RDE binding can shorten the half-life of the mRNA). Some RDE binding proteins may reduce translation and enhance degradation of RNA to reduce the level of polypeptide made. The RDE can be an AU rich element from the 3' UTR of a transcript (e.g., a transcript encoding IL-2 or IFN-γ), or can be a modified 3' UTR that has been engineered to remove one or more microRNA sites (e.g., modified 3'-UTRs of IL-2 or IFN-γ). In an aspect, the expression of the transgene, CAR, DE-CAR and/or Side-CAR polypeptide under the control of an RDE bound by a glycolytic enzyme(s), e.g., GAPDH, is increased by increasing the activity of the enzyme(s) in prosecuting glycolysis. The activity of enzymes in glycolysis can be increased by providing the cell with increased glucose in the cell medium, increasing triose isomerase activity in the cell, or providing the cell with a compound that increases glycolysis in the cell, e.g., tamoxifen or glucose. The RDE can bind to Hu Protein R (HuR). Without wishing to be bound by theory it is expected that HuR binds to some AU-rich RDEs and U-rich RDEs, and can act to stabilize the mRNA, leading to enhanced translation. Thus, cell conditions that result in increased HuR expression can increase expression of transgenes with appropriate AU-rich elements and/or U-rich elements, and conditions that reduce HuR expression can decrease expression of these transgenes. HuR interaction with the 3' UTR of the transgene (or native genes) can also be altered by expressing a recombinant transcript containing HuR binding sites. Expression of these transcripts will reduce the amount of HuR available to bind to the transgene transcript or native HuR regulated transcripts and reduce the half-lives of these transcripts resulting in decreased expression.

In an aspect, bicistronic (or multicistronic) vectors are used to introduce two or more transgene-RDE constructs. These bicistronic constructs can be derived from lenti virus. The two transgenes may be expressed in opposite directions on opposite strands from control regions located in between the nucleic acids encoding two of the transgenes. When more than two transgenes are placed in the construct (multicistronic construct) the third (and additional) transgene may be placed in series with one or both of the transgenes expressed in opposite directions. These additional transgenes may be expressed from the same control region or may have separate control regions. One transgene may encode a CAR and the other transgene(s) may encode payload to be delivered when the CAR is activated. The nucleic acid encoding the payload in the multicistronic or bicistronic construct can be controlled by an RDE that responds to the glycolytic or energy state of the cell. The transgene encoding the CAR can be operably linked to a control region that has a high level of transcription activity, a low level of transcription, and/or is an inducible promoter, and the transgene encoding the payload can be operably linked to a control region that has a lower level of transcription activity, a higher level of transcription, and/or is inducible. The CAR can be operably linked to a control region that has a higher level of transcription (and/or is inducible) and the transgene encoding the payload can be operably linked to a control region that has a lower level of transcription (and/or is inducible). The CAR can also be operably linked to a control region that has a lower level of transcription (and/or is inducible) and the transgene encoding the payload can be operably linked to a control region that has a higher level of transcription (and/or is inducible).

In an aspect, nucleic acids can be used to boost the response of immune cells upon stimulation of the immune cell. For example, the immune cell can produce higher amounts of immune polypeptides (greater $C_{max}$) with faster kinetics of production. The immune polypeptides can include, for example, cytokines, perforins, granzymes, apoptosis inducing polypeptides, etc. The nucleic acids that boost the immune response can comprise control regions operably linked to nucleic acids encoding RDEs for selected RDE binding proteins, so that upon expression of the nucleic acid into RNA the RDEs in the RNA bind the RDE binding proteins that repress expression of a polypeptide, for example, cytokines, perforins, granzymes, and other immune polypeptides. The expression of the RNAs with the RDEs can poise the eukaryotic cell for expression of polypeptide controlled by RDEs. For example, the expression of RNAs with the RDEs may be done in immune cells to poise the cell for expression of immune polypeptides upon stimulation of the immune cell.

Certain RDEs can be associated with certain disease states in a subject. Some disease associated RDEs can be found by comparing the RDEs in the transcripts from normal cells (tissue) to RDEs in the transcripts from diseased or aberrant cells (tissue). RDEs and their corresponding RNA binding proteins from a normal (healthy) cell(s) can be compared to those in a diseased or aberrant cell(s) by trapping the RDE with its RNA binding proteins using methods described in Castello et al., Molc. Cell 63:696-710 (2016), which is incorporated by reference in its entirety for all purposes. RDEs that have aberrant interactions with RNA binding proteins can be linked to a disease state and sequencing of RDEs in the genes or transcripts from an individual may show the susceptibility to disease and/or the disease state of the subject.

RDE control of a CAR, transgene payload, and/or transgene can be controlled through an RDE that is responsive to the metabolic state of the eukaryotic cell. For example, the RDE can be bound by a glycolytic enzyme or other metabolic enzyme and expression of the CAR, transgene payload, and/or transgene can be inhibited by changing the metabolic state of the eukaryotic cell. The RDE could be bound by GAPDH and by turning off glycolysis in the cell (e.g., using an inhibitor of glycolysis) the expression of the CAR, transgene payload, and/or transgene can be inhibited. This inhibition of expression can be used to reduce adverse events caused by expression of the CAR, transgene payload, and/or transgene.

In an aspect, the CAR, DE-CAR, Side-CAR polypeptides, and/or other receptor can be directed against antigens found on acute myeloid leukemia (AML) cells including, for example, CD 33, CD 34, CD 38, CD 44, CD 45, CD 45RA, CD 47, CD 64, CD 66, CD 123, CD 133, CD 157, CLL-1, CXCR4, LeY, PR1, RHAMM (CD 168), TIM-3, and/or WT1. The monoclonal antibody 293C3-SDIE can be used as the extracellular element for the CAR, DE-CAR and/or Side-CAR polypeptides. (Rothfelder et al., 2015, at ash.confex.com/ash/2015/webprogram/Paper81121.html, which is incorporated by reference in its entirety for all purposes) Other antigens for AML are known in the art and may be the target of the CAR, DE-CAR, Side-CAR, and/or other receptor. In an aspect, the CAR, DE-CAR, Side-CAR polypeptides, and/or other receptor can be directed against antigens found on diffuse large cell B-cell lymphoma (DLBCL) cells including, for example, CD19, CD20, CD22, CD79a, CD5, CD10, and CD43. Other antigens for DLBCL are known in the art and may be the target of the CAR, DE-CAR, Side-CAR, and/or other receptor.

In an aspect, the desired amount of CAR expression may consider the target cell concentration, density of target antigen on target cells, the binding affinity ($K_d$) of the extracellular element (antigen binding element) for the target antigen, the concentration of eukaryotic cells with CARs. These parameters and other parameters may be used to arrive at a desired density of CARs on the eukaryotic cell which will define the desired level of CAR expression. The desired amount of CAR expression can also consider the amount of inhibitory receptors (IR) expressed on the eukaryotic cell, and the amount of inhibitory receptor ligand (IRL) expressed on target (and other) cells. The following equations can be used, at least in part, to arrive at a desired amount of CAR polypeptide:

$$\text{Cell Activity} = [\text{target cell}][\text{target antigen density}][K_d][eukaryotic\text{ cells}] \qquad \text{I}$$

$$\text{Cell Activity} = \frac{[\text{target cell}][\text{target antigen density}][K_d][eukaryotic\text{ cells}]}{[IR][IRL]} \qquad \text{II}$$

The desired amount of CAR expression can produce a desired number of CARs on the surface of the eukaryotic cell. The desired amount of CAR expression can produce 2-100,000 CARs (or DE-CARs or Side-CARs) on the surface of the eukaryotic cell. The eukaryotic cell can be a T-lymphocyte and the number of CARs (or DE-CARs or Side-CARs) on the surface of the T-lymphocyte can be 2-100,000. The CAR, DE-CAR, and/or Side-CAR can bind to target ligand with an affinity in the micromolar (μM) range and the desired number of CARs, DE-CARs, and/or Side-CARs on the surface of the T-lymphocyte or natural killer cell can be 100-500,000. The CAR, DE-CAR, and/or Side-CAR can bind to target ligand with an affinity in the nanomolar (nM) range and the desired number of CARs, DE-CARs, and/or Side-CARs on the surface of the T-lymphocyte or natural killer cell can be 2-100,000.

A nucleic acid construct encoding a transcript with selected RDEs can be expressed in an immune cell, for example, a T-lymphocyte. The recombinant transcript with the selected RDEs can bind to and deplete the levels of RDE binding proteins in the T-lymphocyte so that transcripts encoding polypeptides regulated by the depleted RDE binding proteins are expressed at different threshold points of activation for other cellular signals. The use of the RDE constructs can increase the kinetics of expression and/or the Cmax of expression of the polypeptides whose expression is controlled by the RDE.

DETAILED DESCRIPTION OF THE INVENTION

Figure 1:
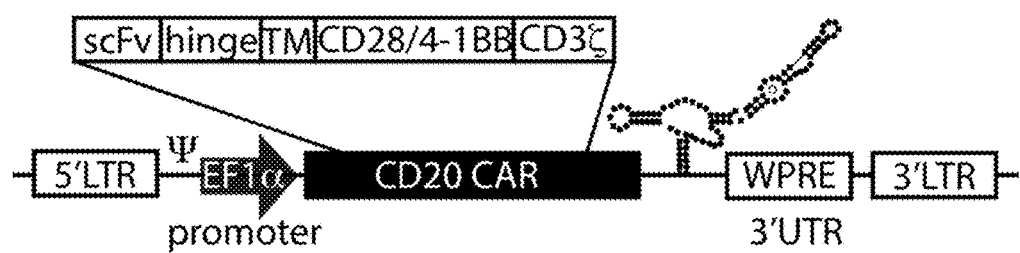
FIG. 1 provides a schematic diagram of a chimeric antigen receptor—RNA control device (Smart CAR).
Figure 2:
FIG. 2 provides a schematic diagram of a chimeric antigen receptor—Destabilizing Element (DE-CAR).
Figure 3:
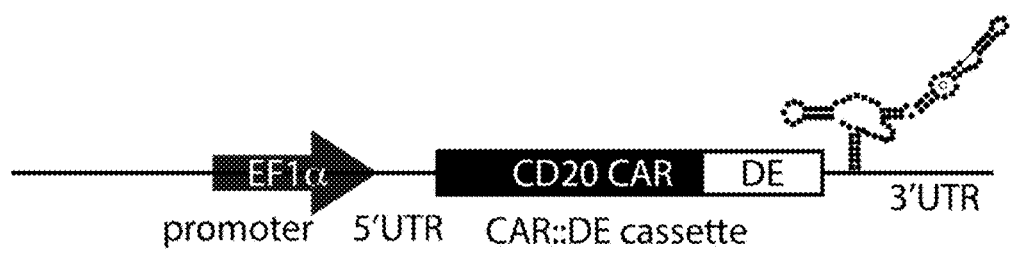
FIG. 3 provides a schematic diagram of a chimeric antigen receptor—Destabilizing Element—RNA control device (Smart-DE-CAR).

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 μg, it is intended that the concentration be understood to be at least approximately or about 10 μg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, an "actuator element" is defined to be a domain that encodes the system control function of the RNA control device. The actuator domain can optionally encode the gene-regulatory function.

As used herein, an "antibody" is defined to be a protein functionally defined as a ligand-binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies exist as intact immunoglobulins, as a number of well characterized fragments produced by digestion with various peptidases, or as a variety of fragments made by recombinant DNA technology. Antibodies can derive from many different species (e.g., rabbit, sheep, camel, human, or rodent, such as mouse or rat), or can be synthetic. Antibodies can be chimeric, humanized, or humaneered. Antibodies can be monoclonal or polyclonal, multiple or single chained, fragments or intact immunoglobulins.

As used herein, an "antibody fragment" is defined to be at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either $V_L$ or $V_H$), camelid VHH domains, and multi-specific antibodies formed from antibody fragments. The term "scFv" is defined to be a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

As used herein, an "antigen" is defined to be a molecule that provokes an immune response. This immune response may involve either antibody production, or the activation of specific immunologically-competent cells, or both. The skilled artisan will understand that any macromolecule, including, but not limited to, virtually all proteins or peptides, including glycosylated polypeptides, phosphorylated polypeptides, and other post-translation modified polypeptides including polypeptides modified with lipids, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be synthesized or can be derived from a biological sample, or can be a macromolecule besides a polypeptide. Such a biological sample can include, but is not limited to a tissue sample, a tumor sample, a cell or a fluid with other biological components.

As used herein, the terms "Chimeric Antigen Receptor" and the term "CAR" are used interchangeably. As used herein, a "CAR" is defined to be a fusion protein comprising antigen recognition moieties and cell-activation elements.

As used herein, a "CAR T-cell" or "CAR T-lymphocyte" are used interchangeably, and are defined to be a T-cell containing the capability of producing CAR polypeptide, regardless of actual expression level. For example a cell that is capable of expressing a CAR is a T-cell containing nucleic acid sequences for the expression of the CAR in the cell.

As used herein, a "costimulatory element" or "costimulatory signaling domain" or "costimulatory polypeptide" are defined to be the intracellular portion of a costimulatory polypeptide. A costimulatory polypeptide can be represented in the following protein families: TNF receptor proteins, Immunoglobulin-like proteins, cytokine receptors, integrins, signaling lymphocytic activation molecules (SLAM proteins), and activating natural killer cell receptors. Examples of such polypeptides include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, MyD88, and the like.

As used herein, a "Cmax" is defined to mean the maximum concentration of a polypeptide produced by a cell after the cell is stimulated or activated to produce the polypeptide.

As used herein, a "cytokine $C_{max}$" is defined to mean the maximum concentration of cytokine produced by an immune cell after stimulation or activation to produce the cytokine.

As used herein, a "cytotoxic polypeptide $C_{max}$" is defined to mean the maximum concentration of cytotoxic polypeptide produced by an immune cell after stimulation or activation to produce the cytotoxic polypeptide.

As used herein, a "destabilizing element" or a "DE" or a "Degron" are used interchangeably, and are defined to be a polypeptide sequence that is inducibly resistant or susceptible to degradation in the cellular context by the addition or subtraction of a ligand, and which confers this stability modulation to a co-translated polypeptide to which it is fused in cis.

As used herein, an "effective amount" or "therapeutically effective amount" are used interchangeably, and defined to be an amount of a compound, formulation, material, or composition, as described herein effective to achieve a particular biological result.

As used herein, an "epitope" is defined to be the portion of an antigen capable of eliciting an immune response, or the portion of an antigen that binds to an antibody. Epitopes can be a protein sequence or subsequence that is recognized by an antibody.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will be an expression vector or expression construct.

As used herein, an "extracellular element" is defined as the antigen binding or recognition element of a Chimeric Antigen Receptor.

As used herein, a "hematopoietic cell" is defined to be a cell that arises from a hematopoietic stem cell. This includes but is not limited to myeloid progenitor cells, lymphoid progenitor cells, megakaryocytes, erythrocytes, mast cells, myeloblasts, basophils, neutrophils, eosinophils, macrophages, thrombocytes, monocytes, natural killer cells, T lymphocytes, B lymphocytes and plasma cells.

As used herein, "heterologous" is defined to mean the nucleic acid and/or polypeptide are not homologous to the host cell. For example, a construct is heterologous to a host cell if it contains some homologous sequences arranged in a manner not found in the host cell and/or the construct contains some heterologous sequences not found in the host cell.

As used herein, an "intracellular element" is defined as the portion of a Chimeric Antigen Receptor that resides on the cytoplasmic side of the eukaryotic cell's cytoplasmic membrane, and transmits a signal into the eukaryotic cell. The "intracellular signaling element" is that portion of the intracellular element which transduces the effector function signal which directs the eukaryotic cell to perform a specialized function.

As used herein, "RNA destabilizing element" or "RDE" are used interchangeably and both are defined as a nucleic acid sequence in an RNA that is bound by proteins and which protein binding changes the stability and/or translation of the RNA. Examples of RDEs include Class I AU rich elements (ARE), Class II ARE, Class III ARE, U rich elements, GU rich elements, and stem-loop destabilizing elements (SLDE). Without wishing to be bound by theory, RDE's may also bind RNA stabilizing polypeptides like HuR.

As used herein, an "RNase III substrate" is defined to be an RNA sequence motif that is recognized and cleaved by an endoribonuclease of the RNase III family.

As used herein, an "RNAi substrate" is defined to be an RNA sequence that is bound and/or cleaved by a short interfering RNA (siRNA) complexed to an effector endonuclease of the Argonaute family.

As used herein, a "single chain antibody" (scFv) is defined as an immunoglobulin molecule with function in antigen-binding activities. An antibody in scFv (single chain fragment variable) format consists of variable regions of heavy ($V_H$) and light ($V_L$) chains, which are joined together by a flexible peptide linker.

As used herein, a "T-lymphocyte" or "T-cell" is defined to be a hematopoietic cell that normally develops in the thymus. T-lymphocytes or T-cells include, but are not limited to, natural killer T cells, regulatory T cells, helper T cells, cytotoxic T cells, memory T cells, gamma delta T cells and mucosal invariant T cells.

As used herein, "transfected" or "transformed" or "transduced" are defined to be a process by which exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

As used herein, a "transmembrane element" is defined as the element between the extracellular element and the intracellular element. A portion of the transmembrane element exists within the cell membrane.

Destabilizing Elements

Destabilizing elements (DE) are stability-affecting polypeptides capable of interacting with a small-molecule ligand, the presence, absence, or amount of which ligand is used to modulate the stability of the DE-polypeptide of interest. The polypeptide of interest can be an immunomodulatory polypeptide. The polypeptide of interest can also be a CAR. Binding of ligand by a DE-CAR can reduce the degradation rate of the DE-CAR polypeptide in the eukaryotic cell. Binding of ligand by the DE-CAR can also increase the degradation rate of the DE-CAR in the eukaryotic cell.

Exemplary destabilizing elements or DEs are described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes. For example, U.S. Ser. No. 15/070,352 describes DEs derived from variants of the FKBP protein, variants of the DHFR protein, variant estrogen receptor binding domain (ERBD), and variant phototropin 1 of Avena sativa (AsLOV2). Other examples of variant FKBP nucleic acids and polypeptides are described in US published patent application 20120178168 A1 published on Jul. 12, 2012, which is hereby incorporated by reference in its entirety for all purposes. Other examples of variant DHFR nucleic acids and polypeptides are described in US published patent application 20120178168 A1 published on Jul. 12, 2012, which is hereby incorporated by reference in its entirety for all purposes. Other examples of variant ERBD nucleic acids, polypeptides, and ligands are described in published US patent application 20140255361, which is hereby incorporated by reference in its entirety for all purposes. Other examples of variant AsLOV2 DEs are described in Bonger et al., ACS Chem. Biol. 2014, vol. 9, pp. 111-115, and Usherenko et al., BMC Systems Biology 2014, vol. 8, pp. 128-143, which are incorporated by reference in their entirety for all purposes.

Other DEs can be derived from other ligand binding polypeptides as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Other ligand binding polypeptides from which variants can be made for use as DEs, include for example, enzymes, antibodies or antibody fragments or antibody fragments engineered by recombinant DNA methods with the variable domain, ligand binding receptors, or other proteins. Examples of enzymes include bromodomain-containing proteins, FKBP variants, or prokaryotic DHFR variants. Examples of receptor elements useful in making DEs include: variant ERBD, or other receptors that have ligands which are nontoxic to mammals, especially humans.

The ligand(s) for the DE can be selected for optimization of certain attributes for therapeutic attractiveness, for example, as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

RNA Control Devices

The Ribonucleic acid (RNA) control devices disclosed herein can exhibit tunable regulation of gene expression, design modularity, and target specificity. The RNA control devices can act to rewire information flow through cellular networks and reprogram cellular behavior in response to changes in the cellular environment. In regulating polypeptide expression, the RNA control devices can serve as synthetic cellular sensors to monitor temporal and spatial fluctuations in the levels of diverse input molecules. RNA control devices represent powerful tools for constructing ligand-controlled gene regulatory systems tailored to modulate the expression of CAR, DE-CAR, and/or Side-CAR polypeptides of the invention in response to specific effector molecules enabling RNA regulation of target CAR, DE-CAR, and/or Side-CAR constructs in various living systems.

The RNA control devices disclosed herein comprise a regulatory element and a sensor element. The RNA control devices disclosed herein can comprise a single element with both a regulatory and sensory function. The RNA control devices disclosed herein can comprise a regulatory function and a sensory function. The RNA control devices disclosed herein can comprise a regulatory element, a sensor element, and an information transmission element (ITE) that functionally couples the regulatory element and the sensor element. The ITE can be based on, for example, a strand-displacement mechanism, an electrostatic interaction, a conformation change, or a steric effect. The sensing function of the RNA control device leads to a structural change in the RNA control device, leading to altered activity of the acting function. Some mechanisms whereby these structural changes can occur include steric effects, hydrophobicity driven effects (log p), electrostatically driven effects, nucleotide modification effects (such as methylation, pseudouradination, etc.), secondary ligand interaction effects and other effects. A strand-displacement mechanism can use competitive binding of two nucleic acid sequences (e.g., the competing strand and the RNA control device strand) to a general transmission region of the RNA control device (e.g., the base stem of the aptamer) to result in disruption or restoration of the regulatory element in response to ligand binding to the sensor element.

The RNA control device can comprise a sensor element and a regulatory element. The sensor element can be an RNA aptamer. The RNA control device can have more than one sensor element. In some aspects, the regulatory element can be a ribozyme. The ribozyme can be a hammerhead ribozyme. The ribozyme can also be a hairpin ribozyme, or a hepatitis delta virus (HDV) ribozyme, or a Varkud Satellite (VS) ribozyme, a glmS ribozyme, and/or other ribozymes known in the art.

The RNA control device or devices can be embedded within a DNA sequence. The RNA control device can be encoded for in messenger RNA. Multiple RNA control devices can be encoded in cis with a transgene-encoding mRNA. The multiple RNA control devices can be the same and/or a mixture of different RNA control devices repeated. The nucleic acid that is used to encode the RNA control device can be repeated. By including multiple RNA control devices, sensitivity and dose response may be tailored or optimized. The multiple RNA control devices can each be specific for a different ligand. This can mitigate unintentional expression due to endogenously produced ligands that interact with the sensor element.

RNA Control Devices: Sensor Elements

Exemplary sensor elements are described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes. Sensor elements can be derived from aptamers. An "aptamer" is a nucleic acid molecule, such as RNA or DNA that is capable of binding to a specific molecule with high affinity and specificity (Ellington et al., Nature 346, 818-22 (1990); and Tuerk et al., Science 249, 505-10 (1990), which are hereby incorporated by reference in their entirety for all purposes). For a review of aptamers that recognize small molecules, see Famulok, Science 9:324-9 (1999), which is hereby incorporated by reference in its entirety for all purposes.

The binding affinity of the aptamer for its ligand must be sufficiently strong and the structure formed by the aptamer when bound to its ligand must be significant enough so as to switch an RNA control device of the invention between "on" and "off" states. The association constant for the aptamer and associated ligand is such that the ligand(s) bind to the aptamer and has the desired effect at a concentration of ligand obtained upon administration of the ligand to a subject. For in vivo use, for example, the association constant should be such that binding occurs well below the concentration of ligand that can be achieved in the serum or other tissue, or well below the concentration of ligand that can be achieved intracellularly since cellular membranes may not be sufficiently permeable to allow the intracellular ligand concentration to approach the level in the serum or extracellular environment. The required ligand concentration for in vivo use can also be below that which could have undesired effects on the subject.

Ligands for RNA Control Devices

RNA control devices can be controlled via the addition of exogenous ligand or synthesis (or addition) of endogenous ligands with desired binding properties, kinetics, bioavailability, etc., for example, as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The ligand can be a naturally occurring, secreted metabolite. For example, a ligand that is uniquely produced by a tumor, or present in the tumor microenvironment is the ligand for the sensor element and binding of this ligand to the sensor element changes the activity of the RNA control device. Thus the control device is responsive and controlled through chemical signaling or proximity to a tumor.

The ligand can be selected for its pharmacodynamic or ADME behavior. For example ligands may be preferentially localized to specific portions of the human anatomy and physiology. For example certain molecules are preferentially absorbed or metabolized in the gut, the liver, the kidney etc. The ligand can be selected to demonstrate preferential pharmacodynamic behavior in a particular organ. For example, it would be useful to have a ligand that preferentially localizes to the colon for a colorectal carcinoma so that the peak concentration of the ligand is at the required site, whereas the concentrations in the rest of the body is minimized, preventing undesired, nonspecific toxicity. The ligand can be selected to demonstrate non preferential pharmacodynamic behavior. For example, for disseminated tumors like hematological malignancies, it would be useful to have non variant concentration of the ligand throughout the body.

The ligand for the RNA control device (or DE) can be folinic acid, S-folinic acid, R-folinic acid, vitamin C (ascorbic acid), acyclovir, or the like.

RNA Control Devices: Regulatory Elements

The regulatory element can comprise a ribozyme, or an antisense nucleic acid, or an RNAi sequence or precursor that gives rise to a siRNA or miRNA, or a shRNA or precursor thereof, or an RNAse III substrate, or an alternative splicing element, or a transcription terminator, or a ribosome binding site, or an IRES, or a polyA site. Regulatory elements useful in the present invention are, for example, described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

General approaches to constructing oligomers useful in antisense technology have been reviewed, for example, by van der Krol et al. (1988) Biotechniques 6:958-976; and Stein et al. (1988) Cancer Res 48:2659-2668, which are hereby incorporated by reference in their entirety for all purposes. Certain miRNAs that may be used in the invention are described in Brennecke et al., Genome Biology 4:228 (2003); Kim et al., Mol. Cells. 19:1-15 (2005), which are hereby incorporated by reference in their entirety for all purposes.

The RNA control devices can have multiple regulatory elements, and/or multiple sensor elements. The multiple sensor elements can recognize the same or different ligands. The multiple sensor elements can have different (e.g., incremental, additive or synergistic) effects on the regulatory element.

RNA Destabilizing Elements

RNA destabilizing elements (RDE) are nucleic acids that affect or maintain the stability of an RNA molecule or the translation kinetics of an RNA molecule. Some RDEs are bound by polypeptides which destabilize (e.g., cleave) the RNA, or prevent translation, leading to loss of function for the RNA. Some RDE binding polypeptide stabilizes the RNA increasing the half-life of the RNA. RDEs can be used to control the expression of a transgene, e.g., a transgene encoding a chimeric antigen receptors. RDEs can be used with RNA control devices, DEs, and/or Side CARs to regulate the expression of a transgene. The RDEs can also be used to control expression of transgenes encoding polypeptides other than a CAR. Other transgenes may encode, for example, a cytokine, an antibody, a checkpoint inhibitor, a granzyme, an apoptosis inducer, complement, a cytotoxic small molecule, other cytotoxic compounds, a polypeptide for imaging, or other polypeptide that can have a desired effect. The RDE can control the delivery of a transgene payload. Examples of RDEs include, for example, AU rich elements, U rich elements, GU rich elements, and certain stem-loop elements. Exemplary RDEs are described in Kovarik et al., Cytokine 89:21-26 (2017); Ray et al., Nature 499:172-177 (2013); Castello et al., Cell 149:1393-1406 (2012); Vlasova et al., Molc. Cell. 29:263-270 (2008); Barreau et al., Nucl. Acids Res. vol 33, doi:10.1093/nar/gki1012 (2006); Meisner et al., ChemBioChem 5:1432-1447 (2004); Guhaniyogi et al., Gene 265:11-23 (2001), all of which are incorporated by reference in their entirety for all purposes.

The RDE can be a Class I AU rich element (dispersed AUUUA (SEQ ID NO:8) in U rich context), a Class II AU rich element (overlapping $(AUUUA)_n$), a Class III AU rich element (U-rich stretch), a stem-loop destabilizing element (SLDE), a cytokine 3' UTR (e.g., INF-γ, IL-2, T-cell receptor α chain, TNFα, IL-6, IL-8, GM-CSF, G-CSF etc.), and a sequence of AUUUAUUUAUUUA (SEQ ID NO: 9). Khabar, WIREs RNA 2016, doi: 10.1002/wrna.1368 (2016); Palanisamy et al, J. Dent. Res. 91:651-658 (2012), both of which are incorporated by reference in their entirety for all purposes. The RDE can also be a GU rich element comprised of one or more of, for example, UUGUU (SEQ ID NO: 10), UGGGGAU (SEQ ID NO: 11), or GUUUG (SEQ ID NO: 12). The RDE can be a U-rich element comprised of one or more of, for example, UUUGUUU (SEQ ID NO: 13), TIIVUUNNUUU (SEQ ID NO: 14), UUUAUUU (SEQ ID NO: 15), UUUUUUU (SEQ ID NO: 16), UUAGA (SEQ ID NO: 17), or AGUUU (SEQ ID NO: 18). In some aspects, multiple RDEs can be combined to make a regulatory unit, for example, multiple RDEs that have the same sequence can be arranged in a concatemer or can be arranged with intervening sequence in between some or all of the RDEs. The RDE sequence can be modified to increase or decrease the affinity of an RNA binding protein(s) for the RDE. For example, an AU rich RDE can be changed to alter the affinity of glyceraldehyde phosphate dehydrogenase (GAPDH) to the RDE. This change in affinity can alter the GAPDH-activation threshold for expression of a transgene regulated by the RDE to which GAPDH binds.

The RDE can be from the 3' UTR of a gene encoding, for example, IL-1, IL-2, IL-3, IL-4, IL-6, IL-8, IL-10, GM-CSF, G-CSF, VEG F, $PGE_2$, COX-2, MMP (matrix metalloproteinases), bFGF, c-myc, c-fos, betal-AR, PTH, interferon-gamma, MyoD, p21, Cyclin A, Cyclin B1, Cyclin D1, PAI-2, NOS HANOS, TNF-alpha, interferon-alpha, bcl-2, interferon-beta, c-jun, GLUT1, p53, Myogenin, NF-M, or GAP-43, lymphocyte antigen 96, SUPV3L1, SFtPA2, BLOC1S2, OR10A6, OR8D1, TRPT1, CIP29, EP400, PLE2, H3ST3A1, ZNF571, PPP1R14A, SPAG4L, OR10A6 and KIR3DL. Other RDEs are found in, for example, the 3'-UTRs from GLMN, AMY2B, AMY2A, AMY2A, AMY1A, TRIM33, TRIM33, TRIM33, CSRP1, PPP1R12B, KCNH1, Reticulon_4, MRPL30, Nav1.2, Tissue_factor_pathway_inhibitor, EEF1B2, CRYGB, ARMC9, RPL15, EAF2, MRPS22, MRPS22, COPB2, PDCD10, RE1-silencing_transcription_factor, Amphiregulin, AP1AR, TLR3, SKP2, Peptidylglycine_alpha-amidating_monooxygenase, TNFAIP8, Interleukin_9, PCDHA2, PCDHA12, Aldehyde_dehydrogenase_5_family,_member_A1, KCNQ5, COX7A2, Monocarboxylate_transporter_10, MLLT4, PHF10, PTPN12, MRNA_(guanine-N7-)-methyl-transferase, WHSC1L1, Tricho-rhino-phalangeal_syndrome_Type_1, Interferon_alpha-1, ZCCHC6, Retinitis_pigmentosa_GTPase_regulator, MED14, CLCNS, DNA2L, OR52D1, NELL1, SLC22A25, SLC22A10, TRPC6, CACNA2D4, EPS8, CT2_(gene), Mitochondrial_ribosomal_protein_L42, TAOK3, NUPL1, Endothelin_receptor_type_B, Survival_of_motor_neuron_protein-interacting_protein_1, POLE2, Hepatic_lipase, TPSG1, TRAP1, RPS15A, HS3ST3A1, CROP_(gene), Apolipoprotein_H, GRB2, CEP76, VPS4B, Interleukin_28B, IZUMO1, FGF21, PPP1R15A, LIN7B, and CDC45-related_protein.

Still other RDEs can be found in, for example, the 3'UTRs of SCFD1, MAL2, KHSRP, IQCB1, CAMP_responsive_element_modulator, MFAP5, SBF2, FKBP2, PDCD10, UBE2V2, NDUFAB1, Coiled-Coil_Domain_Containing_Protein, ALG13, TPTE, Enaptin, Thymopoietin, Delta-like_1, C11orf30, Actinin_alpha_4, TMEM59, SP110, Dicer, TARDBP, IFNA17, IFNA16, IFNA14, ZMYM3, Interleukin_9,_type_I, OPN1SW, THSD1, ERGIC2, CAMK2B, WDR8, FXR1, Thymine-DNA_glycosylase, Parathyroid_hormone-related_protein, OSBPL3, Ran, GYPE, AKAP4, LOC642658, L2HGDH, AKAP1, Zinc_finger_protein_334, TC2N, FKBPL, GRB14, CXorf67, CXorf66, CEP76, Gastricsin, CEP70, CYP26A1, NAA35, Aryl_hydrocarbon_receptor_nuclear_translocator, KLC4, GPR112, LARP4, NOVA1, UBE2D3, ITGA6, GPR18, MGST_type_A, RE1-silencing_transcription_factor, ASPM, ZNF452, KIR2DS4, AHSA1, TMTC4, VSX1, P16, MRPL19, CCL20, TRPT1, Hepatic_lipase, PDLIM5, CCDC53, 'CCDC55, GAPVD1, HOXB2, KCNQ5, BRCC3, GTF2IRD1, CDK5RAP3, Transcription_factor_II_B, ZEB1, IRGM, SLC39A6, RHEB, PSIP1, RPS6KA5, Urokinase_receptor, GFM1, DNAJC7, Phosphoinositide-dependent_kinase-1, LMOD3, TTC35, RRP12, ATXN2, ACSM3, SOAT1, FGF8, HNRPH3, CTAGES, POLG2, DYRK3, POLK, Cyclin-dependent_kinase_inhibitor_1C, CD137, Calmodulin_1, ZNF571, CNOT2, CRYZL1, SMC3, SMC4, SLC36A1, Decorin, HKR1, ERC1, S100A6, RIMS1, TMEM67, Mitochondrial_ribosomal_protein_L42, MECP2, RNF111, SULT1A1, MYLK3, TINAG, PRKAR1A, RGPDS, UBE2V1, SAR1B, SLC27A6, ZNF638, RAB33A, TRIOBP, MUCL1, CADPS2, MCF2L, TBCA, SLC17A3, LEO1, IFNA21, RUNX1T1, PRKD2, ATP11B, MORC2, RBM6, KLRD1, MED31, PPHLN1, HMGB2, DNA_repair_and_recombination_protein_RAD54-like, RBM9', ARL11, HuD, SPEF2, CBLL1, SLC38A1, 'Caspase_1', S100G, CA1, CELA1_, PTS, ITM2B, Natriuretic_peptide_precursor_C, TRPP3, IMPDH2, DPYS, CDCA3, EFCAB6, SLIT2, SIPA1L1, FIP1L1, ATP6V1B2, HSD17B4, HSD17B7, NDUFC1, CROP, CD48, APPBP1, CD44, CD46, Histone_deacetylase_2_type_XI, Interleukin_4, Tricho-rhino-phalangeal_syndrome_Type_1, SEC61G, TRIP12, PLEKHO1, SEC61B, ST6GALNAC1, CPVL, E2F7, UTP20, E2F5, PARD3, EXOC7, HEXB, Caspase_recruitment_domain-containing_protein_8, MBD4, PPP4C, Helicase, Phosducin, SPG11, CGGBP1, PSKH1, Cathepsin_S, orexin, IMMP2L, C2orf28, Laminin, EIF3S6, LRRC41_type_XII, Cathepsin_C, HPS6, ARAF, Zinc_finger_and_BTB_domain-containing_protein_16, Sex_hormone-binding_globulin, FBLN2, Suppressor_of_cytokine_signaling_1, TMEM126A, DOM3Z, TSFM POLQ-like, DYNLT3, CDH9, EAF2, MIPEP, NDUFA12, HDAC8, MKKS, FGG, IL36G, CDCA7, CRISPLD2, Olfactomedin-like_2b, MRPL32, MRPL33, AHI1, SMARCAL1, UTP14A, SSH2, Dystonin, Contactin_6, PPFIBP1, THOC1, CNOT1, RHCE, SLC41A3, SLC2A9, SNAP23, RFX3, GNG4, MRPL40, LSR, Angiogenin, TRIP4, VRK1, COUP-TFII, FOXP2, SNX2, Nucleoporin_85, RPL37A, RPL27A, SEC62, Calcium-activated_potassium_channel_subunit_alpha-1, SMARCE1, RPL17, CEP104, CEP290, VPS29, ANXA4, Zinc_finger_protein_737, DDX59, SAP30, NEK3, Exosome_component_9, Receptor_for_activated_C_kinase_1, Peptidylprolyl_isomerase_A, TINP1, CEACAM1, DISC1, LRRTM1, POP1_Lamin_B1, SREBP_cleavage-activating_protein, COX6C, TLR_1, ARID2, LACTB, MMS22L, UBE2E3, DAP3, ZNF23, SKP2, GPR113, IRF9 Ghrelin_O-acyltransferase, NEIL3, EEF1E1, COX17, ESD_, Dentin_sialophosphoprotein, HDAC9, RFC4, CYLD, RPLPO, EIF2B3, UGT2A1, FABP7, TRIP11, PLA2G4A, AKR1C3, INTS12, MYH1, ZBTH17, MYH4, NLRP2, MECOM, MYH8, Thermogenin_receptor_2, IFI16, THYN1, RAB17, ETFA, Cystic_fibrosis_transmembrane_conductance_regulator, F13B, RAB6A, ST8SIA1, SATB2, SATB1, HMG20B, UHRF1, CNOT3, Prostaglandin_EP2_receptor, FAM65B, Peroxisome_proliferator-activated_receptor_gamma, KvLQT2, GRIK5, SHOC2, Cortactin, FANCI, KIAA1199, Kynureninase, Decoy_receptor_1, NEU3, PHF10, Methyl-CpG-binding_domain_protein_2, RABGAP1, CEP55, SF3B1, MSHS, MSH6, CREB-binding_protein, LIMS1, SLC5A4, CCNB_1IP1, RNF34, SORBS2, UIMC1, SOX5, YWHAZ, ICOSLG, NOP58, Zinc_finger_protein_679, PHKB, MED13, ABCB7, COQ9, C14orf104, Zinc_finger_protein_530, KLRC2, LSM8, NBR1, PRKCD, Long-chain-aldehyde_dehydrogenase, MTSS1, Somatostatin, Ubiquitin_carboxyl-terminal_hydrolase_L5, WDR72, FERMT3, Nuclear_receptor_related-1_protein, Citrate_synthase, VPS11, KIZ, ZFYVE27, BCKDHB, Hypocretin, CACNG2, PTCH1, Carbonic_anhydrase_4, Nucleoporin_107, LDL_receptor, LEKTI, FBXO11, NDUFB3, FCHO2, CEP78, RAPGEF6, PPIL3, NIN, RAPGEF2, Growth_hormone_1, Growth_hormone_2, MNAT1, Nav1, MAP3K8, SUGT1, LAIR1, Hyaluronan-mediated_motility_receptor, MAP3K2, MPP2, TFB2M, CRB3, MPP5, CACNA1G, DLGAP2, INHBA, MAGI2, CIP29, SETDB1, Cytochrome_b5, TRPV2, Interleukin_1_receptor, HOXD8, TIMM10, ATXN2L, CLCN2, CREB1, TNIP1, CBLB, Factor_V, USP33, SON, RBBP8, SLC22A18, PTPN12, ADCY8, MYLK, KIF23, REXO2, BST1, TOP3B, COPB1, AXIN2, COPB2, TNRC6B, Guanidinoacetate_N-methyltransferase, Acyl-CoA_thioesterase_9, C4orf21, TSHB, FRS3, EPB41, Cyclin_T2, LAIR2, Nucleoporin_43, APLP2, TNFRSF19, Death-associated_protein_6, Epithelial_cell_adhesion_molecule, CLEC7A, Gephyrin, CLDND1, VPS37A, PCDHAC2, Bone_morphogenetic_protein_4, NVL, RBM33, RNF139, Sperm_associated_antigen_5, PLCB1, Glial_cell_line-derived_neurotrophic_factor, PARP4, PARP1, MAN2A1, Bone_morphogenetic_protein_1, PAX4, BCCIP, MMP7, Decoy_receptor_3, RAMP2, NCAPD3, LRRC37A, RWDD3, UBE2A, UBE2C, SLC3A1, MRPS22, CDC14A, ITSN1, POLE2, MYC-induced_nuclear_antigen, TMLHE, Glutamate_carboxypeptidase_II, GPR177, PPP2R5C, KIAA1333, RPP38, MYO1F, Farnesoid_X_receptor, Caldesmon, FBXO4, FBXO5, OPN1MW, PIGN, ARNTL2, BCAS3, C6orf58, PHTF2, SEC23A, NUFIP2, OAZ1, Osteoprotegerin, ANAPC4, ATP6V0A2, SPAM1, PSMA6, TAS2R30, RABEP1, DPM3, SLC6A15, RPS26, RPS27, RPS24, RPS20, RPS21, ARH-GAP24, Catechol-O-methyl_transferase, ERCC5, Transcription_initiation_protein_SPT3_homolog, OR1E1, ZNRF1, GMEB1, CCT2_GNAQ, Mucin_6, Mucin_4, LRPS, PDE9A, C2orf3, EZH2, Epidermal_growth_factor_receptor, TMTC2, PDE4A, EPH_receptor_A4, PPIB, DENND4A, ANTXR1, ANTXR2, Nucleoporin_88, SLCO1B3, COGS, RBMS1, MAP7, HIST2H2BE, AEBP2, DCLRE1A, RPL24, HNRPA2B1, RPL21, RPL23, MAPKAP1, NIPBL, ATG7, SERPINI2, GYLTL1B, ATP5G2, DIP2A, AMY2A, CEP63, TDRD7, PIEZO1, CLDN20, GRXCR1, PMEL, NIF3L1, MCC_, PCNX, TMBIM4, DUSP12, ZMYND8, GOSR1, Interferon_gamma_receptor_1, LDB3, PON3, C1D, ABCC8, COQ7, COQ6, AMELY, HAVCR1, PICALM, Sjogren_syndrome_antigen_B, PLK4, HBB, AKT1, PCDHGB7, C6orf10, UBR1, Retinoblastoma-like_protein_1, GRK6, WWC2, GRK4, INPP4B, SLC34A1, GOLGA2, MYCBP2, PTP4A2, NUCB2, MAGOH, RPP40, Alpha-2A_adrenergic_receptor, SPAG11B, Nucleoporin_205, COG1, Motile_sperm_domain_containing_3, KCNMB3, Motile_sperm_domain_containing_1, KLHL7, KCNN2, TSPAN8, GPR21, Translocator_protein, HNRNPLL, ABHD5, CAB39L, Amphiregulin, GPR1, Interleukin_18, EIF4G3, Interleukin_15, CCDC80, CD2AP, NFS1, GRB2, ULBP2, Vascular_endothelial_growth_factor_C, RPS3, TLR8, BCL2-related_protein_A1, RHOT1, Collagen, Centromere_protein_E, STMN2, HESX1, RPL7, Kalirin, PCMT1, HLA-F, SUMO2, NOX3, EP400, DNM3, EED, NGLY1, NPRL2, PLAC1, Baculoviral_IAP_repeat-containing_protein_3, C7orf31, TUBA1C, HAUS3, IFNA10, MYST4, DCHS1, SIRT4, EFEMP1, ARPC2, MED30, IFT74, PAK1IP1, DYNC1LI2, POLR2B, POLR2H, KIF3A, PRDM16, PLSCR5, PEX5, Parathyroid_hormone_1_receptor, CDC23, RBPMS, MAST1, NRD1, BAT5, BAT2, Dock11, GCSH, POF1B, USP15, POT1, MUTYH, CYP2E1, FAM122C, A1_polypeptide, Flavin_containing_monooxygenase_3, HPGD, LGALS13, MTHFD2L, Survival_motor_neuron_domain_containing_1, PSMA3, MRPS35, MHC_class_I_polypeptide-related_sequence_A, SGCE, REPS1, PPP1R12A, PPP1R12B, PABPC1, MAPK8, PDCD5, Phosphoglucomutase_3, Ubiquitin_C, GABPB2, Mitochondrial_translational_release_factor_1, PFDN4, NUB1, SLC13A3, ZFP36L1, Galectin-3, CC2D2A, GCA, Tissue_factor_pathway_inhibitor, UCKL1, ITFG3, SOS1, WWTR1, GPR84, HSPA14, GJC3, TCF7L1, Matrix_metallopeptidase_12, ISG20, LILRA3, Serum_albumin, Phosducin-like, RPS13, UTP6, HP1BP3, IL12A, HtrA_serine_peptidase_2, LATS1, BMF_, Thymosin_beta-4, B-cell_linker, BCL2L11, Coagulation_factor_XIII, BCL2L12, PRPF19, SFRS5, Interleukin_23_subunit_alpha, NRAP, 60S_ribosomal_protein_L14, C9orf64, Testin, VPS13A, DGKD, PTPRB, ATP5C1, KCNJ16, KARS, GTF2H2, AMBN, USP13, ADAMTSL1, TRO_, RTF1, ATP6V1C2, SSBP1, SNRPN_upstream_reading_frame_protein, RPS29, SNRPG, ABCC10, PTPRU, APPL1, TINF2, TMEM22, UNC45A, RPL30, PCDH7, Galactosamine-6_sulfatase, UPF3A, ACTL6A, ACTL6B, IL3RA, SDHB, Cathepsin_L2, TAS2R7, Cathepsin_L1, Pituitary_adenylate_cyclase-activating_peptide, RPN2, DYNLL1, KLK13, NDUFB3, PRPF8, SPINT2, AHSA1, Glutamate_carboxypeptidase_II, DRAP1, RNASE1, Olfactomedin-like_2b, VRK1, IKK2, ERGIC2, TAS2R16, CAMK2G, CAMK2B, Estrogen_receptor_beta, NADH_dehydrogenase, RPL19, NUCB2, KCTD13, ubiquinone, H2AFY, CEP290, PABPC1, HLA-F, DHX38, KIAA0922, MPHOSPH8, DDX59, MIB2_, ZBP1, C16orf84, UACA, C6orf142, MRPL39, Cyclin-dependent_kinase_7, Far_upstream_element-binding_protein_1, SGOL1, GTF2IRD1, ATG10, Dermcidin, EPS8L2, Decorin, Nicotinamide_phosphoribosyltransferase, CDC20, MYB, WNT5A, RBPJ, DEFB103A, RPS15A, ATP5H, RPS3, FABP1, SLC4A8, Serum_amyloid_P_component, ALAS1, MAPK1, PDCD5, SULT1A1, CHRNA3, ATXN10, MNAT1, ALG13, Ataxin_3, LRRC39, ADH7, Delta-sarcoglycan, TACC1, IFNA4, Thymic_stromal_lymphopoietin, LGTN, KIAA1333, MSH6, MYOT, RIPK5, BCL2L11, RPL27, Rnd1, Platelet_factor_4, HSD17B7, LSM8, CEP63, INTS8, CTNS, ASAHL, CELA3A, SMARCAL1, HEXB, SLC16A5, MAP3K12, FRMD6.

The RDE can be a Class I AU rich element that arises from the 3' UTR of a gene encoding, for example, c-myc, c-fos, beta1-AR, PTH, interferon-gamma, MyoD, p21, Cyclin A, Cyclin B1, Cyclin D1, PAI-2, or NOS HANOS. The RDE can also be a Class II AU rich element and arises from the 3' UTR of a gene encoding, for example, GM-CSF, TNF-alpha, interferon-alpha, COX-2, IL-2, IL-3, bcl-2, interferon-beta, or VEG-F. The RDE can be a Class III AU rich element that arises from the 3' UTR of a gene encoding, for example, c-jun, GLUT1, p53, hsp 70, Myogenin, NF-M, or GAP-43. Other RDEs may be obtained from the 3'-UTRs of a T-cell receptor subunit ($\alpha$, $\beta$, $\gamma$, or $\delta$ chains), cytotoxic T-lymphocyte-associated antigen 4 (CTLA4), programmed cell death protein (PD-1), Killer-cell Immunoglobulin-like Receptors (KIR), and Lymphocyte Activation Gene-3 (LAG3), and other checkpoint inhibitors. Still other RDEs may be obtained from the 3'-UTR of senescence-associated secretory phenotype genes disclosed in Coppe et al., Ann. Rev. Pathol. 5:99-118 (2010), which is incorporated by reference in its entirety for all purposes (e.g., see Table 1).

The RDE can be bound by certain polypeptides including, for example, ARE poly(U) binding/degradation factor (AUF-1), tristetraprolin (TTP), human antigen-related protein (HuR), butyrate response factor 1 (BRF-1), butyrate response factor 2 (BRF-2), T-cell restricted intracellular antigen-1 (TIA-1), TIA-1 related protein (TIAR), CUG triplet repeat, RNA binding protein 1 (CUGBP-1), CUG triplet repeat, RNA binding protein 2 (CUGBP-2), human neuron specific RNA binding protein (Hel-N1, Hel-N2), RNA binding proteins HuA, HuB and HuC, KH-type splicing regulatory protein (KSRP), 3-methylglutaconyl-CoA hydratase (AUH), glyceraldehyde 3-phosphate dehydrogenase (GAPDH), heat shock protein 70 (Hsp70), heat shock protein 10 (Hsp10), heterogeneous nuclear ribonucleoprotein A1 (hnRNP A1), heterogeneous nuclear ribonucleoprotein A2 (hnRNP A2), heterogeneous nuclear ribonucleoprotein A3 (hnRNP A3), heterogeneous nuclear ribonucleoprotein C (hnRNP C), heterogeneous nuclear ribonucleoprotein L (hnRNP L), Bcl-2 AU-rich element RNA binding protein (TINO), Poly(A) Binding Protein Interacting Protein 2 (PAIP2), IRP1, pyruvate kinase, lactate dehydrogenase, enolase, and aldolase. The RDE binding protein also can be an enzyme involved in glycolysis or carbohydrate metabolism, such as, for example, Glyceraldehyde Phosphate Dehydrogenase (GAPDH), enolase (ENO1 or ENO3), Phosphoglycerate Kinase (PGK1), Triosephosphate Isomerase (TPI1), Aldolase A (ALDOA), Phosphoglycerate Mutase (PGAM1), Hexokinase (HK-2), or Lactate Dehydrogenase (LDH). The RDE binding protein can be an enzyme involved in the Pentose Phosphate Shunt, including for example, Transketolase (TKT) or Triosephosphate Isomerase (TPI1). Additional exemplary RNA binding proteins are those described in Castello et al., Molc. Cell 63:696-710 (2016); Kovarik et al., Cytokine 89:21-26 (2017); Ray et al., Nature 499:172-177 (2013); Castello et al., Cell 149:1393-1406 (2012); Vlasova et al., Molc. Cell. 29:263-270 (2008); Barreau et al., Nucl. Acids Res. vol 33, doi:10.1093/nar/gki1012 (2006); Meisner et al., ChemBioChem 5:1432-1447 (2004); Guhaniyogi et al., Gene 265:11-23 (2001), all of which are incorporated by reference in their entirety for all purposes.

The RDE binding protein can be TTP which can bind to RDEs including for example, one or more of UUAUUUAUU (SEQ ID NO: 19) and AUUUA (SEQ ID NO: 8), or KSRP which binds AU-rich RDEs, or Aufl which binds RDEs including for example, one or more of UUGA (SEQ ID NO: 20), AGUUU (SEQ ID NO: 18), or GUUUG (SEQ ID NO: 12), or CELF-1 which binds RDEs including for example, one or more of UUGUU (SEQ ID NO: 10), or HuR which binds RDEs including for example, one or more of UUUAUUU (SEQ ID NO: 15), UUUUUUU (SEQ ID NO: 16), or UUUGUUU (SEQ ID NO: 13), or ESRP1 or ESRP2 which binds RDEs including for example, one or more of UGGGGAU (SEQ ID NO: 21), or ELAV which binds RDEs including for example, one or more of UUUGUUU (SEQ ID NO: 13). The RDE binding protein can be an enzyme involved in glycolysis, including for example, GAPDH which binds AU rich elements including for example, one or more of AUUUA (SEQ ID NO: 8) elements, or ENO3/ENO1 which binds RDEs including for example, one or more of CUGCUGCUG (SEQ ID NO: 22), or ALDOA which binds RDEs including for example, one or more of AUUGA (SEQ ID NO: 23).

Some RNA binding proteins increase the rate of RNA degradation after binding to the RDE. Some RNA binding proteins decrease the rate of degradation of the RNA after binding to the RDE. More than one RNA binding protein binds can bind to an RDE. In some RDE regulatory units, more than one RNA binding protein binds to more than one RDE. Binding of one or more of the RNA binding proteins to the one or more RDEs can increase the degradation rate of the RNA. Binding of one or more of the RNA binding proteins can decrease the degradation rate of the RNA. RNA binding proteins that increase degradation may compete for binding to an RDE with RNA binding proteins that decrease degradation, so that the stability of the RNA is dependent of the relative binding of the two RNA binding proteins. Other proteins can bind to the RDE binding proteins and modulate the effect of the RNA binding protein on the RNA with the RDE. Binding of a protein to the RNA binding protein can increases RNA stability or decrease RNA stability. An RNA can have multiple RDEs that are bound by the proteins HuR and TTP. The HuR protein can stabilize the RNA and the TTP protein can destabilize the RNA. An RNA can have at least one RDE that interacts with the proteins KSRP, TTP and/or HuR. KSRP can destabilize the RNA and compete for binding with the HuR protein that can stabilize the RNA. The KSRP protein can bind to the RDE and destabilizes the RNA and the TTP protein can bind to KSRP and prevent degradation of the RNA. Different proteins may be bound to the same transcript and may have competing effects on degradation and stabilization rates. Different proteins may be bound to the same transcript and may have cooperative effects on degradation and stabilization rates. Different proteins may be bound to the same transcript at different times, conferring different effects on degradation and stabilization.

The RDE can be a Class II AU rich element, and the RNA binding protein can be GAPDH. The Class II AU rich element bound by GAPDH can be AUUUAUUUAUUUA (SEQ ID NO: 9). The Class II AU rich element and GADPH can be used to control the expression of a transgene, a CAR, Smart CAR, DE-CAR, Smart-DE-CAR, and/or Side-CAR. The Class II AU rich element and GADPH also can be used to effect the expression of a transgene, CAR, Smart CAR, DE-CAR, Smart-DE-CAR, and/or Side-CAR in a T-lymphocyte. The Class II AU rich element and GADPH can be used to effect the expression of a transgene, CAR, Smart CAR, DE-CAR, Smart-DE-CAR, and/or Side-CAR in a CD8+ T-lymphocyte. The Class II AU rich element and GADPH can be used to effect the expression of a transgene, CAR, Smart CAR, DE-CAR, Smart-DE-CAR, and/or Side-CAR in a CD4+ T-lymphocyte. The Class II AU rich element and GADPH can be used to effect the expression of a transgene, CAR, Smart CAR, DE-CAR, Smart-DE-CAR, and/or Side-CAR in a natural killer cell.

The RDE may have microRNA binding sites. The RDE can be engineered to remove one or more of these microRNA binding sites. The removal of the microRNA binding sites can increase the on expression from a construct with an RDE by at least 5, 10, 15, 20, 50 or 100 fold. The RDE with the microRNA sites can be an RDE that is bound by GAPDH. The removal of microRNA sites from the RDE bound by GAPDH can increase the on expression of a construct with the GAPDH sensitive RDE by at least 5-10 fold. This GAPDH control through the RDE can be used to deliver a payload at a target site. The GAPDH control can be tied to activation of the eukaryotic cell by a CAR that recognizes an antigen found preferentially at the target site.

The RDE can be the 3'-UTR of IL-2 or IFN-γ, and removal of micro-RNA sites can increase the rate of expression and/or the dynamic range of expression from a transgene RNA with the RDE. The RDE can be the 3'-UTR of IL-2 and the removed micro-RNA sites can be the MIR-186 sites which deletion increases the kinetics of expression and increases the dynamic range of expression by about 50-fold. The RDE also can be the 3'-UTR of IFN-γ and the microRNA sites removed can be the MIR-125 sites.

Chimeric Antigen Receptors

Chimeric antigen receptors (CARs) can be fused proteins comprising an extracellular antigen-binding/recognition element, a transmembrane element that anchors the receptor to the cell membrane and at least one intracellular element. These CAR elements are known in the art, for example as described in patent application US20140242701, which is incorporated by reference in its entirety for all purposes herein. The CAR can be a recombinant polypeptide expressed from a construct comprising at least an extracellular antigen binding element, a transmembrane element and an intracellular signaling element comprising a functional signaling element derived from a stimulatory molecule. The stimulatory molecule can be the zeta chain associated with the T cell receptor complex. The cytoplasmic signaling element may further comprise one or more functional signaling elements derived from at least one costimulatory molecule. The costimulatory molecule can be chosen from 4-1BB (i.e., CD137), CD27 and/or CD28. The CAR may be a chimeric fusion protein comprising an extracellular antigen recognition element, a transmembrane element and an intracellular signaling element comprising a functional signaling element derived from a stimulatory molecule. The CAR may comprise a chimeric fusion protein comprising an extracellular antigen recognition element, a transmembrane element and an intracellular signaling element comprising a functional signaling element derived from a co-stimulatory molecule and a functional signaling element derived from a stimulatory molecule. The CAR may be a chimeric fusion protein comprising an extracellular antigen recognition element, a transmembrane element and an intracellular signaling element comprising two functional signaling elements derived from one or more co-stimulatory molecule(s) and a functional signaling element derived from a stimulatory molecule. The CAR may comprise a chimeric fusion protein comprising an extracellular antigen recognition element, a transmembrane element and an intracellular signaling element comprising at least two functional signaling elements derived from one or more co-stimulatory molecule(s) and a functional signaling element derived from a stimulatory molecule. The CAR may comprise an optional leader sequence at the amino-terminus (N-term) of the CAR fusion protein. The CAR may further comprise a leader sequence at the N-terminus of the extracellular antigen recognition element, wherein the leader sequence is optionally cleaved from the antigen recognition element (e.g., a scFv) during cellular processing and localization of the CAR to the cellular membrane.

Chimeric Antigen Receptor—Extracellular Element

Exemplary extracellular elements useful in making CARs are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The extracellular element(s) can be obtained from the repertoire of antibodies obtained from the immune cells of a subject that has become immune to a disease, such as for example, as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The extracellular element may be obtained from any of the wide variety of extracellular elements or secreted proteins associated with ligand binding and/or signal transduction as described in U.S. patent application Ser. No. 15/070,352 filed on Mar. 15, 2016, U.S. patent application Ser. No. 15/369,132 filed Dec. 5, 2016, U.S. Pat. Nos. 5,359,046, 5,686,281 and U.S. Pat. No. 6,103,521, all of which are incorporated by reference in their entirety for all purposes.

As described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes, there is provided a Smart CAR, DE-CAR, RDE-CAR, Smart-DE-CAR, Smart-RDE-CAR, DE-RDE-CAR, Smart-DE-RDE-CAR, and/or Side-CAR capable of binding to an antigens derived from viruses, infectious diseases, bacteria, tumor associated antigens, inflammatory disease associated antigens, antigens associated with neuronal disorders, antigens associated with diabetes, antigens associated with senescent cells, antigens associated with cardiovascular diseases, antigens associated with autoimmune diseases, and/or antigens associated with allergies. Examples of antigens useful for these applications are found, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Intracellular Element

The intracellular element can be a molecule that can transmit a signal into a cell when the extracellular element of the Smart CAR, DE-CAR, RDE-CAR, Smart-DE-CAR, Smart-RDE-CAR, DE-RDE-CAR, Smart-DE-RDE-CAR, and/or Side-CAR binds to (interacts with) an antigen. The intracellular signaling element can be generally responsible for activation of at least one of the normal effector functions of the immune cell in which the Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) has been introduced. The term "effector function" refers to a specialized function of a cell. Effector function of a T cell, for example, may be cytolytic activity or helper activity including the secretion of cytokines. Thus the term "intracellular signaling element" refers to the portion of a protein which transduces the effector function signal and directs the cell to perform a specialized function. While the entire intracellular signaling domain can be employed, in many cases the intracellular element or intracellular signaling element need not consist of the entire domain. To the extent that a truncated portion of the intracellular signaling domain is used, such truncated portion may be used as long as it transduces the effector function signal. The term intracellular signaling element is thus also meant to include any truncated portion of the intracellular signaling domain sufficient to transduce the effector function signal. Examples of intracellular signaling elements for use in the Smart CAR, DE-CAR, RDE-CAR, Smart-DE-CAR, Smart-RDE-CAR, DE-RDE-CAR, Smart-DE-RDE-CAR, and/or Side-CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

Intracellular elements and combinations of polypeptides useful with or as intracellular elements are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Transmembrane Element and Spacer Element

The Smart CAR, DE-CAR, RDE-CAR, Smart-DE-CAR, Smart-RDE-CAR, DE-RDE-CAR, Smart-DE-RDE-CAR, and/or Side-CAR may comprise a transmembrane element. The transmembrane element can be attached to the extracellular element of the Smart CAR, DE-CAR, RDE-CAR, Smart-DE-CAR, Smart-RDE-CAR, DE-RDE-CAR, Smart-DE-RDE-CAR, and/or Side-CAR. The transmembrane element can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). The transmembrane element can be associated with one of the other elements used in the Smart CAR, DE-CAR, RDE-CAR, Smart-DE-CAR, Smart-RDE-CAR, DE-RDE-CAR, Smart-DE-RDE-CAR, and/or Side-CAR. The transmembrane element can be selected or modified by amino acid substitution to avoid binding of such elements to the transmembrane elements of the same or different surface membrane proteins, e.g., to minimize interactions with other members of the receptor complex. The transmembrane element can be capable of homodimerization with another Smart CAR, DE-CAR, RDE-CAR, Smart-DE-CAR, Smart-RDE-CAR, DE-RDE-CAR, Smart-DE-RDE-CAR, and/or Side-CAR on the cell surface. The amino acid sequence of the transmembrane element may be modified or substituted so as to minimize interactions with the binding elements of the native binding partner present in the same cell.

The transmembrane element may be contributed by the protein contributing the multispecific extracellular inducer clustering element, the protein contributing the effector function signaling element, the protein contributing the proliferation signaling portion, or by a totally different protein. For the most part it will be convenient to have the transmembrane element naturally associated with one of the elements. In some cases it will be desirable to employ the transmembrane element of the ζ, η or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. The transmembrane element can be selected or modified by amino acid substitution to avoid binding of such elements to the transmembrane elements of the same or different surface membrane proteins to minimize interactions with other members of the receptor complex. The transmembrane element of ζ, η, FcεR1-γ and -β, MB1 (Igα), B29 or CD3-γ, or ζ, or ε, may be used in order to retain physical association with other members of the receptor complex.

Transmembrane elements useful in the present invention are described, fore example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Chimeric Antigen Receptors Coupled with Destabilizing Elements (DE-CAR)

Destabilizing elements, as described above, can be combined in cis with a CAR, as described above, so that the amount of the CAR polypeptide in the eukaryotic cell is under the control of the DE. DE-CARs, selection of DEs, and use of one or multiple DEs is described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Chimeric Antigen Receptors: Side-CARs

The CARs, Smart CARs, DE-CARs, RDE-CARs, Smart-RDE-CARs, DE-RDE-CARs, Smart-DE-CARs, and/or Smart-DE-RDE-CARs can be comprised of at least two parts which associate to form a functional CAR or DE-CAR. The extracellular antigen binding element can be expressed as a separate part from the transmembrane element, optional spacer, and the intracellular element of a CAR. The separate extracellular binding element can be associated with the host cell membrane (through a means other than a transmembrane polypeptide). The intracellular element can be expressed as a separate part from the extracellular element, transmembrane element, and optionally the spacer. The extracellular element and intracellular element can be expressed separately and each can have a transmembrane element, and optionally a spacer. Each part of the CAR or DE-CAR can have an association element ("Side-CAR") for bringing the two parts together to form a functional CAR or DE-CAR.

Side CARs, selection of Side CARs, and their use with or without a tether are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Lymphocyte Expansion Molecule and Other Regulatory Factors

The use of DEs, RDEs, and/or RNA control devices to control expression of lymphocyte expansion molecule ("LEM"), IL1, IL2, IL4, IL5, IL6, IL7, IL10, IL12, IL15, GM-CSF, G-CSF, TNFα, and/or IFNγ is described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Dominant Negative Regulators as CAR Off-Switches

A control device may regulate the expression of a polypeptide that inhibits or reduces the ability of a CAR to activate a T-lymphocyte or natural killer cell. This polypeptide can inhibit or reduce CAR activation, such as, for example, a mutant of ZAP-70 that has a dominant-negative effect when expressed in T-lymphocytes. Such ZAP-70 mutant can be a $\Delta$277-619 (leaving residues 1-276), Y319F, or K369A mutant of ZAP-70.

In some aspects, dominant-negative mutants are used to turn off signaling from an activated CAR at desired times. The dominant-negative mutants are polypeptides that disrupt the intracellular signaling from an activated CAR. Dominant-negative mutants can be used from polypeptides from or that interact with the signaling cascade activated by the CAR. Such mutants may interact with some signaling components but are defective for propagating the signal from the CAR and so prevent further activation of the host cell by the CAR. The dominant-negative mutant can be derived from the ZAP 70 protein. The dominant-negative mutant may be a $\Delta$277-619 (leaving residues 1-276) of ZAP 70, Y319F of ZAP 70, or K369A of ZAP 70.

The expression of the dominant-negative mutant can be under the inducible control of an RNA control device, an RDE, a destabilizing element (DE), and/or an inducible promoter. This inducible control allows expression of the dominant-negative mutant at a desired time allowing this construct to act as an off switch for a CAR eukaryotic cell. At a desired time, the dominant-negative mutant is expressed in response to the inducing stimulus, and the dominant-negative mutant turns off signaling from the CAR, DE-CAR and/or Side-CAR.

A Tet RNA control device or a (6R)-folinic acid RNA control device as described above can be used to control the expression of a dominant-negative mutant of ZAP 70 (e.g., a $\Delta$277-619 (leaving residues 1-276) mutant of Zap 70, Y319F ZAP 70, or K369A of ZAP 70). With these constructs, the dominant-negative mutant of Zap 70 can be expressed in a host cell upon addition of tetracycline or (6R)-folinic acid to the media. This tetracycline or (6R)-folinic acid RNA control device provides an off-switch for CAR activity that is inducible by tetracycline or (6R)-folinic acid.

The dominant-negative mutant of ZAP-70 can be placed under the control of a suitable RDE, DE, RNA control device, or Side-CAR. The RNA control device can be a Tet or (6R)-folinic acid reactive RNA control device so that when control device ligand (e.g., Tet or (6R)-folinic acid) is introduced the dominant-negative ZAP-70 mutant is expressed, and the expression of the ZAP-70 mutant inhibits activation of the T-lymphocyte by the CAR. The ZAP-70 mutant can act as an off-switch for the T-lymphocyte that is under the control of the Tet control device.

Receptors

CARs may be used as the receptor with the cell and the RDE-transgene. CARs are described above. In addition to CARs, other receptors may be used to activate or otherwise change conditions in a cell so that a transgene under the control of an RDE is expressed. Receptors that recognize and respond to a chemical signal can be coupled to expression of the transgene through the RDE. For example, ion channel-linked (ionotropic) receptors, G protein-linked (metabotropic) receptors, and enzyme-linked receptors can be coupled to the expression of the transgene.

One class of receptor that can be coupled to transgene expression are immune receptors such as, for example, T-cell receptors, B-cell receptors (aka antigen receptor or immunoglobulin receptor), and innate immunity receptors.

T-cell receptors are heterodimers of two different polypeptide chains. In humans, most T cells have a T-cell receptor made of an alpha (α) chain and a beta (β) chain have a T-cell receptor made of gamma and delta (γ/δ) chains (encoded by TRG and TRD, respectively). Techniques and primers for amplifying nucleic acids encoding the T-cell receptor chains from lymphocytes are well known in the art and are described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. The TCR repertoires can be used as separate chains to form an antigen binding domain. The TCR repertoires can be converted to single chain antigen binding domains. Single chain TCRs can be made from nucleic acids encoding human alpha and beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/Aggen_David.pdf?sequence=1, all of which are incorporated by reference in their entirety for all purposes.

B-cell receptors include an immunoglobulin that is membrane bound, a signal transduction moiety, CD79, and an ITAM. Techniques and primers for amplifying nucleic acids encoding human antibody light and heavy chains are well-known in the art, and described in, for example, ProGen's Human IgG and IgM Library Primer Set, Catalog No. F2000; Andris-Widhopf et al., "Generation of Human Fab Antibody Libraries: PCR Amplification and Assembly of Light and Heavy Chain Coding Sequences," Cold Spring Harb. Protoc. 2011; Lim et al., Nat. Biotechnol. 31:108-117 (2010); Sun et al., World J. Microbiol. Biotechnol. 28:381-386 (2012); Coronella et al., Nucl. Acids. Res. 28:e85 (2000), all of which are incorporated by reference in their entirety for all purposes. Techniques and primers for amplifying nucleic acids encoding mouse antibody light and heavy chains are well-known in the art, and described in, for example, U.S. Pat. No. 8,143,007; Wang et al., BMC Bioinform. 7(Suppl):S9 (2006), both of which are incorporated by reference in their entirety for all purposes. The antibody repertoires can be used as separate chains in antigen binding domains, or converted to single chain antigen binding domains. Single chain antibodies can be made from nucleic acids encoding human light and heavy chains using techniques well-known in the art including, for example, those described in Pansri et al., BMC Biotechnol. 9:6 (2009); Peraldi-Roux, Methods Molc. Biol. 907:73-83 (2012), both of which are incorporated by reference in their entirety for all purposes. Single chain antibodies can be made from nucleic acids encoding mouse light and heavy chains using techniques well-known in the art including, for example, those described in Imai et al., Biol. Pharm. Bull. 29:1325-1330 (2006); Cheng et al., PLoS ONE 6:e27406 (2011), both of which are incorporated by reference in their entirety for all purposes.

Innate immunity receptors include, for example, the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105).

G-protein linked receptors also known as seven-transmembrane domain receptors are a large family of receptors that couple receptor binding of ligand to cellular responses through G proteins. These G-proteins are trimers of α, β, and γ subunits (known as Gα, Gβ, and Gγ, respectively) which are active when bound to GTP and inactive when bound to GDP. When the receptor binds ligand it undergoes a conformational change and allosterically activates the G-protein to exchange GTP for bound GDP. After GTP binding the G-protein dissociates from the receptor to yield a Gα-GTP monomer and a Gβγ dimer. G-protein linked receptors have been grouped together into classes which include, for example, Rhodopsin-like receptors, secretin receptors, metabotropic glutamate/pheromone receptors, fungal mating pheromone receptors, cyclic AMP receptors, and frizzled/smoothened receptors. G-protein receptors are used in a wide variety of physiological processes including detection of electromagnetic radiation, gustatory sense (taste), sense of smell, neurotransmission, immune system regulation, growth, cell density sensing, etc.

Enzyme linked receptors also known as a catalytic receptor, is a transmembrane receptor, where the binding of an extracellular ligand causes enzymatic activity on the intracellular side. Enzyme linked receptors have two domains joined together by a transmembrane portion (or domain) of the polypeptide. The two terminal domains are an extracellular ligand binding domain and an intracellular domain that has a catalytic function. There are multiple families of enzyme linked receptors including, for example, the Erb receptor family, the glial cell-derived neurotrophic factor receptor family, the natriuretic peptide receptor family, the trk neurotrophin receptor family, and the toll-like receptor family.

Ion channel linked receptors also known as ligand-gated ion channels are receptors that allow ions such as, for example, $Na^+$, $K^+$, $Ca^{2+}$ and $Cl^-$ to pass through the membrane in response to the binding of a ligand to the receptor. There are multiple families of ligand-gated ion channels including, for example, cationic cys-loop receptors, anionic cys-loop receptors, ionotropic glutamate receptors (AMPA receptors, NMDA receptors), GABA receptors, 5-HT receptors, ATP-gated channels, and $PIP_2$-gated channels.

Eukaryotic Cells

Various eukaryotic cells can be used as the eukaryotic cell of the invention. The eukaryotic cells can be animal cells. The eukaryotic cells can be mammalian cells, such as mouse, rat, rabbit, hamster, porcine, bovine, feline, or canine. The mammalian cells can be cells of primates, including but not limited to, monkeys, chimpanzees, gorillas, and humans. The mammalians cells can be mouse cells, as mice routinely function as a model for other mammals, most particularly for humans (see, e.g., Hanna, J. et al., Science 318:1920-23, 2007; Holtzman, D. M. et al., J Clin Invest. 103(6):R15-R21, 1999; Warren, R. S. et al., J Clin Invest. 95: 1789-1797, 1995; each publication is incorporated by reference in its entirety for all purposes). Animal cells include, for example, fibroblasts, epithelial cells (e.g., renal, mammary, prostate, lung), keratinocytes, hepatocytes, adipocytes, endothelial cells, and hematopoietic cells. The animal cells can be adult cells (e.g., terminally differentiated, dividing or non-dividing) or embryonic cells (e.g., blastocyst cells, etc.) or stem cells. The eukaryotic cell also can be a cell line derived from an animal or other source.

The eukaryotic cells can be stem cells. A variety of stem cells types are known in the art and can be used as the eukaryotic cell, including for example, embryonic stem cells, inducible pluripotent stem cells, hematopoietic stem cells, neural stem cells, epidermal neural crest stem cells, mammary stem cells, intestinal stem cells, mesenchymal stem cells, olfactory adult stem cells, testicular cells, and progenitor cells (e.g., neural, angioblast, osteoblast, chondroblast, pancreatic, epidermal, etc.). The stem cells can be stem cell lines derived from cells taken from a subject.

The eukaryotic cell can be a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells of the invention. The eukaryotic cell can be derived from any of these circulating eukaryotic cells. Transgenes may be used with any of these circulating cells or eukaryotic cells derived from the circulating cells. The eukaryotic cell can be a T-cell or T-cell precursor or progenitor cell. The eukaryotic cell can be a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. The eukaryotic cell can be a natural killer cell, or a precursor or progenitor cell to the natural killer cell. The eukaryotic cell can be a B-cell, or a B-cell precursor or progenitor cell. The eukaryotic cell can be a neutrophil or a neutrophil precursor or progenitor cell. The eukaryotic cell can be a megakaryocyte or a precursor or progenitor cell to the megakaryocyte. The eukaryotic cell can be a macrophage or a precursor or progenitor cell to a macrophage.

The eukaryotic cells can be plant cells. The plant cells can be cells of monocotyledonous or dicotyledonous plants, including, but not limited to, alfalfa, almonds, asparagus, avocado, banana, barley, bean, blackberry, brassicas, broccoli, cabbage, canola, carrot, cauliflower, celery, cherry, chicory, citrus, coffee, cotton, cucumber, eucalyptus, hemp, lettuce, lentil, maize, mango, melon, oat, papaya, pea, peanut, pineapple, plum, potato (including sweet potatoes), pumpkin, radish, rapeseed, raspberry, rice, rye, sorghum, soybean, spinach, strawberry, sugar beet, sugarcane, sunflower, tobacco, tomato, turnip, wheat, zucchini, and other fruiting vegetables (e.g. tomatoes, pepper, chili, eggplant, cucumber, squash etc.), other bulb vegetables (e.g., garlic, onion, leek etc.), other pome fruit (e.g. apples, pears etc.), other stone fruit (e.g., peach, nectarine, apricot, pears, plums etc.), Arabidopsis, woody plants such as coniferous and deciduous trees, an ornamental plant, a perennial grass, a forage crop, flowers, other vegetables, other fruits, other agricultural crops, herbs, grass, or perennial plant parts (e.g., bulbs; tubers; roots; crowns; stems; stolons; tillers; shoots; cuttings, including un-rooted cuttings, rooted cuttings, and callus cuttings or callus-generated plantlets; apical meristems etc.). The term "plants" refers to all physical parts of a plant, including seeds, seedlings, saplings, roots, tubers, stems, stalks, foliage and fruits.

The eukaryotic cells also can be algal, including but not limited to algae of the genera Chlorella, Chlamydomonas, Scenedesmus, Isochrysis, Dunaliella, Tetraselmis, Nannochloropsis, or Prototheca. The eukaryotic cells can be fungi cells, including, but not limited to, fungi of the genera *Saccharomyces, Klyuveromyces, Candida, Pichia, Debaryomyces, Hansenula, Yarrowia, Zygosaccharomyces,* or *Schizosaccharomyces*.

The eukaryotic cells can be obtained from a subject. The subject may be any living organisms. The cells can be derived from cells obtained from a subject. Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. Any number of T cell lines available in the art also may be used. T-cells can be obtained from a unit of blood collected from a subject using any number of techniques known to the skilled artisan, such as Ficoll separation. Cells from the circulating blood of an individual can be obtained by apheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. The cells can be washed with phosphate buffered saline (PBS). In an alternative aspect, the wash solution lacks calcium and may lack magnesium or may lack many if not all divalent cations. Initial activation steps in the absence of calcium can lead to magnified activation.

Enrichment of a T cell population by negative selection can be accomplished with a combination of antibodies directed to surface markers unique to the negatively selected cells. Cells can be enriched by cell sorting and/or selection via negative magnetic immunoadherence or flow cytometry using a cocktail of monoclonal antibodies directed to cell surface markers present on the cells. For example, to enrich for CD4+ cells, a monoclonal antibody cocktail typically includes antibodies to CD14, CD20, CD11b, CD16, HLA-DR, and CD8. It may be desirable to enrich for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005, each of which is incorporated by reference in its entirety for all purposes.

NK cells may be expanded in the presence of a myeloid cell line that has been genetically modified to express membrane bound IL-15 and 4-1BB ligand (CD137L). A cell line modified in this way which does not have WIC class I and II molecules is highly susceptible to NK cell lysis and activates NK cells. For example, K562 myeloid cells can be transduced with a chimeric protein construct consisting of human IL-15 mature peptide fused to the signal peptide and transmembrane domain of human CD8a and GFP. Transduced cells can then be single-cell cloned by limiting dilution and a clone with the highest GFP expression and surface IL-15 selected. This clone can then be transduced with human CD137L, creating a K562-mb15-137L cell line. To preferentially expand NK cells, peripheral blood mononuclear cell cultures containing NK cells are cultured with a K562-mb15-137L cell line in the presence of 10 IU/mL of IL-2 for a period of time sufficient to activate and enrich for a population of NK cells. This period can range from 2 to 20 days, preferably about 5 days. Expanded NK cells may then be transduced with the anti-CD19-BB-ζ chimeric receptor.

Nucleic Acids

Also described in this disclosure are nucleic acids that encode, at least in part, the individual peptides, polypeptides, proteins, and RNA control devices described herein. The nucleic acids may be natural, synthetic or a combination thereof. The nucleic acids of the invention may be RNA, mRNA, DNA or cDNA.

The nucleic acids of the invention also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. An exemplary selection scheme can utilize a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

An example of a promoter that is capable of expressing a Smart CAR, DE-CAR, RDE-CAR, Smart-DE-CAR, Smart-RDE-CAR, DE-RDE-CAR, Smart-DE-RDE-CAR, and/or Side-CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention is not limited to the use of constitutive promoters.

Inducible or repressible promoters are also contemplated for use in this disclosure. Examples of inducible promoters include, but are not limited to a Nuclear Factor of Activated T-cell inducible promoter (NFAT), a metallothionein promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Macian et al., Oncogene 20:2476-2489 (2001); Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822,754, 8,748,125, 8,536,354, all of which are incorporated by reference in their entirety for all purposes.

Expression vectors typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

The expression vector may be a bi-cistronic construct or multiple cistronic construct. The two cistrons may be oriented in opposite directions with the control regions for the cistrons located in between the two cistrons. When the construct has more than two cistrons, the cistrons may be arranged in two groups with the two groups oriented in opposite directions for transcription. Exemplary bicistronic constructs are described in Amendola et al., Nat. Biotechnol. 23:108-116 (2005), which is incorporated by reference in its entirety for all purposes. The control region for one cistron may be capable of high transcription activity and the other may have low transcriptional activity under conditions of use. One or both control regions may be inducible. Examples of high transcription activity control regions include, for example, MND, EF1-alpha, PGK1, CMV, ubiquitin C, SV40 early promoter, tetracycline-responsive element promoter, cell-specific promoters, human beat-actin promoter, and CBG (chicken beta-globin), optionally including the CMV early enhancer. Examples of low transcription activity control regions include, for example, TRE3G (commercially sold by Clontech, a tetracycline-responsive element promoter with mutations that reduce basal expression), T-REx™ (commercially sold by Thermo-Fisher), and a minimal TATA promoter (Kiran et al., Plant Physiol. 142:364-376 (2006), which is incorporated by reference in its entirety for all purposes), HSP68, and a minimal CMV promoter. Examples of inducible control regions include, for example, NFAT control regions (Macian et al, Oncogene 20:2476-2489 (2001)), and the inducible control regions described above.

The bi-cistronic construct may encode a CAR and a polypeptide that is a payload (or makes a payload) to be delivered at a target site. Exemplary payloads are described above and below. The nucleic acid encoding the CAR can be operably linked to a strong promoter, a weak promoter, and/or an inducible promoter, and optionally, operably linked to a RNA control device, DE, RDE, or combination of the foregoing. The CAR can be encoded by nucleic acids in a Side-CAR format. The nucleic acid encoding the polypeptide can be operably linked to a strong promoter, a weak promoter, and/or an inducible promoter. The nucleic acid encoding the polypeptide that is a payload (or makes the payload) can be under the control of an RDE. The RDE may be one that responds to the activation state of the cell through, for example, glycolytic enzymes such as, for example, glyceraldehyde phosphate dehydrogenase (GAPDH), enolase (ENO1 or ENO3), phosphoglycerate kinase (PGK1), triose phosphate isomerase (TPI1), aldolase A (ALDOA), or phosphoglycerate mutase (PGAM1). The RDE may also be bound and regulated by other energy metabolism enzymes such as, for example, transketolase (TKT), malate dehydrogenase (MDH2), succinyl CoA Synthetase (SUGLG1), ATP citrate lyase (ACLY), or isocitrate dehydrogenase (IDH1/2). The host cell can express a CAR that binds to its antigen at a target site in a subject. This binding of antigen at the target site activates the cell causing the cell to increase glycolysis which induces expression of the nucleic acid encoding the polypeptide under the control of the RDE (bound by glycolytic or other energy metabolism enzymes).

The multicistronic constructs can have three or more cistrons with each having control regions (optionally inducible) and RDEs operably linked to some or all of the transgenes. These cassettes may be organized into two groups that are transcribed in opposite directions on the construct. Two or more transgenes can be transcribed from the same control region and the two or more transgenes may have IRES (internal ribosome entry site) sequences operably linked to the downstream transgenes. Alternatively, the two or more transgenes are operably linked together by 2A elements as described in Plasmids 101: Multicistronic Vectors found at blog.addgene.org/plasmids-101-multicistrnic-vectors. Commonly used 2A sequences include, for example, EGRGSLLTCGDVEENPGP (T2A) (SEQ ID NO: 24), ATNFSLLKQAGDVEENPGP (P2A) (SEQ ID NO: 25); QC_TNYALLKLAGDVESNPGP (E2A) (SEQ ID NO: 26); and VKQTLNFDLLKLAGDVESNPGP (F2A) (SEQ ID NO: 27) all of which can optionally include the sequence GSG at the amino terminal end. This allows multiple transgenes to be transcribed onto a single transcript that is regulated by a 3'-UTR with an RDE (or multiple RDEs).

The bicistronic/multicistronic vector can increase the overall expression of the two or more cistrons (versus introducing the cistrons on separate constructs). The bicistronic/multicistronic construct can be derived from a lentivirus vector. The bicistronic/multicistronic construct can encode a CAR and a polypeptide(s) that is encoded on a transgene(s) (e.g., a payload), and the bicistronic construct may increase expression of the polypeptide encoded by the transgene(s) when the cell is activated by the CAR.

It may be desirable to modify polypeptides described herein. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, *Gene* 8:81-97, 1979; Roberts et al., *Nature* 328:731-734, 1987, which is incorporated by reference in its entirety for all purposes). The recombinant nucleic acids encoding the polypeptides of the invention can be modified to provide preferred codons which enhance translation of the nucleic acid in a selected organism.

The polynucleotides can also include polynucleotides including nucleotide sequences that are substantially equivalent to other polynucleotides described herein. Polynucleotides can have at least about 80%, more typically at least about 90%, and even more typically at least about 95%, sequence identity to another polynucleotide. The nucleic acids also provide the complement of the polynucleotides including a nucleotide sequence that has at least about 80%, more typically at least about 90%, and even more typically at least about 95%, sequence identity to a polynucleotide encoding a polypeptide recited herein. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., *Angew Chem Intl Ed.* 28:716-34, 1989 (which is incorporated by reference in its entirety for all purposes), may also be used to prepare such nucleic acids.

Amino acid "substitutions" for creating variants are preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Also disclosed herein are nucleic acids encoding Smart CAR, DE-CAR, RDE-CAR, Smart-DE-CAR, Smart-RDE-CAR, DE-RDE-CAR, Smart-DE-RDE-CAR, and/or Side-CARs. The nucleic acid encoding the Smart CAR, DE-CAR, RDE-CAR, Smart-DE-CAR, Smart-RDE-CAR, DE-RDE-CAR, Smart-DE-RDE-CAR, and/or Side-CAR can be easily prepared from an amino acid sequence of the specified CAR combined with the sequence of the RNA control device by a conventional method. A base sequence encoding an amino acid sequence can be obtained from the aforementioned NCBI RefSeq IDs or accession numbers of GenBenk for an amino acid sequence of each element, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acids can be linked to another nucleic acid so as to be expressed under control of a suitable promoter. The nucleic acid can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

When the nucleic acid is introduced into a cell ex vivo, the nucleic acid of may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful. Particularly, a composition in a form suitable for administration to a living body which contains the nucleic acid of the present invention carried by a suitable vector is suitable for in vivo gene therapy.

Introducing Nucleic Acids into Eukaryotic Cells

A process for producing a cell expressing the Smart CAR, DE-CAR, RDE-CAR, Smart-DE-CAR, Smart-RDE-CAR, DE-RDE-CAR, Smart-DE-RDE-CAR, Side-CAR, and/or a transgene operably linked to an RDE(s) includes a step of introducing the nucleic acid encoding a Smart CAR, DE-CAR, RDE-CAR, Smart-DE-CAR, Smart-RDE-CAR, DE-RDE-CAR, Smart-DE-RDE-CAR, Side-CAR, and/or transgene-RDE described herein into a eukaryotic cell. This step can be carried out ex vivo. For example, a cell can be transformed ex vivo with a virus vector or a non-virus vector carrying the nucleic acid described herein to produce a cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE.

In a process, a eukaryotic cell as describe above can be used. The eukaryotic cell can be derived from a mammal, for example, a human cell, or a cell derived from a non-human mammal such as a monkey, a mouse, a rat, a pig, a horse, or a dog can be used. The cell used in the process is not particularly limited, and any cell can be used. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell, a dendritic cell, a B cell, a hematopoietic stem cell, a macrophage, a monocyte, a NK cell or a hematopoietic cell, an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present invention, particularly, use of a T cell, a precursor cell of a T cell (a hematopoietic stem cell, a lymphocyte precursor cell etc.) or a cell population containing them is preferable. Examples of the T cell include a CD8-positive T cell, a CD4-positive T cell, a regulatory T cell, a cytotoxic T cell, and a tumor infiltrating lymphocyte. The cell population containing a T cell and a precursor cell of a T cell includes a PBMC. The aforementioned cells may be collected from a living body, obtained by expansion culture of a cell collected from a living body, or established as a cell strain. When transplantation of the produced Smart CAR, DE-CAR, RDE-CAR, Smart-DE-CAR, Smart-RDE-CAR, DE-RDE-CAR, Smart-DE-RDE-CAR, Side-CAR, and/or transgene-RDE expressing cell or a cell differentiated from the produced Smart CAR, DE-CAR, RDE-CAR, Smart-DE-CAR, Smart-RDE-CAR, DE-RDE-CAR, Smart-DE-RDE-CAR, Side-CAR, and/or transgene-RDE expressing cell into a living body is desired, it is preferable to introduce the nucleic acid into a cell collected from the living body itself.

The nucleic acid encoding the Smart CAR, DE-CAR, RDE-CAR, Smart-DE-CAR, Smart-RDE-CAR, DE-RDE-CAR, Smart-DE-RDE-CAR, Side-CAR, and/or transgene-RDE is inserted into a vector, and the vector is introduced into a cell. The nucleic acid encoding the Smart CAR, DE-CAR, RDE-CAR, Smart-DE-CAR, Smart-RDE-CAR, DE-RDE-CAR, Smart-DE-RDE-CAR, Side-CAR, and/or transgene-RDE is introduced to the eukaryotic cell by transfection (e.g., Gorman, et al. Proc. Nati. Acad. Sci. 79.22 (1982): 6777-6781, which is incorporated by reference in its entirety for all purposes), transduction (e.g., Cepko and Pear (2001) Current Protocols in Molecular Biology unit 9.9; DOI: 10.1002/0471142727.mb0909s36, which is incorporated by reference in its entirety for all purposes), calcium phosphate transformation (e.g., Kingston, Chen and Okayama (2001) Current Protocols in Molecular Biology Appendix 1C; DOI: 10.1002/0471142301.nsa01cs01, which is incorporated by reference in its entirety for all purposes), cell-penetrating peptides (e.g., Copolovici, Langel, Eriste, and Langel (2014) ACS Nano 2014 8 (3), 1972-1994; DOI: 10.1021/nn4057269, which is incorporated by reference in its entirety for all purposes), electroporation (e.g Potter (2001) Current Protocols in Molecular Biology unit 10.15; DOI: 10.1002/0471142735.im1015s03 and Kim et al (2014) Genome 1012-19. doi:10.1101/gr.171322.113, Kim et al. 2014 describe the Amaza Nucleofector, an optimized electroporation system, both of these references are incorporated by reference in their entirety for ail purposes), microinjection (e.g., McNeil (2001) Current Protocols in Cell Biology unit 20.1; DOI: 10.1002/0471143030.cb2001s18, which is incorporated by reference in its entirety for all purposes), liposome or cell fusion (e.g., Hawley-Nelson and Ciccarone (2001) Current Protocols in Neuroscience Appendix 1F; DOI: 10.1002/0471142301.nsa01fs10, which is incorporated by reference in its entirety for all purposes), mechanical manipulation (e.g. Sharon et al. (2013) PNAS 2013 110(6); DOI: 10.1073/pnas.1218705110, which is incorporated by reference in its entirety for all purposes) or other well-known technique for delivery of nucleic acids to eukaryotic cells. Once introduced, Smart CAR, DE-CAR, RDE-CAR, Smart-DE-CAR, Smart-RDE-CAR, DE-RDE-CAR, Smart-DE-RDE-CAR, Side-CAR, and/or transgene-RDE nucleic acid can be transiently expressed episomally, or can be integrated into the genome of the eukaryotic cell using well known techniques such as recombination (e.g., Lisby and Rothstein (2015) Cold Spring Harb Perspect Biol. March 2; 7(3). pii: a016535. doi: 10.1101/cshperspect.a016535, which is incorporated by reference in its entirety for all purposes), or non-homologous integration (e.g., Deyle and Russell (2009) Curr Opin Mol Ther. 2009 August; 11(4):442-7, which is incorporated by reference in its entirety for all purposes). The efficiency of homologous and non-homologous recombination can be facilitated by genome editing technologies that introduce targeted double-stranded breaks (DSB). Examples of DSB-generating technologies are CRISPR/Cas9, TALEN, Zinc-Finger Nuclease, or equivalent systems (e.g., Cong et al. Science 339.6121 (2013): 819-823, Li et al. *Nucl. Acids Res* (2011): gkr188, Gaj et al. Trends in Biotechnology 31.7 (2013): 397-405, all of which are incorporated by reference in their entirety for all purposes), transposons such as Sleeping Beauty (e.g., Singh et al (2014) Immunol Rev. 2014 January; 257(1):181-90. doi: 10.1111/imr.12137, which is incorporated by reference in its entirety for all purposes), targeted recombination using, for example, FLP recombinase (e.g., O'Gorman, Fox and Wahl Science (1991) 15:251(4999):1351-1355, which is incorporated by reference in its entirety for all purposes), CRE-LOX (e.g., Sauer and Henderson PNAS (1988): 85; 5166-5170), or equivalent systems, or other techniques known in the art for integrating the nucleic acid encoding the Smart CAR, DE-CAR, Smart-DE-CAR, and/or Side CAR into the eukaryotic cell genome.

The polynucleotide encoding the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be integrated into a chromosome of the eukaryotic cell. The polynucleotide encoding the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be present in the eukaryotic cell extrachromosomally. The polynucleotide encoding the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be integrated using a genome editing enzyme (CRISPR, TALEN, Zinc-Finger nuclease), and appropriate nucleic acids (including nucleic acids encoding the Smart CAR, DE-CAR, RDE-CAR, Smart-DE-CAR, Smart-RDE-CAR, DE-RDE-CAR, Smart-DE-RDE-CAR, Side-CAR, and/or transgene-RDE). The nucleic acid encoding the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be integrated into the eukaryotic cell chromosome at a genomic safe harbor site, such as, for example, the CCR5, AAVS1, human ROSA26, or PSIP1 loci. (Sadelain et al., Nature Rev. 12:51-58 (2012); Fadel et al., J. Virol. 88(17):9704-9717 (2014); Ye et al., PNAS 111(26):9591-9596 (2014), all of which are incorporated by reference in their entirety for all purposes.) The integration of the nucleic acid encoding the Smart CAR, DE-CAR, RDE-CAR, Smart-DE-CAR, Smart-RDE-CAR, DE-RDE-CAR, Smart-DE-RDE-CAR, Side-CAR, and/or transgene-RDE at the CCR5, PSIP1, or TRAC locus (T-cell receptor α constant locus) can be done using a gene editing system, such as, for example, CRISPR, TALEN, Sleeping Beauty Transposase, PiggyBac transposase, or Zinc-Finger nuclease systems. Eyquem et al., Nature 543:113-117 (2017), which is incorporated by reference in its entirety for all purposes. The eukaryotic cell can be a human, T-lymphocyte and a CRISPR system is used to integrate the Smart CAR, DE-CAR, RDE-CAR, Smart-DE-CAR, Smart-RDE-CAR, DE-RDE-CAR, Smart-DE-RDE-CAR, Side-CAR, and/or transgene-RDE at the CCR5 or PSIP1 locus. Integration of the nucleic acid at CCR5, PSIP1, or TRAC locus using the CRISPR system also may delete a portion, or all, of the CCR5 gene, PSIP1 gene, or TRAC locus. Cas9 in the eukaryotic cell may be derived from a plasmid encoding Cas9, an exogenous mRNA encoding Cas9, or recombinant Cas9 polypeptide alone or in a ribonucleoprotein complex. (Kim et al (2014) Genome 1012-19. doi:10.1101/gr.171322.113.; Wang et al (2013) Cell 153 (4). Elsevier Inc.: 910-18. doi:10.1016/j.cell.2013.04.025, both of which are incorporated by reference in their entirety for all purposes.)

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

Transduction can be done with a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. As the virus vector, a virus vector lacking the replicating ability so as not to self-replicate in an infected cell is preferably used.

When a retrovirus vector is used to transduce the host cell, the process can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+envAm-12 (U.S. Pat. No. 5,278,056, which is incorporated by reference in its entirety for all purposes), and Psi-Crip (Proceedings of the National Academy of Sciences of the United States of America, vol. 85, pp. 6460-6464 (1988), which is incorporated by reference in its entirety for all purposes). A retrovirus particle can also be prepared using a 293 cell or a T cell having high transfection efficiency. Many kinds of retrovirus vectors produced based on retroviruses and packaging cells that can be used for packaging of the retrovirus vectors are widely commercially available from many companies.

A number of viral based systems have been developed for gene transfer into mammalian cells. A selected gene can be inserted into a vector and packaged in viral particles using techniques known in the art. The recombinant virus can then be isolated and delivered to cells of the subject either in vivo or ex vivo. A number of viral systems are known in the art. Adenovirus vectors can be used. A number of adenovirus vectors are known in the art and can be used. In addition, lentivirus vectors can be used.

A viral vector derived from a RNA virus can be used to introduce to a cell Smart CAR, DE-CAR, RDE-CAR, Smart-DE-CAR, Smart-RDE-CAR, DE-RDE-CAR, Smart-DE-RDE-CAR, Side-CAR, and/or transgene-RDE encoding polynucleotides. The RNA virus vector can encode the reverse complement or antisense strand of the polynucleotide encoding the RNA control device and CAR construct (the complementary strand encodes the sense strand for the RNA control device, DE, RDE, CAR and/or Side-CAR construct). Thus, the RNA control device should not be active in the single stranded, RNA virus vector. The sense strand of the RNA virus construct encoding the RNA control device, DE, RDE, CAR, Side-CAR, and/or transgene can be used, and the viral vector with the RNA control device, DE, RDE, CAR and/or Side-CAR construct is maintained and replicated in the presence (or absence) of ligand for the sensor element of the RNA control device (or under conditions where the RDE is stable) to prevent cleavage of the RNA. The viral vector encoding the sense strand of the RNA control device, DE, RDE, CAR, Side-CAR, and/or transgene construct in the viral vector can then be maintained and replicated with (or without) ligand for the sensor element.

A non-virus vector can be used in combination with a liposome and a condensing agent such as a cationic lipid as described in WO 96/10038, WO 97/18185, WO 97/25329, WO 97/30170 and WO 97/31934 (which are incorporated herein by reference in their entirety for all purposes). The nucleic acid of the present invention can be introduced into a cell by calcium phosphate transduction, DEAE-dextran, electroporation, or particle bombardment.

Chemical structures with the ability to promote stability and/or translation efficiency can be used. The RNA preferably has 5' and 3' UTRs. The 5' UTR can be between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA. The 5' and 3' UTRs can be the naturally occurring, endogenous 5' and 3' UTRs for the nucleic acid of interest. The UTR sequences that are not endogenous to the nucleic acid of interest can be added by incorporating the UTR sequences into the forward and reverse primers or by other modification techniques applied to the template. The use of UTR sequences that are not endogenous to the nucleic acid of interest can be useful for modifying the stability and/or translation efficiency of the RNA. For example, it is known that AU-rich elements in 3'UTR sequences can decrease the stability of mRNA. Therefore, 3' UTRs can be selected or designed to increase the stability of the transcribed RNA based on properties of UTRs that are well known in the art.

The mRNA may have both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

In the step of introducing a nucleic acid into a cell, a functional substance for improving the introduction efficiency can also be used (e.g. WO 95/26200 and WO 00/01836, which are incorporated herein by reference in their entirety for all purposes). Examples of the substance for improving the introduction efficiency include a substance having ability to bind to a virus vector, for example, fibronectin and a fibronectin fragment. A fibronectin fragment can have a heparin binding site, for example, a fragment commercially available as RetroNetcin (registered trademark, CH-296, manufactured by TAKARA BIO INC.) can be used. Also, polybrene which is a synthetic polycation having an effect of improving the efficiency of infection of a retrovirus into a cell, a fibroblast growth factor, V type collagen, polylysine or DEAE-dextran can be used.

The functional substance can be immobilized on a suitable solid phase, for example, a container used for cell culture (plate, petri dish, flask or bag) or a carrier (microbeads etc.).

Eukaryotic Cells Expressing the Smart CAR, DE-CAR, RDE-CAR, Smart-DE-CAR, Smart-RDE-CAR, DE-RDE-CAR, Smart-DE-RDE-CAR, and/or Side-CAR The cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be cells in which a nucleic acid encoding a Smart CAR, DE-CAR, RDE-CAR, Smart-DE-CAR, Smart-RDE-CAR, DE-RDE-CAR, Smart-DE-RDE-CAR, Side-CAR, and/or transgene-RDE is introduced and expressed.

Eukaryotic cells can bind to a specific antigen via the CAR, DE-CAR, and/or Side-CAR polypeptide causing the CAR, DE-CAR, and/or Side-CAR polypeptide to transmit a signal into the eukaryotic cell, and as a result, the eukaryotic cell can be activated. The activation of the eukaryotic cell expressing the Smart CAR, DE-CAR, RDE-CAR, Smart-DE-CAR, Smart-RDE-CAR, DE-RDE-CAR, Smart-DE-RDE-CAR, and/or Side-CAR can be varied depending on the kind of a eukaryotic cell and the intracellular element of the Smart CAR, DE-CAR, RDE-CAR, Smart-DE-CAR, Smart-RDE-CAR, DE-RDE-CAR, Smart-DE-RDE-CAR, and/or Side-CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and/or a macrophage.

Eukaryotic cells expressing CAR, Smart CAR, DE-CAR, RDE-CAR, Smart-DE-CAR, Smart-RDE-CAR, DE-RDE-CAR, Smart-DE-RDE-CAR, and/or Side-CAR constructs can be detected using Protein L (a bacterial surface protein isolated from *Peptostreptoccocus magnus* that selectively binds to variable light chains (kappa chain) of immunoglobulins. Protein L can be directly labeled with a reporter (e.g., a light emitting or absorbing moiety) or can be labeled with an agent such as biotin. When biotin or related molecule is used to label the Protein L, binding of Protein L to eukaryotic cells displaying CAR, DE-CAR, and/or Side-CAR polypeptide can be detected by adding a streptavidin (or similar paired molecule) labeled with reporter (e.g., phycoerythrin). Zheng et al., J. Translational Med., 10:29 (2012), which is incorporated by reference in its entirety for all purposes. Protein L binding to eukaryotic cells containing CAR, Smart CAR, DE-CAR, RDE-CAR, Smart-DE-CAR, Smart-RDE-CAR, DE-RDE-CAR, Smart-DE-RDE-CAR, and/or Side-CAR constructs may show the presence of antibody light chain, the extracellular domain of a CAR, on the eukaryotic cell. This method of detecting CAR expression on the eukaryotic cell can also be used to quantitate the amount of CAR, DE-CAR, and/or Side-CAR polypeptide on the surface of the eukaryotic cell. Protein L can be used in QC and QA methodologies for making eukaryotic cells with the CAR, Smart CAR, DE-CAR, RDE-CAR, Smart-DE-CAR, Smart-RDE-CAR, DE-RDE-CAR, Smart-DE-RDE-CAR, and/or Side-CAR constructs.

A eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be used as a therapeutic agent to treat a disease. This therapeutic agent can comprise the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE as an active ingredient, and may further comprise a suitable excipient. Examples of the excipient include pharmaceutically acceptable excipients for the composition. The disease against which the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE is administered is not particularly limited as long as the disease shows sensitivity to the eukaryotic cell. Examples of diseases of the invention include a cancer (blood cancer (leukemia), solid tumor (ovarian cancer) etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis. An autoimmune disease (e.g., pemphigus vulgaris, lupus erythematosus, rheumatoid arthritis) can be treated with a eukaryotic cell expressing a Smart CAR, DE-CAR, RDE-CAR, Smart-DE-CAR, Smart-RDE-CAR, DE-RDE-CAR, Smart-DE-RDE-CAR, Side-CAR, and/or transgene-RDE that binds to the immune proteins that cause the autoimmune disease. For example, the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can target cells that make an antibody which causes the autoimmune disease. The eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE could target T-lymphocytes which cause the autoimmune disease.

Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be used as a therapeutic agent to treat an allergy. Such therapeutic agents can comprise the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE as an active ingredient, and may further comprise a suitable excipient. Examples of the excipient include pharmaceutically acceptable excipients for the composition. Examples of allergies that can be treated with the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE include, for example, allergies to pollen, animal dander, peanuts, other nuts, milk products, gluten, eggs, seafood, shellfish, and soy. The eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can target cells that make an antibody which causes the allergic reaction against, for example, pollen, animal dander, peanuts, other nuts, milk products, gluten, eggs, seafood, shellfish, and soy. The targeted cells can be one or more of B-cells, memory B-cells, plasma cells, pre-B-cells, and progenitor B-cells. The eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can target T-lymphocytes which cause the allergic reaction against, for example, pollen, animal dander, peanuts, other nuts, milk products, gluten, eggs, seafood, shellfish, and soy. The Smart CAR, DE-CAR, RDE-CAR, Smart-DE-CAR, Smart-RDE-CAR, DE-RDE-CAR, Smart-DE-RDE-CAR, Side-CAR, and/or transgene-RDE can bind to the idiotypic determinant of the antibody or T-cell receptor.

The eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be administered for treatment of a disease or condition. These eukaryotic cells can be utilized for prevention of an infectious disease after bone marrow transplantation or exposure to radiation, donor lymphocyte transfusion for the purpose of remission of recurrent leukemia, and the like. The therapeutic agent comprising the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be an active ingredient and can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

The eukaryotic cells with Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be characterized prior to administration to the subject. The eukaryotic cells with Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be tested to confirm Smart CAR, DE-CAR, RDE-CAR, Smart-DE-CAR, Smart-RDE-CAR, DE-RDE-CAR, Smart-DE-RDE-CAR, Side-CAR, and/or transgene-RDE expression. The eukaryotic cells with Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be exposed to a level of ligand(s) that results in a desired level of CAR, DE-CAR, and/or Side-CAR polypeptide expression in the eukaryotic cell. This desired level of CAR, DE-CAR, and/or Side-CAR polypeptide can produce eukaryotic cells with a desired level of anti-target cell activity, and/or a desired level of proliferative activity when placed in a subject.

The Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be used with a T-lymphocyte that has aggressive anti-tumor properties, such as those described in Pegram et al, CD28z CARs and armored CARs, 2014, Cancer J. 20(2):127-133, which is incorporated by reference in its entirety for all purposes. The RNA control device can be used with an armored CAR, DE-CAR, and/or Side-CAR polypeptide in a T-lymphocyte.

The above described Smart CAR, DE-CAR, RDE-CAR, Smart-DE-CAR, Smart-RDE-CAR, DE-RDE-CAR, Smart-DE-RDE-CAR, Side-CAR, and/or transgene-RDE embodiments can also include a DE-LEM, RDE-LEM, Smart LEM, Smart-DE-LEM, Smart-RDE-LEM, DE-RDE-LEM, and/or Smart-DE-RDE-LEM to provide controlled expression of LEM or DE-LEM. The amount of LEM or DE-LEM can be controlled so that its expansion signal is provided at a desired time. This control of the expansion signal is achieved by altering the amount of ligand (s) for the DE(s) and/or RNA control devices associated with the LEM or DE-LEM whereby the amount of LEM or DE-LEM is altered. The control of the LEM expansion signal can also be achieved by adding exogenous LEM to the eukaryotic cells at a desired time.

Pharmaceutical Compositions

Pharmaceutical compositions of the present invention may comprise a Smart CAR, DE-CAR, RDE-CAR, Smart-DE-CAR, Smart-RDE-CAR, DE-RDE-CAR, Smart-DE-RDE-CAR, Side-CAR, and/or transgene-RDE expressing cell, e.g., a plurality of Smart CAR, DE-CAR, RDE-CAR, Smart-DE-CAR, Smart-RDE-CAR, DE-RDE-CAR, Smart-DE-RDE-CAR, Side-CAR, and/or transgene-RDE expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. The pharmaceutically acceptable excipients described in Remington's Pharmaceutical Sciences (Mack Pub. Co., N.J. 1991) (which is incorporated herein by reference in its entirety for all purposes) can be appropriately used. The composition can be formulated into a known form suitable for parenteral administration, for example, injection or infusion. The composition may comprise formulation additives such as a suspending agent, a preservative, a stabilizer and/or a dispersant, and a preservation agent for extending a validity term during storage.

A composition comprising the eukaryotic cells described herein as an active ingredient can be administered for treatment of, for example, a cancer (blood cancer (leukemia), solid tumor (ovarian cancer) etc.), an inflammatory disease/autoimmune disease (pemphigus vulgaris, lupus erythematosus, rheumatoid arthritis, asthma, eczema), hepatitis, and an infectious disease the cause of which is a virus such as influenza and HIV, a bacterium, or a fungus, for example, a disease such as tuberculosis, MRSA, VRE, or deep mycosis, depending on an antigen to which a CAR, DE-CAR, and/or Side-CAR polypeptide binds.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, intranasally, intraarterially, intratumorally, into an afferent lymph vessel, by intravenous (i.v.) injection, or intraperitoneally. In one aspect, the T cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection. The administration can be done by adoptive transfer.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). A pharmaceutical composition comprising the eukaryotic cells described herein may be administered at a dosage of $10^4$ to $10^9$ cells/kg body weight, in some instances $10^5$ to $10^6$ cells/kg body weight, including all integer values within those ranges. A eukaryotic cell composition may also be administered multiple times at these dosages. Eukaryotic cells can also be administered by using infusion techniques that are commonly known in immunotherapy (see, e.g., Rosenberg et al., New Eng. J. of Med. 319:1676, 1988, which is incorporated by reference in its entirety for all purposes).

Uses of Eukaryotic Cells

Nucleic acids encoding Smart CAR(s), DE-CAR(s), RDE-CAR(s), Smart-RDE-CAR(s), DE-RDE-CAR(s), Smart-DE-CAR(s), Smart-DE-RDE-CAR(s), Side-CAR(s), and/or transgene-RDE(s) can be used to express CAR, DE-CAR, Side-CAR, and/or transgene polypeptides in eukaryotic cells. The eukaryotic cell can be a mammalian cell, including for example human cells or murine cells. The eukaryotic cells may also be, for example, hematopoietic cells including, e.g., T-cells, natural killer cells, B-cells, or macrophages.

The nucleic acids encoding the Smart CAR(s), DE-CAR(s), RDE-CAR(s), Smart-RDE-CAR(s), DE-RDE-CAR(s), Smart-DE-CAR(s), Smart-DE-RDE-CAR(s), Side-CAR(s), and/or transgene-RDE(s) can be used to express a desired level of CAR, DE-CAR, and/or Side-CAR polypeptide on the surface of the eukaryotic cell. In this aspect, the DE, RNA control device, RDE, and/or Side-CAR controls the level of CAR, DE-CAR, and/or Side-CAR polypeptide expression, at least in part, and by modulating the level of activity of the DE, RNA control device, RDE, and/or Side-CAR, a desired amount of CAR, DE-CAR, and/or Side-CAR polypeptide is expressed and displayed on the surface of the eukaryotic cell. The amount of CAR, DE-CAR, and/or Side-CAR polypeptide can be measured using antibodies specific for the CAR, DE-CAR, and/or Side-CAR polypeptide. The amount of CAR, DE-CAR, and/or Side-CAR polypeptide can be measured using the antigen recognized by the extracellular element. The amount of CAR, DE-CAR, and/or Side-CAR polypeptide can be measured in a functional assay of target cell killing. The amount of CAR, DE-CAR, and/or Side-CAR polypeptide can be measured in a functional assay for eukaryotic cell proliferation (induced by the CAR, DE-CAR, and/or Side-CAR polypeptide). The above eukaryotic cell can be a T-lymphocyte or a natural killer cell or a macrophage or other phagocytic cell type.

The ligand for the DE, the ligand for the RNA control device sensor, and/or the ligand for the Side-CAR can be added in increasing amounts until a desired level of eukaryotic cell activity is obtained. The desired eukaryotic cell activity can be killing of a target cell. Target cell killing can occur over a desired time period, e.g., the killing of a certain number of target cells in 12 hours, or 24 hours, or 36 hours, or two days, or 3, 4, 5, 6, 7, 8, 9, 10, 11, 12, 13, 14, 15, 16, 17, 18, 19, 20, 21, 22, 23, 24, 25, 26, 27, or 28 days, or two months, or 3, 4, 5, or 6 months. Target cell killing can be expressed as a half-life for a standardized number of target cells. The half-life of target cell killing can be 12 hours, 24 hours, 36 hours, or 2, 3, 4, 5, 6, 7, 8, 9, 10, 11, 12, 13, 14, 15, 16, 17, 18, 19, 20, 21, 22, 23, 24, 25, 26, 27, or 28 days, or two months, or 3, 4, 5, or 6 months. The desired eukaryotic cell activity can be proliferation. The cell proliferation can occur with a doubling time of 12 hours, 24 hours, 36 hours, two days, or 3, 4, 5, 6, or 7 days. The above eukaryotic cell can be a T-lymphocyte or a natural killer cell or a macrophage or other phagocytic cell type.

A regime of different amounts of ligand (for the sensor, DE, and/or Side-CAR) can be added over time so that different desired levels of CAR, DE-CAR, and/or Side-CAR polypeptide are present on the eukaryotic cell at different times. For example, in the treatment of cancer in patients with Smart CAR, DE-CAR, Smart-DE-CAR, and/or Side CAR T-cells or Smart CAR, DE-CAR, Smart-DE-CAR, and/or Side CAR natural killer cells, the amount of CAR, DE-CAR, and/or Side-CAR polypeptide expression may be reduced initially to reduce toxicity from tumor lysis, and as tumor mass is cleared, the amount of CAR, DE-CAR, and/or Side-CAR polypeptide expression can be increased to kill the remaining tumor cells as these become more rare within the body. The CAR, DE-CAR, and/or Side-CAR polypeptide expression may be increased initially, and as tumor mass is reduced the CAR, DE-CAR, and/or Side-CAR polypeptide expression level is reduced to reduce killing of healthy tissue that also may express target antigen. The reactivity towards tumor cells can be modulated so that the ratio of tumor cell killing to killing of normal tissue is maintained within a desired range. The amount of CAR, DE-CAR, and/or Side-CAR polypeptide expressed on the surface of the eukaryotic cell can be reduced by eukaryotic cell proliferation. As the eukaryotic cells proliferate, CAR, DE-CAR, and/or Side-CAR polypeptide will be diluted if the expression level from the Smart CAR, DE-CAR, Smart-DE-CAR, and/or Side CAR nucleic acid is insufficient to keep the CAR, DE-CAR, and/or Side-CAR polypeptide copy number at the level found in the parent eukaryotic cell (i.e., if the parent cell does not double its amount of CAR, DE-CAR, and/or Side-CAR polypeptide then each daughter cell will have a decreased amount CAR, DE-CAR, and/or Side-CAR polypeptide compared to the parent cell). The CAR, DE-CAR, and/or Side-CAR polypeptide can be designed to have a short half-life, in comparison to the doubling time for the eukaryotic cell in the subject. The ligand(s) can have a short half-life in the subject when compared to the doubling time of the eukaryotic cell in the subject. An anti-ligand antibody or a different ligand binding molecule can be administered to the subject or given to the eukaryotic cells (in vitro) so that the ligand binds to the antibody or ligand binding molecule and cannot react with the DE, RNA control device sensor, and/or Side-CAR. The above eukaryotic cell can be a T-lymphocyte or a natural killer cell or a macrophage or other phagocytic cell type.

Eukaryotic cells with Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) can express a desired amount of CAR, DE-CAR, and/or Side-CAR polypeptide so that a subject containing the eukaryotic cells with the CAR, DE-CAR, and/or Side-CAR polypeptide can produce a therapeutic level of target cell killing while keeping toxicity and adverse events at acceptable levels. The above eukaryotic cell can be a T-lymphocyte or a natural killer cell or a macrophage or other immune cell type. For example, Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) of the invention can be used to reduce tumor lysis syndrome, cytokine storms, or healthy tissue killing by T-lymphocytes with Smart CAR, DE-CAR, Smart-DE-CAR, and/or Side CAR.

The Smart CAR, Smart-DE-CAR, Smart-RDE-CAR, Smart-DE-RDE-CAR, and/or Side-CAR can be associated with two or more RNA control devices. Different amounts of the two or more ligands for the DE, Side-CAR, and/or two or more RNA control devices can be added to the eukaryotic cells to produce a desired amount of CAR, DE-CAR, and/or Side-CAR polypeptide in the eukaryotic cell. Different regimes of combinations of the ligands can be applied to the eukaryotic cells to produce a desired profile over time of the amount of CAR, DE-CAR, and/or Side-CAR polypeptide on the surface of the eukaryotic cell.

The desired amount of CAR expression can activate effector function in a T lymphocyte or natural killer cell with a minimal amount of T lymphocyte exhaustion, dysfunction, and/or other dysregulatory process (such as change of cell fate, or change in metabolism effecting for example glycolysis). The desired amount of CAR expression can activate effector function in a T lymphocyte or natural killer cell with a minimal amount of inhibition, exhaustion, and/or dysfunction of the cell which causes the T lymphocyte or natural killer cell to become exhausted or dysfunctional. The desired amount of CAR expression can provide a desired dynamic range of effector function in response to target antigen present at a target cell. The desired amount of CAR expression can provide a desired range of effector function. The desired amount of CAR expression can provide a small dynamic range of effector function (acts like an on-off switch), for example, when target cells have a high density of target antigen and healthy, nontarget cells have a low density of target antigen. The desired amount of CAR expression can allow the eukaryotic cell to distinguish between target cells (on—CARs activate effector function) versus healthy, normal cells (off—CAR activates little or no effector function). The desired amount of CAR expression can increase the avidity of the engineered eukaryotic cell (e.g., T lymphocytes or natural killer cells) for target cells whereby effect on target cells is increased. The desired amount of CAR expression can increase the avidity of the engineered eukaryotic cell (e.g., T lymphocytes or natural killer cells) for target cells whereby target cell killing is enhanced. The desired amount of CAR expression can increase the avidity of the engineered hematopoietic cell (e.g., T lymphocytes or natural killer cells) for target cells whereby cytokine secretion is enhanced.

T-cells (e.g., CD4+ or CD8+) or natural killer cells can be engineered with a polynucleotide encoding a Smart CAR, DE-CAR, RDE-CAR, Smart-DE-CAR, Smart-RDE-CAR, DE-RDE-CAR, Smart-DE-RDE-CAR, and/or Side-CAR. Ligand for the RNA control device, DE, or Side CAR is added to the T-cells (e.g., CD4+ or CD8+) or natural killer cells can be added in increasing amounts to obtain a desired amount of effector function. The desired amount of effector function can be an optimized amount of effector function with a known amount (and/or density) of target antigen on target cells. Effector function can be target cell killing, activation of host immune cells, cytokine secretion, production of granzymes, production of apoptosis inducing ligands, production of other ligands that modulate the immune system, etc. The effector function can be secretion of cytokines such as, for example, IL-2, IFN-γ, TNF-α, TGF-β, and/or IL-10. Effector function can be the killing of target cells. Target cells can be killed with granzymes. Target cells can be induced to undergo apoptosis. Eukaryotic cells with CARs can kill target cells through apoptosis and granzymes. The optimal concentration for ligand may increase effector function. The optimal concentration of ligand can increase the dynamic range of effector function (effector activity in response to target antigen). The optimal concentration for ligand may provide a desired amount of effector function and a desired (or tolerable) amount of exhaustion, dysfunction, and/or inhibition of the eukaryotic cell (e.g., T-lymphocyte or natural killer cell). The optimal amount of activity can yield a desired proliferative activity. The optimal amount of activity can be an amount of target binding or an amount of an effector activity (e.g., target cell killing). The optimal CAR, DE-CAR and/or Side-CAR expression can provide a desired rate of memory cell formation when the eukaryotic cell is an appropriate immune cell. Other eukaryotic cell activities that may be optimized include any activities useful in the treatment of disease, including, for example, rate of memory cell formation, release rate of cytokines, phagocytosis, binding of target, recruitment of innate myeloid or lymphoid cells, epitope spreading, development of exhaustion, development of cell dysfunction, and/or inhibition of eukaryotic cell function.

The RDE, DE, RNA control device, or Side CAR regulatory element can be used to control expression of a transgene. This transgene expression can deliver a payload at a target site. Expression of the transgene can cause a desired change in the eukaryotic cell. An RDE regulated by GAPDH can be used for payload delivery, and the eukaryotic cell (e.g., T-cell, natural killer cell, B-cell, macrophage, dendritic cell, or other antigen presenting cell) can be activated (e.g., by a CAR) when it reaches the target site. Upon activation of the eukaryotic cell at the target site through the CAR, the cell induces glycolysis and the GAPDH releases from the RDE allowed payload expression and delivery. The target site can be a tumor or infection and the transgene could encode a cytokine, a chemokine, an antibody, a checkpoint inhibitor, a granzyme, an apoptosis inducer, complement, an enzyme for making a cytotoxic small molecule, an enzyme that cleaves peptides or saccharides (e.g., for digesting a biofilm), other cytotoxic compounds, or other polypeptides that can have a desired effect at the target site. Checkpoint inhibitors include agents that act at immune checkpoints including, for example, cytotoxic T-lymphocyte-associated antigen 4 (CTLA4), programmed cell death protein (PD-1), Killer-cell Immunoglobulin-like Receptors (KIR), and Lymphocyte Activation Gene-3 (LAG3). Examples of checkpoint inhibitors that may be used as payloads include, for example, Nivolumab (Opdivo), Pembrolizumab (Keytruda), Atezolizumab (Tecentriq), Ipilimumab (Yervoy), Lirilumab, and BMS-986016. Nivolumab, Atezolizumab and Pembrolizumab act at the checkpoint protein PD-1 and inhibit apoptosis of anti-tumor immune cells. Some checkpoint inhibitors prevent the interaction between PD-1 and its ligand PD-L1. Ipilimumab acts at CTLA4 and prevents CTLA4 from downregulating activated T-cells in the tumor. Lirilumab acts at KIR and facilitates activation of Natural Killer cells. BMS-986016 acts at LAG3 and activates antigen-specific T-lymphocytes and enhances cytotoxic T cell-mediated lysis of tumor cells. Cytokines can include, for example, IL-2, IL-12, IL-15, IL-18, IFN-γ, TNF-α, TGF-β, and/or IL-10. Cytotoxic agents can include, for example, granzymes, apoptosis inducers, complement, or a cytotoxic small molecule. The payload delivered at a target site (e.g., non-tumor target site) can be a factor that protects the target site such as, for example, an anti-inflammatory, a factor that attracts T-regulatory cells to the site, or cytokines or other factors that cause suppression and reduction in immune activity. The payload can be an enzyme that cleaves peptides or saccharides, for example hyaluronidase, heparanase, metalloproteinases and other proteinases which can be used, for example, to digest an undesired biofilm. The payload can be an imaging agent that allows the target site to be imaged. The payload may be a polypeptide that can be imaged directly, or it can be a polypeptide that interacts with a substrate to make a product that can be imaged, imaging polypeptides include, for example, thymidine kinase (PET), dopamine D2 (D2R) receptor, sodium iodide transporter (NIS), dexoycytidine kinase, somatostatin receptor subtype 2, norepinephrine transporter (NET), cannabinoid receptor, glucose transporter (Glut1), tyrosinase, sodium iodide transporter, dopamine D2 (D2R) receptor, modified haloalkane dehalogenase, tyrosinase, β-galactosidase, and somatostatin receptor 2. These reporter payloads can be imaged using, for example, optical imaging, ultrasound imaging, computed tomography imaging, optical coherence tomography imaging, radiography imaging, nuclear medical imaging, positron emission tomography imaging, tomography imaging, photo acoustic tomography imaging, x-ray imaging, thermal imaging, fluoroscopy imaging, bioluminescent imaging, and fluorescent imaging. These imaging methods include Positron Emission Tomography (PET) or Single Photon Emission Computed Tomography (SPECT).

Thymidine kinase can be used with PET reporter probes such as, for example, [$^{18}$F]9-(4-[$^{18}$F]-fluoro-3-hydroxymethylbutyl)-guanine, a fluorine-18-labelled penciclovir analogue, which when phosphorylated by thymidine kinase (TK) becomes retained intracellularly, or is 5-(76) Br-bromo-2'-fluoro-2'-deoxyuridine. The relevant reporter probes for each of the PET reporters are well known to the skilled artisan. An exemplary reporter probe for dopamine D2 (D2R) receptor is 3-(2'-[$^{18}$F]fluoroethyl)spiperone (FESP) (MacLaren et al., Gene Ther. 6(5):785-91 (1999)). An exemplary reporter probe for the sodium iodide transporter is $^{124}$I, which is retained in cells following transport by the transporter. An exemplary reporter probe for deoxycytidine kinase is 2'-deoxy-2'-$^{18}$F-5-ethyl-1-β-d-arabinofuranosyluracil ($^{18}$F-FEAU). An exemplary reporter probe for somatostatin receptor subtype 2 is $^{111}$In-, $^{99m/94m}$Tc-, $^{90}$Y-, or $^{177}$Lu-labeled octreotide analogues, for example $^{90}$Y-, or $^{177}$Lu-labeled DOTATOC (Zhang et al., J Nucl Med. 50(suppl 2):323 (2009)); $^{68}$Ga-DOTATATE; and $^{111}$In-DOTABASS (see. e.g., Brader et al., J Nucl Med. 54(2):167-172 (2013), incorporated herein by reference). An exemplary reporter probe for norepinephrine transporter is $^{11}$C-m-hydroxyephedrine (Buursma et al., J Nucl Med. 46:2068-2075 (2005)). An exemplary reporter probe for the cannabinoid receptor is $^{11}$C-labeled CB2 ligand, $^{11}$C-GW405833 (Vandeputte et al., J Nucl Med. 52(7):1102-1109 (2011)). An exemplary reporter probe for the glucose transporter is [$^{18}$F]fluoro-2-deoxy-d-glucose (Herschman, H. R., Crit Rev Oncology/Hematology 51:191-204 (2004)). An exemplary reporter probe for tyrosinase is N-(2-(diethylamino)ethyl)-$^{18}$F-5-fluoropicolinamide (Qin et al., Sci Rep. 3:1490 (2013)). Other reporter probes are described in the art, for example, in Yaghoubi et al., Theranostics 2(4):374-391 (2012), incorporated herein by reference.

An exemplary photoacoustic reporter probe for β-galactosidase is 5-bromo-4-chloro-3-indolyl-β-D-galactoside (X-gal) (Li et al., J Biomed Opt. 12(2):020504 (2007)). Exemplary X-ray reporter includes, among others, somatostatin receptor 2, or other types of receptor based binding agents. The reporter probe can have a radiopaque label moiety that is bound to the reporter probe and imaged, for example, by X-ray or computer tomography. Exemplary radiopaque label is iodine, particularly a polyiodinated chemical group (see, e.g., U.S. Pat. No. 5,141,739), and paramagnetic labels (e.g., gadolinium), which can be attached to the reporter probe by conventional means. Optical imaging agents include, for example, a fluorescent polypeptide. Fluorescent polypeptides include, for example, green fluorescent protein from Aequorea victoria or Renilla reniformis, and active variants thereof (e.g., blue fluorescent protein, yellow fluorescent protein, cyan fluorescent protein, etc.); fluorescent proteins from Hydroid jellyfishes, Copepod, Ctenophora, Anthrozoas, and Entacmaea quadricolor, and active variants thereof; and phycobiliproteins and active variants thereof. The optical imaging agent can also be a bioluminescent polypeptide. These include, for example, aequorin (and other $Ca^{+2}$ regulated photoproteins), luciferase based on luciferin substrate, luciferase based on Coelenterazine substrate (e.g., Renilla, Gaussia, and Metridina), and luciferase from Cypridina, and active variants thereof.

The desired amount of CAR expression may consider the target cell concentration, density of target antigen, whether target cells are associated with other target cells (e.g., in a tumor or a biofilm), the binding affinity ($K_d$) of the extracellular element (antigen binding element) for the target antigen, and the concentration of eukaryotic cells with CARs. These parameters can be used to arrive at a desired density of CARs on the eukaryotic cell which will define the desired level of CAR expression. The desired amount of CAR expression may also consider the amount of inhibitory receptors (IR) expressed on the eukaryotic cell, and the amount of inhibitory receptor ligand (IRL) expressed on target (and other) cells. The following equations can be used, at least in part, to arrive at the desired amount of CAR expression:

$$\text{CAR Expression} = [\text{target cell}][\text{target antigen density}][K_d][\text{host cells}] \quad \text{I}$$

$$\text{CAR Expression} = \frac{[\text{target cell}][\text{target antigen density}][K_d][\text{host cells}]}{[IR][IRL]} \quad \text{II}$$

Equation II can optionally include [target antigen density on healthy cells] in the denominator.

The desired amount of CAR expression can produce a desired number of CARs on the surface of the eukaryotic cell. The desired amount of CAR expression can produce 2-100,000 CARs (or DE-CARs or Side-CARs) on the surface of the eukaryotic cell. The eukaryotic cell can be a T-lymphocyte and the number of CARs (or DE-CARs or Side-CARs) on the surface of the T-lymphocyte can be 2-100,000. The CAR, DE-CAR, and/or Side-CAR can bind to target ligand with an affinity in the micromolar (µM) range and the desired number of CARs, DE-CARs, and/or Side-CARs on the surface of the T-lymphocyte or natural killer cell can be 100-500,000. The CAR, DE-CAR, and/or Side-CAR can bind to target ligand with an affinity in the nanomolar (nM) range and the desired number of CARs, DE-CARs, and/or Side-CARs on the surface of the T-lymphocyte or natural killer cell can be 2-100,000.

The desired amount of CAR expression can produce 2-1,000, 10-1,000, 10-5,000, 10-10,000, 10-50,000, 10-100,000, 10-500,000, or 10-1,000,000 CARs (or DE-CARs or Side-CARs) on the surface of the eukaryotic cell. The desired amount of CAR expression can produce 100-1,000, 100-5,000, 100-10,000, 100-50,000, 100-100,000, 100-500,000, 100-1,000,000, 1,000-5,000, 1,000-10,000, 1,000-50,000, 1,000-100,000, 1,000-500,000, 1,000-1,000,000, 10,000-50,000, 10,000-100,000, 10,000-500,000, or 10,000-1,000,000 CARs (or DE-CARs or Side-CARs) on the surface of the eukaryotic cell. The desired amount of CAR expression can produce at least 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 350, 400, 450, 500, 550, 600, 650, 700, 750, 800, 850, 900, 950, 1000, 2000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 60,000, 65,000, 70,000, 75,000, 80,000, 85,000, 90,000, 95,000 or 100,000 CARs (or DE-CARs or Side-CARs) on the surface of the eukaryotic cell. The desired amount of CAR expression can produce fewer than 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 350, 400, 450, 500, 550, 600, 650, 700, 750, 800, 850, 900, 950, 1000, 2000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 60,000, 65,000, 70,000, 75,000, 80,000, 85,000, 90,000, 95,000 or 100,000 CARs (or DE-CARs or Side-CARs) on the surface of the eukaryotic cell. The desired amount of CAR expression can produce 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 350, 400, 450, 500, 550, 600, 650, 700, 750, 800, 850, 900, 950, 1000, 2000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 60,000, 65,000, 70,000, 75,000, 80,000, 85,000, 90,000, 95,000 or 100,000 CARs (or DE-CARs or Side-CARs) on the surface of the eukaryotic cell. The eukaryotic cell can be a T-lymphocyte and the number of CARs (or DE-CARs or Side-CARs) on the surface of the T-lymphocyte can be 100-100,000. The CAR, DE-CAR, and/or Side-CAR can bind to target ligand with an affinity in the micromolar (µM) range (e.g., 1-500 µM) and the desired number of CARs, DE-CARs, and/or Side-CARs on the surface of the T-lymphocyte or natural killer cell can be 100-100,000. The CAR, DE-CAR, and/or Side-CAR can bind to target ligand with an affinity in the micromolar (µM) range and the desired number of CARs, DE-CARs, and/or Side-CARs on the surface of the T-lymphocyte or natural killer cell can be 100-1,000, 100-5,000, 100-10,000, 100-50,000, 100-100,000, 100-500,000, 100-1,000,000, 1,000-5,000, 1,000-10,000, 1,000-50,000, 1,000-100,000, 1,000-500,000, 1,000-1,000,000, 10,000-50,000, 10,000-100,000, 10,000-500,000, or 10,000-1,000,000. The CAR, DE-CAR, and/or Side-CAR can bind to target ligand with an affinity in the nanomolar (nM) range and the desired number of CARs, DE-CARs, and/or Side-CARs on the surface of the T-lymphocyte or natural killer cell can be 10-100,000. The CAR, DE-CAR, and/or Side-CAR can bind to target ligand with an affinity in the nanomolar (nM) range (e.g., 1-500 nM) and the desired number of CARs, DE-CARs, and/or Side-CARs on the surface of the T-lymphocyte or natural killer cell can be 100-1,000, 100-5,000, 100-10,000, 100-50,000, 100-100,000, 100-500,000, 100-1,000,000, 1,000-5,000, 1,000-10,000, 1,000-50,000, 1,000-100,000, 1,000-500,000, 1,000-1,000,000, 10,000-50,000, 10,000-100,000, 10,000-500,000, or 10,000-1,000,000.

The desired amount of CAR expression can be an amount which gives a desired amount of area under the curve for a desired activity (e.g., target cell killing and/or cytokine release as a function of time). The desired amount of CAR expression can be the amount which gives the maximal amount of area under the curve for a desired activity (e.g., target cell killing and/or cytokine release). The desired amount of CAR expression can be the amount which gives the optimal amount of area under the curve for a desired activity (e.g., target cell killing and/or cytokine release). The desired amount of CAR expression can be the amount which gives the desired activity rate maximum (analogous to $C_{max}$) for a desired activity (e.g., target cell killing and/or cytokine release). The desired amount of CAR expression can be the amount which gives the maximal activity rate for a desired activity (e.g., target cell killing and/or cytokine release). The desired amount of CAR expression can be the amount which gives the optimal activity rate for a desired activity (e.g., target cell killing and/or cytokine release). Eukaryotic cell activities that may be customized include, for example, any activities useful in the treatment of disease, including, for example, proliferation rate, rate of memory cell formation, release rate of cytokines, phagocytosis, binding of target, recruitment of innate myeloid or lymphoid cells, epitope spreading, development of exhaustion, development of cell dysfunction, and/or inhibition of eukaryotic cell function. In an aspect, the desired amount of CAR, DE-CAR, and/or Side-CAR polypeptide(s) can be such so that exhaustion, dysfunction and/or inhibitory signals for the eukaryotic cell can be minimized.

The desired amount of CAR expression can be the amount which gives the desired amount of area under the curve for a desired activity (e.g., target cell killing and/or cytokine release) with a desired amount of exhaustion, dysfunction, and/or inhibitory receptor activity and/or expression. The desired amount of CAR expression can be the amount which gives the desired amount of area under the curve for a desired activity (e.g., target cell killing and/or cytokine release) with a tolerable amount of inhibitory activity, T-lymphocyte dysfunctional activity, and/or exhaustion. The desired amount of CAR expression can be the amount which gives the maximal amount of area under the curve for a desired activity (e.g., target cell killing and/or cytokine release) with a minimal amount of host cell dysfunction, exhaustion, and/or inhibitory receptor expression. The desired amount of CAR expression can be the amount which gives the maximal amount of area under the curve for a desired activity (e.g., target cell killing and/or cytokine release) with a minimal amount of host cell dysfunction. The desired amount of CAR expression can be the amount which gives the maximal amount of area under the curve for a desired activity (e.g., target cell killing and/or cytokine release) with a desired ratio of area under the curve for the desired activity versus area under the curve for an inhibitory activity. The desired amount of CAR expression can be the amount which gives the maximal amount of area under the curve for a desired activity (e.g., target cell killing and/or cytokine release) with a desired ratio of area under the curve for the desired activity versus area under the curve for host cell dysfunction. The desired amount of CAR expression can be the amount which gives a maximal ratio of area under the curve for effector function versus area under the curve for inhibitory receptor activity. The desired amount of CAR expression can be the amount which gives a maximal ratio of area under the curve for effector function versus area under the curve for host cell dysfunction activity. The desired amount of CAR expression can be the amount which gives a maximal ratio of area under the curve for effector function versus area under the curve for inhibitory or dysfunction activity, and/or exhaustion.

The desired amount of CAR expression can be the amount that gives a desired area under the curve for a desired activity over a period of time, and a desired length of time for the CAR cells to recover (or maintain) the desired activity (during an off period) for the next on cycle (cycle for effector function). The desired amount of CAR expression can be the amount that gives a desired area under the curve for a desired activity, and a desired length of time for the CAR cells to regain the desired effector function (during an off period). The desired amount of CAR expression can be correlated with the rate at which effector function is induced, the rate at which inhibitory function, exhaustion, and/or dysfunction of the T-lymphocyte (or natural killer cell) is induced, and the rate at which inhibitory receptors are lost and/or inhibitory activity is lost from the T-lymphocyte or natural killer cell when CAR expression is turned off.

The desired amount of CAR expression can be cycled so the eukaryotic cell goes through periods of on (activation of eukaryotic cell and effector function) and off (no activation—down regulation of inhibitor receptors). The desired amount of CAR expression can be cycled so that cells activated by the CAR eukaryotic cell are cycled, e.g., cells activated by cytokines expressed by the eukaryotic cell with the CAR (and other immune cells that are activated by the eukaryotic cell). The T lymphocytes and/or natural killer cells can be engineered to knock out inhibitory receptor expression, including for example, PD-1 and CTLA-4. Cycling of CAR expression along with activated and deactivated states can be done on a population basis. Cycling of CAR expression along with activated and deactivated states can be done for individual eukaryotic cells.

Optimal expression of a CAR, DE-CAR, or Side-CAR can be determined by taking the first derivative (to find the maximum) of a desired effector activity as a function of time. The following equations can be used to describe the effector activity, which can be dependent on the rate of generation of activation related signaling molecules ($F_A$), subtracted by the rate of generation of inhibition related signaling molecules ($F_I$), and optionally subtracted by some loss of effector function parameter $Q_m$ that is dependent on alterations in metabolic state.

$$\frac{dE}{dt} = F_A - F_I - Q_m$$

$F_A$ is the rate of generation of activation molecules which can also be expressed as $dN_A/dt$. $F_A$ can be linearly dependent on $N_{RT}$ (the instantaneous number of receptors bound to targets), as well as a constant, $c_{activation}$.

$$F_A = \frac{dN_A}{dt} = N_{RT} \cdot c_{activation}$$

$N_{RT}$ can be found through the reaction equation and the corresponding rates of association and dissociation.

$$[R][T] \overset{k1}{\to} [RT]$$
$$[RT] \overset{k\_1}{\to} [R][T]$$
$$\frac{dN_{RT}}{dt} = k1 N_R N_T - k\_1 N_{RT}$$

Solving this first order ODE for $dN_{RT}$

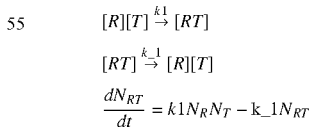

At equilibrium conditions $dN_{RT}/dt$ can be set to 0, leaving $N_{RT}$ which can be substituted into the equation for $F_A$, purely dependent on NR (the number of receptors), NT (number of targets), k1 and k_1 which are the rate constants of association and dissociation of the receptor target complex, which is defined by antibody affinity for its target.

$$N_{RT} = \frac{k1 N_R N_T}{k\_1}$$

For $F_I$, we seek to provide a negative feedback for activation, which is consistent with observed biological function. Here we express it as an exponential function of $N_A$ and a constant $c_2$ and $c_{inhibition}$.

$$F_I = \frac{dN_I}{dt} = e^{C_2 N_A} \cdot c_{inhibition}$$

The optional form of Q can be an arbitrary function of $N_A$ which is often dependent on the activation state as well.

$$Q = f(N_A) \cdot c_{metabolism}$$

Figure 4:
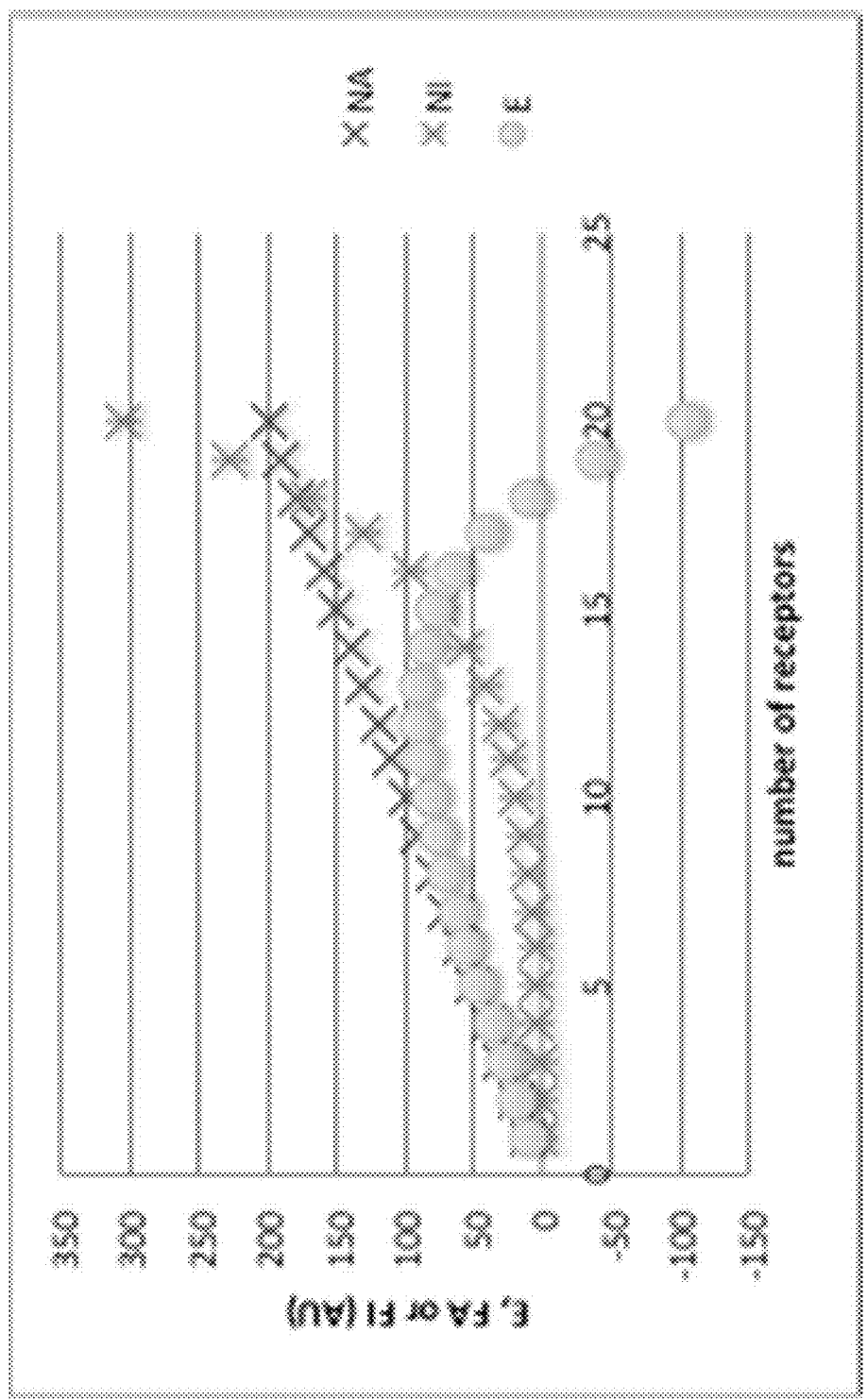
FIG. 4 provides a graph showing effector function (E), activation signaling ($N_A$) and inhibitory signaling ($N_I$) over time for a number of CAR receptors.

These equations can be used to plot for E, and for a given nT, k1, k_1 and varying $N_R$, the maximum E can be identified as depicted in FIG. 4. FIG. 4 shows graphs of effector function (E), activation (of effector function) signal or molecules (NA), and inhibition (of effector function) signal or molecules (NI) as a function of the number of CAR receptors on the cell. The graphs in FIG. 4 have a set target concentration and the graphs show that maximal (and in some case optimal) effector function occurs at CAR receptor number less than the maximal number of CAR receptors that can be expressed on the eukaryotic cell surface.

Figure 5:
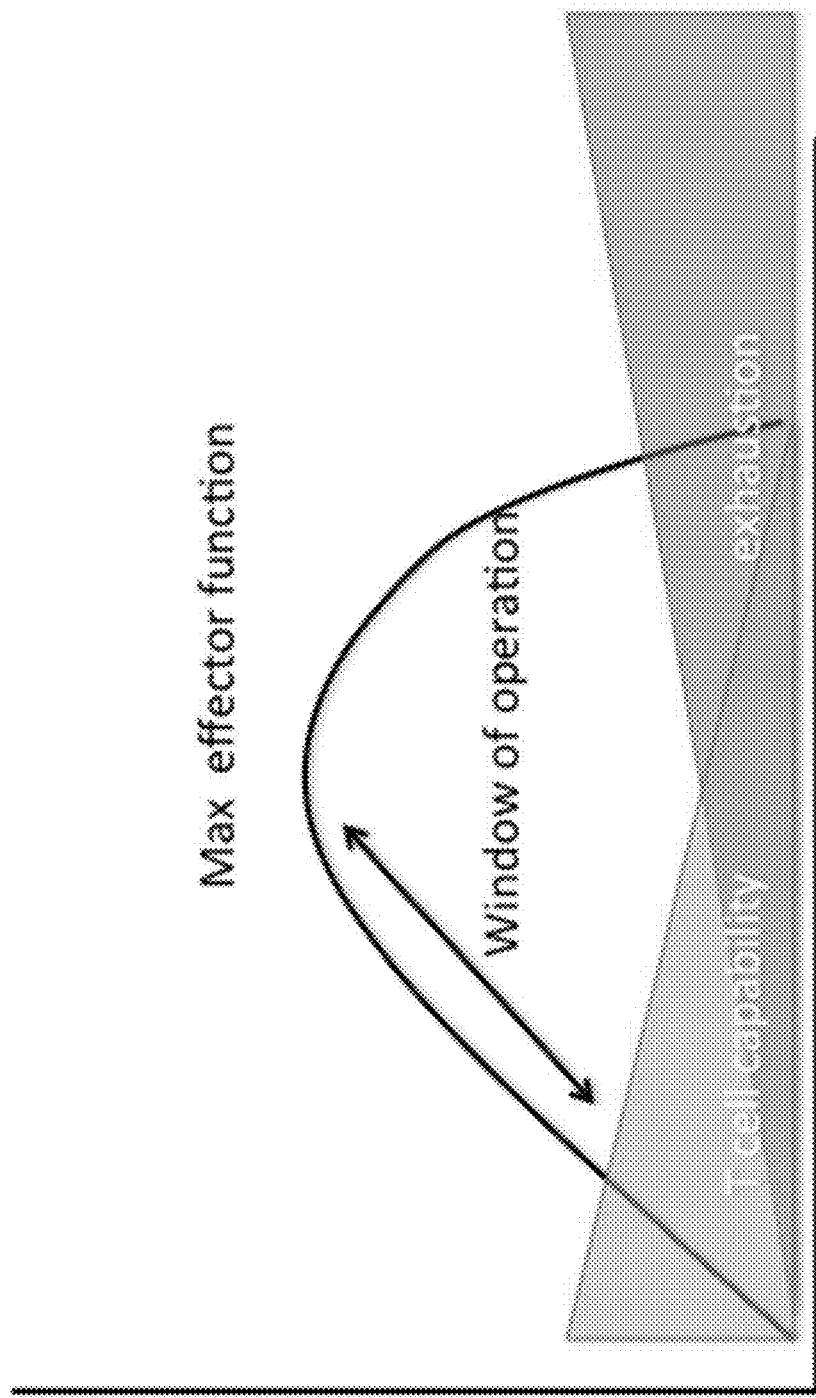
FIG. 5 provides a diagram showing effector function, T-cell capability and T-cell exhaustion (or dysfunction) for CD8+ T-cells receiving continuous antigen stimulation over time.

The desired amount of CAR expression can consider the competing processes of eukaryotic host cell activation (as correlated with CAR expression) and inhibition of the effector function of the host cell (deactivation, dysfunction, and/or exhaustion). The desired amount of CAR expression can consider the competing processes of T-lymphocyte or natural killer cell activation (as correlated with CAR expression) and inhibition of effector function (deactivation, dysfunction and/or exhaustion). FIG. 5 shows that T-lymphocyte activation (effector function of the host cell) decreases as the inhibition (exhaustion, dysfunction and/or deactivation) rises. The operable window for the Smart-CAR host cell can be defined by these two processes as shown in FIG. 5. The Smart-CAR host cells can be exposed to cycles of ligand that keep the effector function in the window of operation (by turning off CAR expression the host cells should reduce activation which in turn will reduce expression of inhibitory process, e.g., inhibitory receptors, in the host cell).

Figure 7:
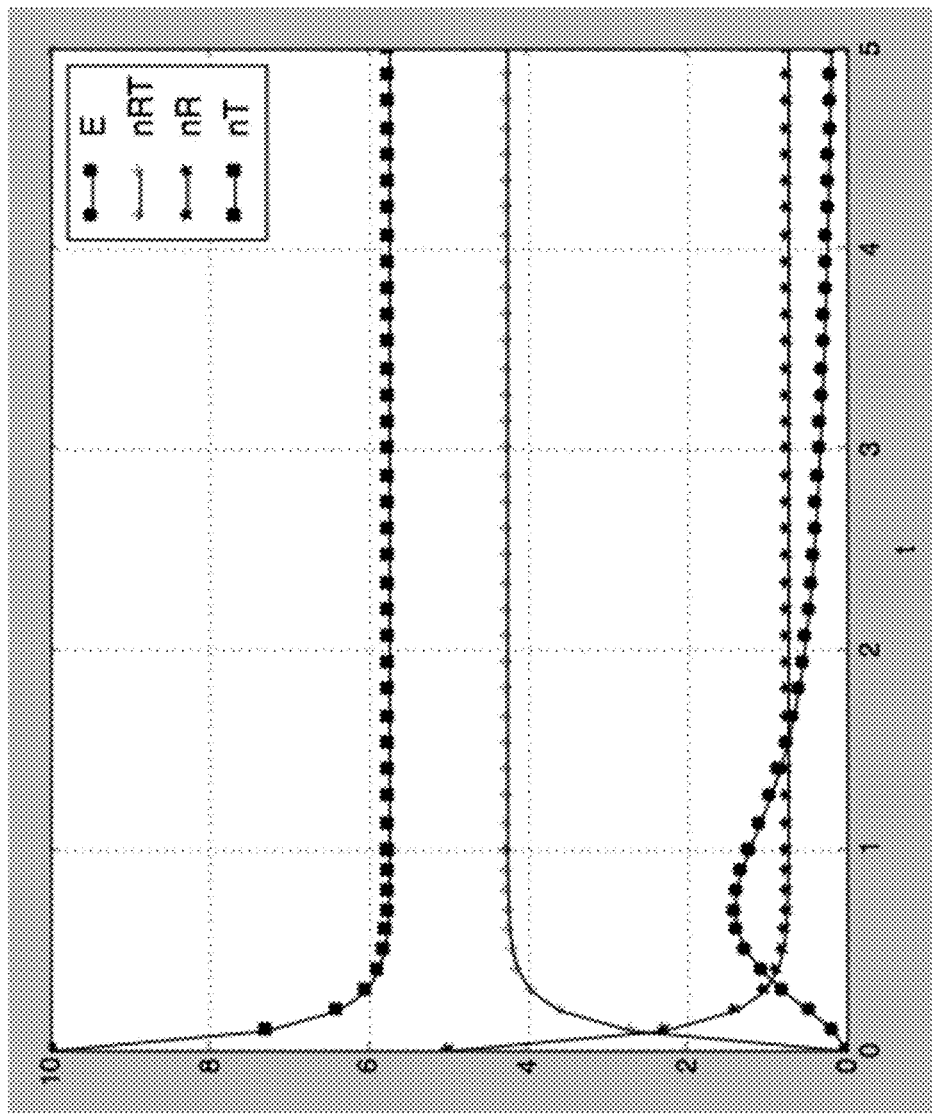
FIG. 7 provides a graph for a CAR T-lymphocyte showing time versus effector function (E), number of target cells (nT), number of CAR receptors (nR), and number of CAR receptor-target cell interactions (nRT).
Figure 8:
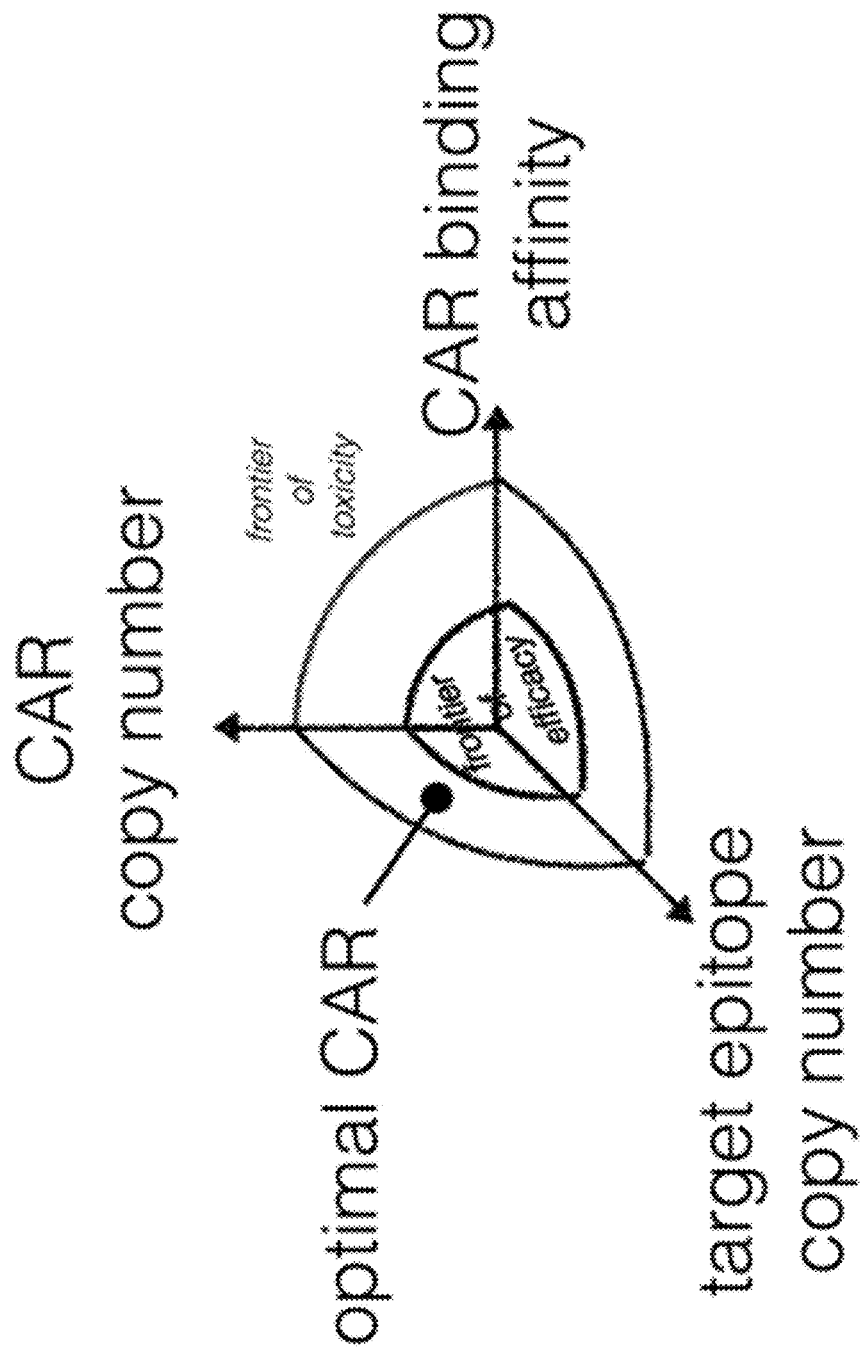
FIG. 8 shows a diagram for optimal CAR activity where the three variables are CAR copy number, target epitope copy number and CAR binding affinity.
Figure 9:
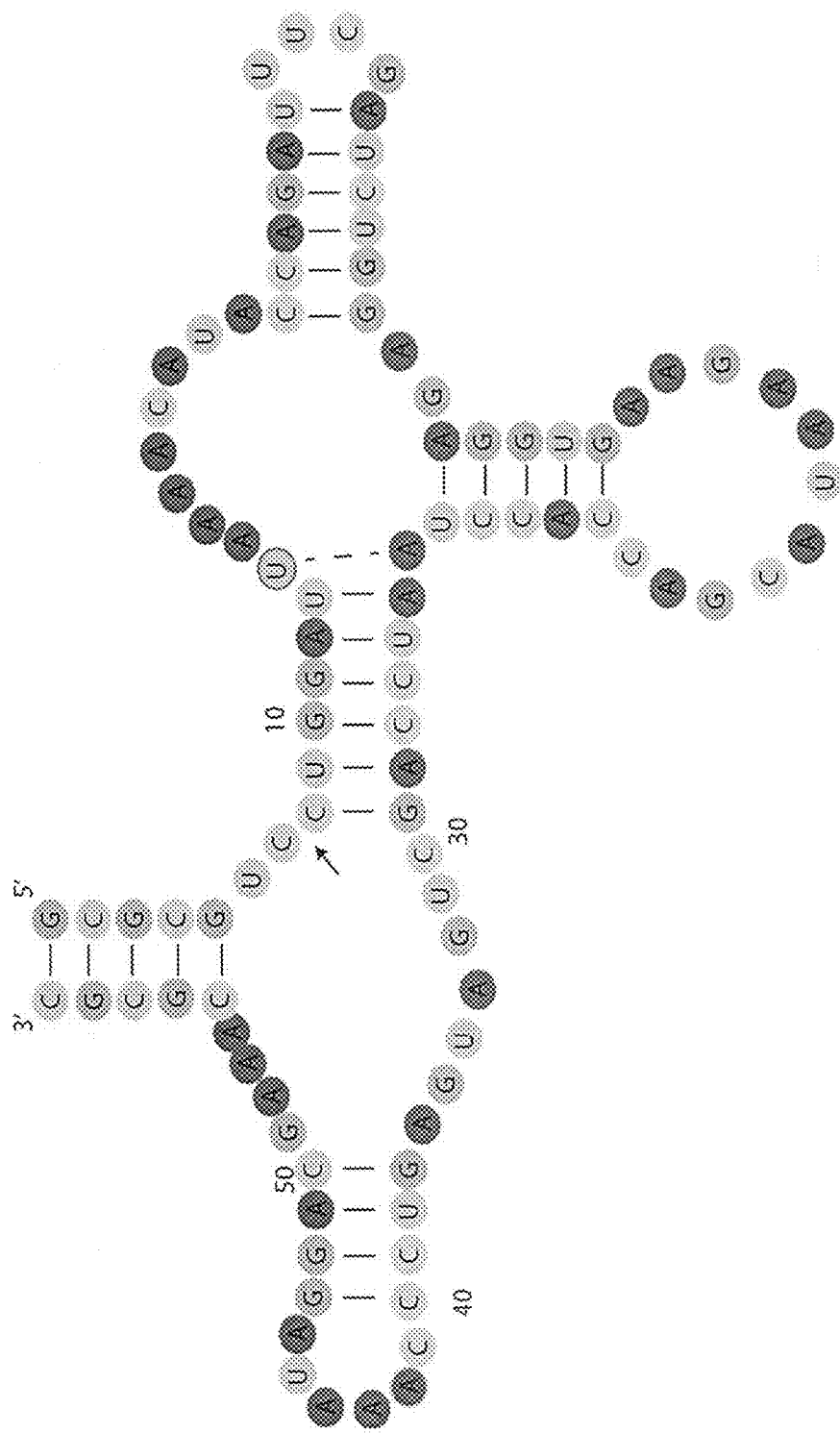
FIG. 9 depicts a new tetracycline RNA control device (SEQ ID NO: 1).
Figure 10:
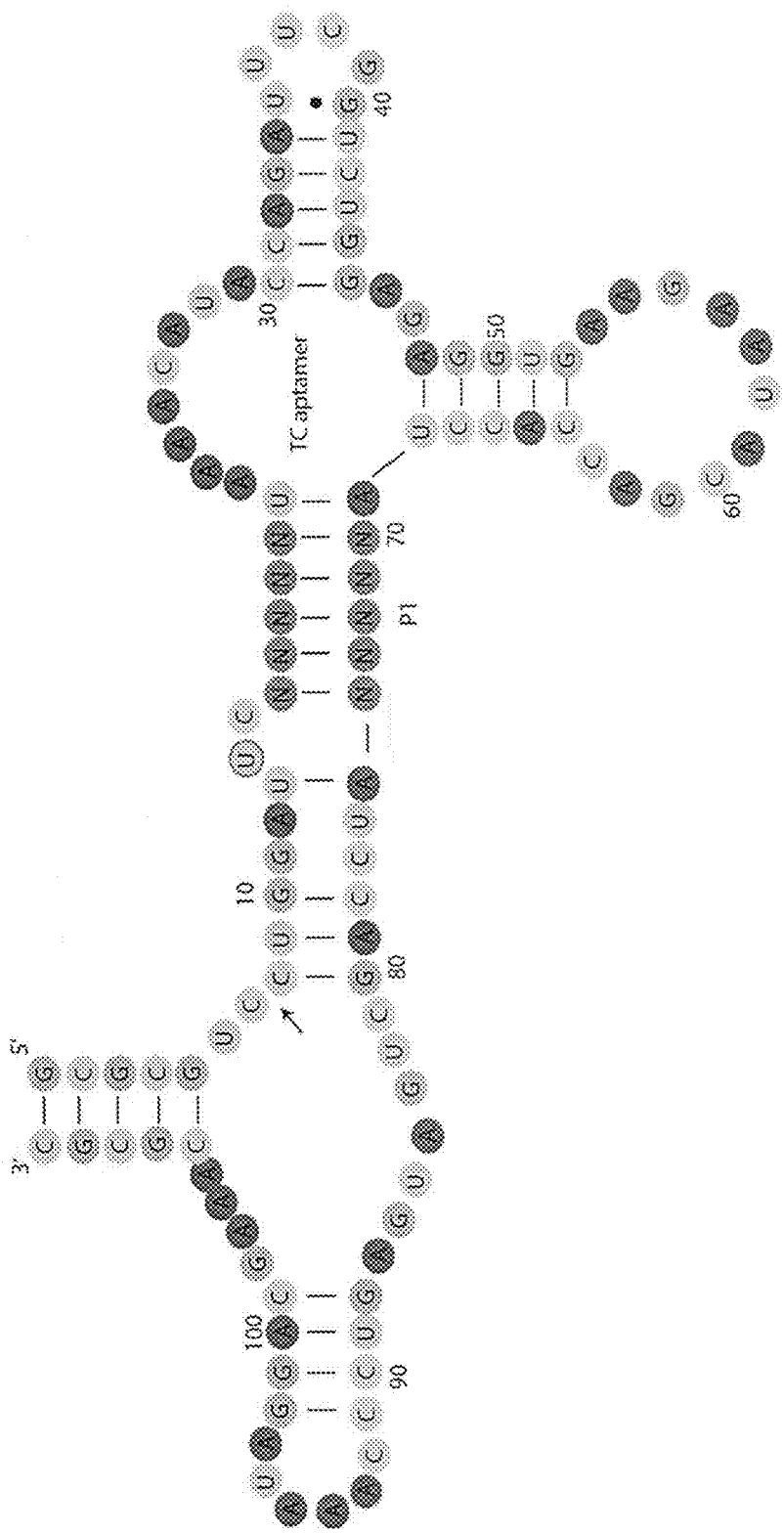
FIG. 10 depicts an alternative new tetracycline RNA control device (SEQ ID NO: 2).
Figure 11:
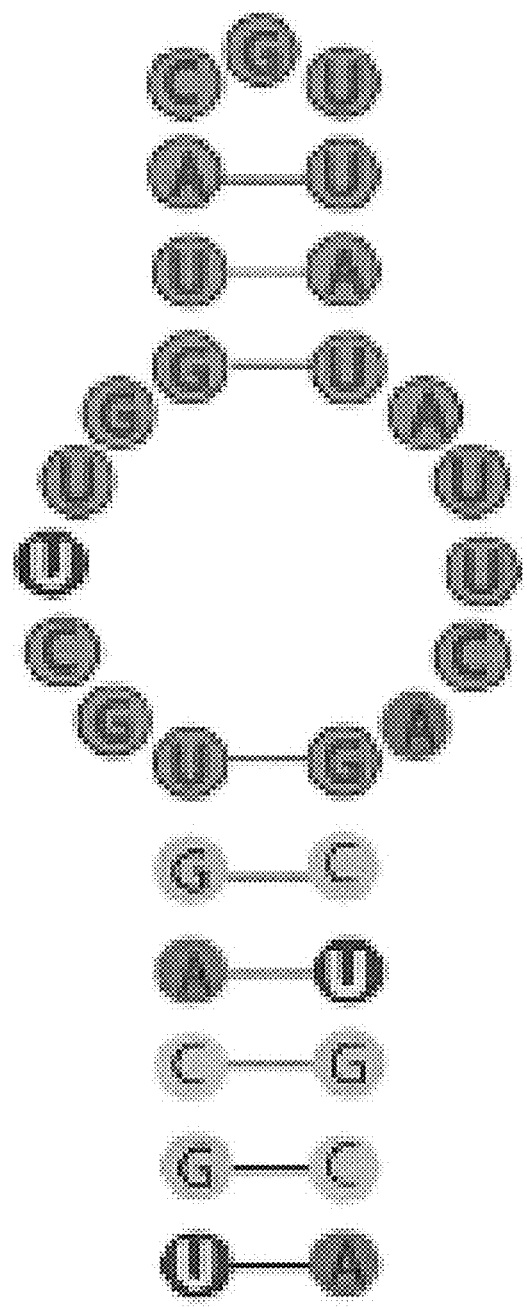
FIG. 11 depicts an aptamer that binds 6R-folinic acid (SEQ ID NO: 3).
Figure 12:
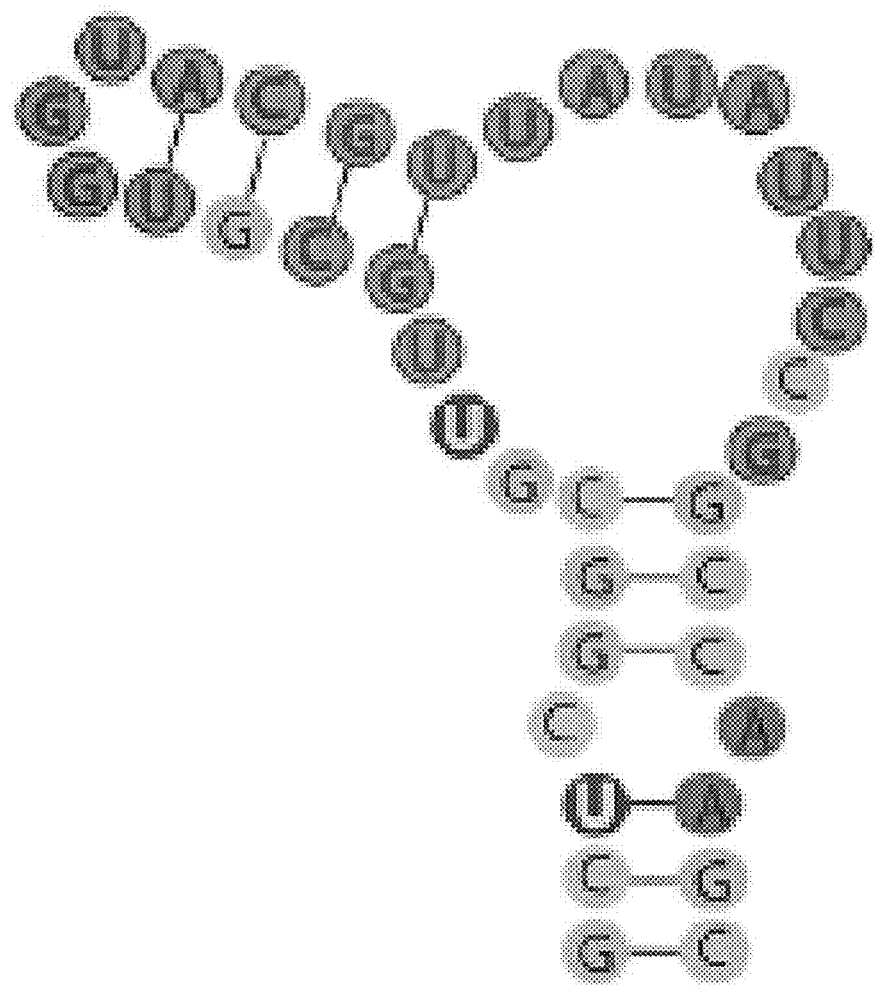
FIG. 12 depicts an alternative aptamer that binds 6R-folinic acid (SEQ ID NO: 4).
Figure 13:
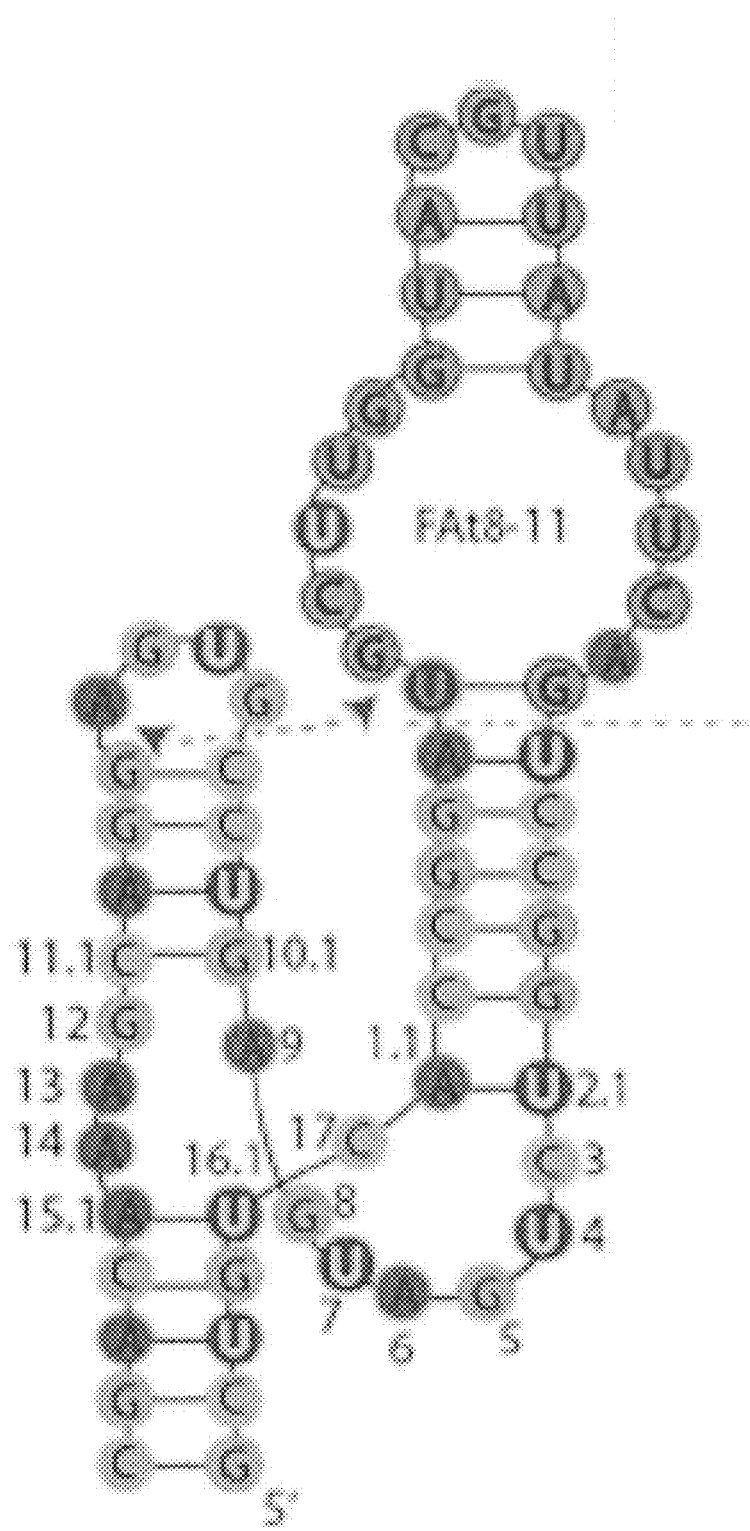
FIG. 13 depicts a new 6R folinic acid RNA control device (SEQ ID NO: 5).
Figure 14:
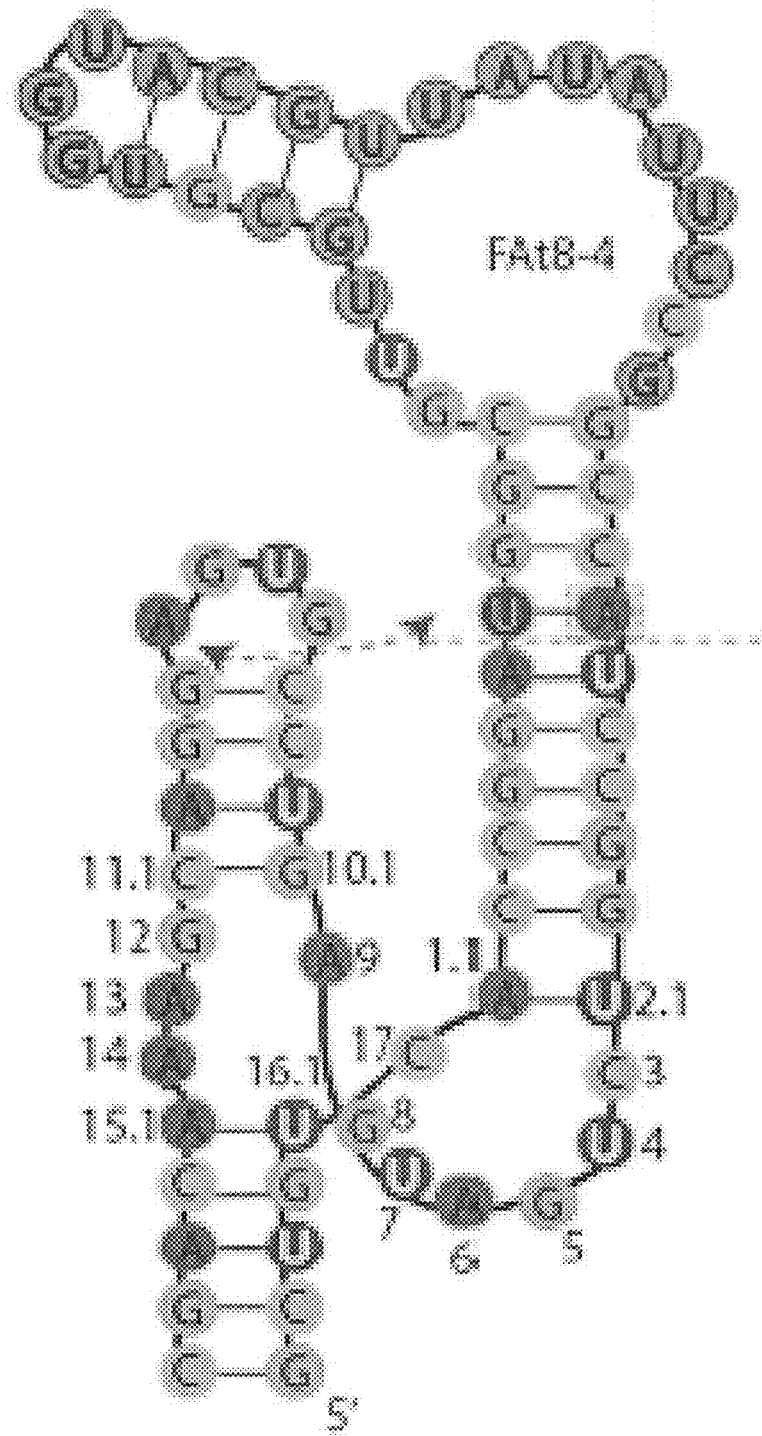
FIG. 14 depicts an alternative 6R folinic acid RNA control device (SEQ ID NO: 6).
Figure 15:
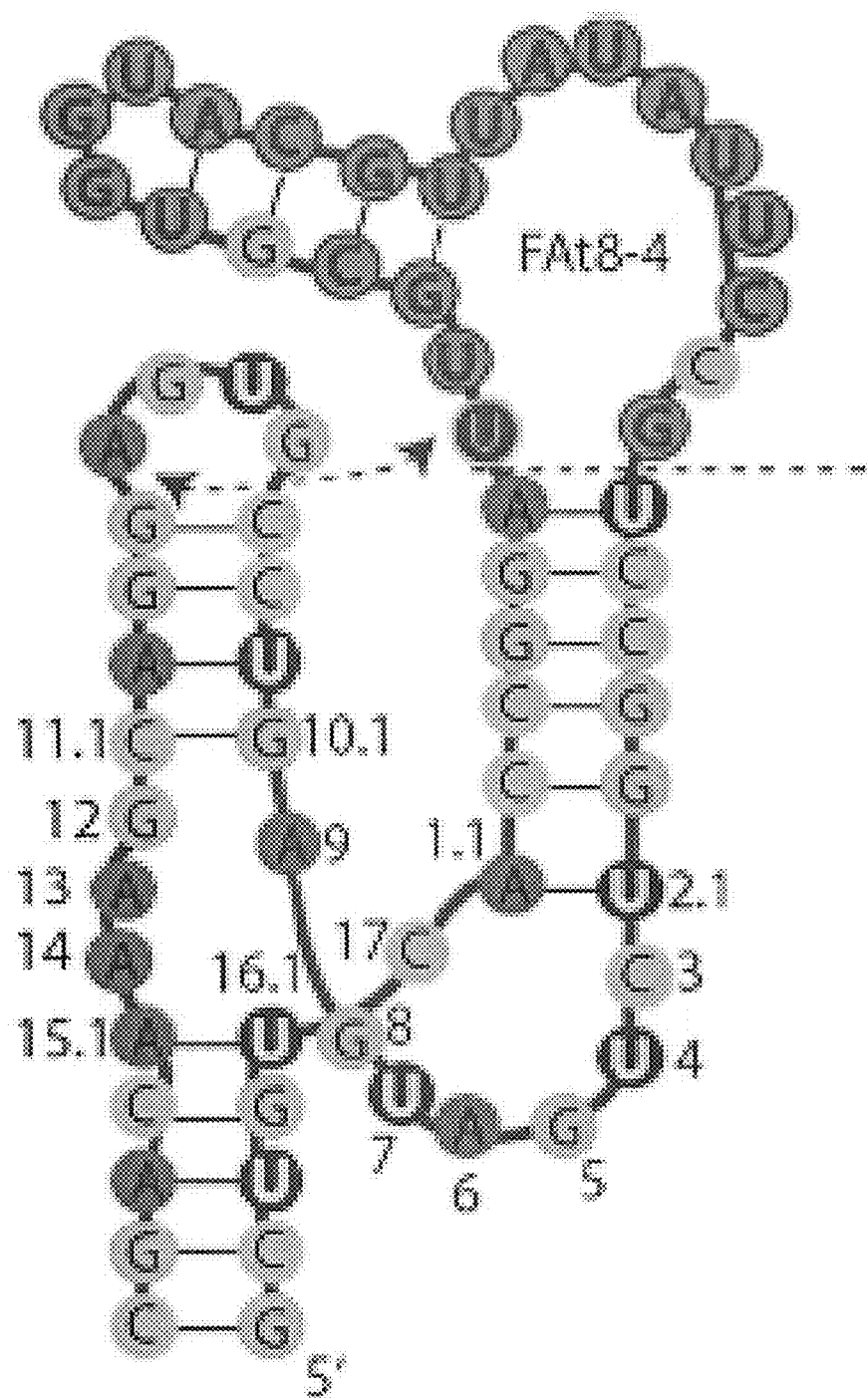
FIG. 15 depicts a still further alternative 6R folinic acid RNA control device (SEQ ID NO: 7).

FIG. 7 shows calculated graphs for effector function (E), number of target cells (nT), number of CAR receptors (nR), and number of CAR receptor-target cell interactions (nRT) versus time as calculated by the program in python code at the end of this specification. Maximal effector function (E) can be reached at time 0.7 despite the fact that the CAR receptors are engaged with antigen throughout the time of the simulation. The python program at the end of the specification can be used with different parameters of number of target cells (nT), number of CAR receptors (nR), and number of CAR receptor-target cell interactions (nRT) to model maximal effector function.

FIG. 7 shows a chart looking at effector activity as a function of CAR copy number, number of target antigens (epitopes), and CAR binding affinity for its antigen (epitope). Optimal CAR activity can be obtained when the variables of CAR copy number, CAR affinity for antigen, and copy number of target epitopes are coordinated to produce a desired amount of effector activity in the cell. The control devices can control CAR copy number to maintain the amount of effector function in the optimal CAR activity range of FIG. 7. As the copy number of target epitope decreases (as target cells are killed) the CAR copy number may be increased to compensate for the reduced amount of target antigen available to bind to the CARs and activate them.

The desired amount of CAR expression can be cycled so the eukaryotic cell (or population of eukaryotic cells) goes through periods of on (activation of cell and effector function) and off (no activation—down regulation of inhibitor receptors, inhibitor activity, and/or dysfunction). The desired amount of CAR expression can be cycled so the activity of cells induced by the CAR eukaryotic cell is cycled, e.g., cells activated by cytokines expressed by the eukaryotic cell with the CAR are cycled (and other immune cells that are activated by the eukaryotic cell). The T lymphocytes and/or natural killer cells can be engineered to knock out inhibitory receptor expression or knock out other factors that cause dysfunction and/or exhaustion, including for example, PD-1, CTLA-4, TIM-3, LAG-3, T-bet and/or Blimp-1. Cycling of CAR expression along with activated and deactivated states can be done on a population basis. Cycling of CAR expression along with activated and deactivated states can be done for individual eukaryotic cells.

Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) can be used for genetically engineering T-cells for cancer immunotherapy. When used for some immunotherapy applications, leukocytes are removed from a patient through leukopheresis and T-lymphocytes are preferentially sorted and saved. T-lymphocytes are subjected to lentiviral or retroviral introduction (or other means of nucleic acid introduction) of the transgene that encodes the Smart CAR, DE-CAR, RDE-CAR, Smart-DE-CAR, Smart-RDE-CAR, DE-RDE-CAR, Smart-DE-RDE-CAR, and/or Side-CAR, expanded to target therapeutic cell concentrations and infused into the patient, resulting in an autologous treatment with little graft vs host complications. Although CARs have been shown to be very effective at achieving and sustaining remissions for refractory/relapsed acute lymphoblastic leukemia (Maude et al., NEJM, 371: 1507, 2014, which is incorporated by reference in its entirety for all purposes), dangerous side effects related to cytokine release syndrome (CRS), tumor lysis syndrome (TLS), B cell aplasia or "on-tumor, off-target" toxicities occur. Modulating CAR expression via the incorporation of DEs, RDEs, RNA control devices, and/or Side-CARs in the Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) can control these toxicities. Modulating CAR expression via the incorporation of DEs, RDEs, RNA control devices, and/or Side-CARs in the Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) can also minimize exhaustion, dysfunction and/or inhibition of the T-lymphocyte (or natural killer cell) while providing a desired level of effector function.

T-cells can comprise CARs, DE-CARs, RDE-CARs and/or Side-CARs with integrated RNA control devices. Combinational Smart DE-CAR, Smart-RDE-CAR, and/or Smart Side-CAR T-cells can be used, wherein independent T-cells express orthogonal Smart CAR(s), DE-CAR(s), RDE- CAR(s), Smart-RDE-CAR(s), DE-RDE-CAR(s), Smart-DE-CAR(s), Smart-DE-RDE-CAR(s) and/or Side-CAR(s), that target distinct tumor-associated antigens (TAAs). Targeting multiple TAAs simultaneously can direct a greater CTL response against the primary tumor or metastases and prevent relapse. A potential disadvantage of using CAR, DE-CAR and/or Side-CAR polypeptide T-cells is that there may be a higher probability of eliciting on-target, off-tumor effects, leading to toxicity. The coupling of DEs, RDEs, RNA control devices, and/or Side-CARs to CARs in Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) T-cells mitigates the toxicity concern while enabling the stronger response and relapse prevention of Smart CAR, DE-CAR, RDE-CAR, Smart-DE-CAR, Smart-RDE-CAR, DE-RDE-CAR, Smart-DE-RDE-CAR, and/or Side-CAR T-cells. Smart-DE-CAR and/or Side-CAR T-cells can be controlled by multiple ligands. The DE, RDE, RNA control devices, and Side-CARs can be used in combinational Smart CAR, DE-CAR, RDE-CAR, Smart-DE-CAR, Smart-RDE-CAR, DE-RDE-CAR, Smart-DE-RDE-CAR, and/or Side-CAR T-cells are specific for different ligands, or combinations of ligands, such that expression cross-talk is minimized or eliminated. The Smart CAR, DE-CAR, RDE-CAR, Smart-DE-CAR, Smart-RDE-CAR, DE-RDE-CAR, Smart-DE-RDE-CAR, and/or Side-CAR T-cells can be used against a single tumor by targeting different tumor-associated surface antigens. These Smart CAR, DE-CAR, RDE-CAR, Smart-DE-CAR, Smart-RDE-CAR, DE-RDE-CAR, Smart-DE-RDE-CAR, and/or Side-CAR T-cells can be used against a single tumor by targeting the same tumor-associated surface antigen, with different transmembrane, hinge, receptor, costimulatory elements, other aspects of the Smart CAR, DE-CAR, RDE-CAR, Smart-DE-CAR, Smart-RDE-CAR, DE-RDE-CAR, Smart-DE-RDE-CAR, and/or Side-CAR or combinations thereof. The Smart CAR, DE-CAR, RDE-CAR, Smart-DE-CAR, Smart-RDE-CAR, DE-RDE-CAR, Smart-DE-RDE-CAR, and/or Side-CAR T-cells can be used against clonally heterogeneous tumor types, wherein each population of Smart CAR, DE-CAR, RDE-CAR, Smart-DE-CAR, Smart-RDE-CAR, DE-RDE-CAR, Smart-DE-RDE-CAR, and/or Side-CAR T-cell is specific for a particular TAA. The relative populations of Smart CAR, DE-CAR, RDE-CAR, Smart-DE-CAR, Smart-RDE-CAR, DE-RDE-CAR, Smart-DE-RDE-CAR, and/or Side-CAR T-cells can be controlled. Combinations of ligands can be dosed to induce expression of a specific population of Smart CAR, DE-CAR, RDE-CAR, Smart-DE-CAR, Smart-RDE-CAR, DE-RDE-CAR, Smart-DE-RDE-CAR, and/or Side-CAR T-cells. Universal Smart CAR, DE-CAR, RDE-CAR, Smart-DE-CAR, Smart-RDE-CAR, DE-RDE-CAR, Smart-DE-RDE-CAR, and/or Side-CAR T-cells can be used. Such CAR T-cells are single T-cells that comprise more than one Smart CAR, DE-CAR, RDE-CAR, Smart-DE-CAR, Smart-RDE-CAR, DE-RDE-CAR, Smart-DE-RDE-CAR, and/or Side-CAR or more than one means for Smart CAR, DE-CAR, RDE-CAR, Smart-DE-CAR, Smart-RDE-CAR, DE-RDE-CAR, Smart-DE-RDE-CAR, and/or Side-CAR expression.

Smart CAR, DE-CAR, RDE-CAR, Smart-DE-CAR, Smart-RDE-CAR, DE-RDE-CAR, Smart-DE-RDE-CAR, Side-CAR and/or universal-CARs can be designed to include receptors against antigens that are of bacterial, fungal or viral origin. Because Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) can be utilized to fight infections, which are a source of toxicity in immunocompromised patients, such anti-pathogen Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) can be used in conjunction Smart CAR, DE-CAR, RDE-CAR, Smart-DE-CAR, Smart-RDE-CAR, DE-RDE-CAR, Smart-DE-RDE-CAR, and/or Side-CAR T-cell therapy specific for a TAA.

A eukaryotic cell can bind to a specific antigen via the CAR, DE-CAR, and/or Side-CAR polypeptide causing the CAR, DE-CAR, and/or Side-CAR polypeptide to transmit a signal into the eukaryotic cell, and as a result, the eukaryotic cell can be activated and so express an appropriate RDE-transgene. The activation of the eukaryotic cell expressing the Smart CAR, DE-CAR, RDE-CAR, Smart-DE-CAR, Smart-RDE-CAR, DE-RDE-CAR, Smart-DE-RDE-CAR, and/or Side-CAR is varied depending on the kind of a eukaryotic cell and the intracellular element of the Smart CAR, DE-CAR, RDE-CAR, Smart-DE-CAR, Smart-RDE-CAR, DE-RDE-CAR, Smart-DE-RDE-CAR, and/or Side-CAR. The eukaryotic cell can express a RDE transcript that poises the cell for effector function upon stimulation of the eukaryotic cell through a Smart CAR, DE-CAR, RDE-CAR, Smart-DE-CAR, Smart-RDE-CAR, DE-RDE-CAR, Smart-DE-RDE-CAR, and/or Side-CAR.

A eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide can be used as a therapeutic agent to treat a disease. The therapeutic agent can comprise the eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide as an active ingredient, and may further comprise a suitable excipient. Examples of the excipient include pharmaceutically acceptable excipients for the composition. The disease against which the eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide is administered is not particularly limited as long as the disease shows sensitivity to the eukaryotic cell and/or the product of the RDE-transgene.

Examples of diseases that can be treated include a cancer (blood cancer (leukemia), solid tumor (ovarian cancer) etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis, other immune mediated diseases such as neurodegenerative diseases like Alzheimer's or Parkinson's, and metabolic diseases like diabetes. A receptor (e.g., a CAR) can target the eukaryotic cell to the diseased cell(s) and when the receptor binds to its target at the diseased cell(s) the receptor can send a signal into the eukaryotic cell leading to expression of the RDE-transgene. The RDE-transgene encodes a polypeptide that is useful in treating or killing the diseased cell(s). A cancer and/or solid tumor can be treated with a eukaryotic cell expressing receptor that binds to a tumor associated (or cancer associated) antigen, such as those described above. When the receptor binds to the tumor associated antigen the receptor sends a signal into the cell that causes the RDE-transgene to be expressed (e.g., the signal effects an RDE binding protein leading to expression of the RDE-transcript). The RDE-transcript can encode a polypeptide that activates the eukaryotic cell so that the eukaryotic cell treats the cancer and/or the RDE-transcript encodes a polypeptide that itself treats the cancer (e.g., a cytotoxic polypeptide).

An autoimmune disease (e.g., pemphigus vulgaris, lupus erythematosus, rheumatoid arthritis, multiple sclerosis, Crohn's disease) can be treated with a eukaryotic cell expressing a RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide that binds to the immune proteins associated with the autoimmune disease. The receptor or targeting polypeptide can trigger expression of the RDE-transgene that encodes a polypeptide useful in treating the autoimmune disease (e.g., the polypeptide can regulate the cells causing the autoimmune disease or kill these cells). The eukaryotic cell expressing the RDE-transgene or RDE transcript, and receptor or targeting polypeptide can target cells that make an antibody involved with the autoimmune disease (e.g., the RDE-transgene can encode a polypeptide that kills the antibody producing cells or that inhibits the production of antibody by these cells). The eukaryotic cell expressing the RDE-transgene or RDE transcript, and receptor or targeting polypeptide can target T-lymphocytes involved with the autoimmune disease (e.g., the RDE-transgene can encode a polypeptide that kills the target T-lymphocytes or that regulates the activity of the T-lymphocytes).

Eukaryotic cells expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide can be used as a therapeutic agent to treat an allergy. Examples of allergies that can be treated include, for example, allergies to pollen, animal dander, peanuts, other nuts, milk products, gluten, eggs, seafood, shellfish, and soy. The eukaryotic cell expressing the RDE-transgene or RDE transcript, and receptor or targeting polypeptide can target cells that make an antibody which causes the allergic reaction against, for example, pollen, animal dander, peanuts, other nuts, milk products, gluten, eggs, seafood, shellfish, and soy. The targeted cells can be one or more of B-cells, memory B-cells, plasma cells, pre-B-cells, and progenitor B-cells. Targeted cells can also include T-lymphocytes which cause the allergic reaction against, for example, pollen, animal dander, peanuts, other nuts, milk products, gluten, eggs, seafood, shellfish, and soy. Eukaryotic cells expressing the RDE-transgene or RDE transcript, and receptor or targeting polypeptide can bind to the idiotypic determinant of the antibody or T-cell receptor.

The eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide can be administered for treatment of a disease or condition. For example, the eukaryotic cell can be utilized to treat an infectious disease. The eukaryotic cell can express a receptor or targeting polypeptide that binds to an antigen found on the infectious disease causing agent or a cell infected with such an agent. The receptor or targeting polypeptide binds the antigen associated with the infectious disease and sends a signal into the eukaryotic cell that leads to expression of the RDE-transgene. The RDE-transgene encodes a product that can activate the eukaryotic cell for treating the infectious disease (e.g., the eukaryotic cell can produce a cytotoxic polypeptide or a cytokine that activates immune cells). The RDE-transgene can also encode a polypeptide that itself is a cytotoxic polypeptide or a cytokine. The eukaryotic cell can also be utilized for prevention of an infectious disease (used prophylactically), for example, after bone marrow transplantation or exposure to radiation, donor lymphocyte transfusion for the purpose of remission of recurrent leukemia, and the like.

The therapeutic agent comprising the eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

The RDE-transgene or RDE transcript, and optionally, Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide can be used with a T-lymphocyte that has aggressive anti-tumor properties, such as those described in Pegram et al, CD28z CARs and armored CARs, 2014, Cancer J. 20(2):127-133, which is incorporated by reference in its entirety for all purposes. The RDE transcript can encode a polypeptide that causes aggressive anti-tumor properties in the T-lymphocyte.

A transgene, a CAR, DE-CAR, and/or Side CAR polypeptides can be controlled by an RDE from the 3'-UTR of the gene encoding IL-2 or the 3'-UTR of IFN-γ. These RDEs can be modified to inactivate microRNA sites found in the RDE. Using these control elements makes expression of the CAR, DE-CAR, Side-CAR, and/or transgene sensitive to changes in the glycolytic state of the host cell through the interaction of the RDE with glyceraldehyde-3-phosphate dehydrogenase (GAPDH). When the host cell is in a quiescent state a large proportion of the GAPDH is not involved in glycolysis and is able to bind to the RDE resulting in reduced translation of the transcript encoding the CAR, DE-CAR, Side-CAR, and/or transgene polypeptides. When the host cell is induced to increase glycolysis, e.g., by providing the host cells with glucose, or other small molecules that will increase glycolytic activity, GAPDH becomes enzymatically active and is not able to bind to the RDE. The reduction in GAPDH binding to the RDE increases translation of the transcripts (e.g., by increasing half-life of the transcript and/or by increasing the translation rate) encoding the CAR, DE-CAR, Side-CAR, or other transgene. The glycolytic activity of GAPDH can be increased by increasing the amount and/or activity of triose isomerase. The host cell can be induced to over-express a recombinant triose isomerase, and this over-expression increases the glycolytic activity of GAPDH. A glycolysis inhibitor can be added to decrease expression of the transcript with the RDE. Such glycolysis inhibitors incfude for example, rapamycin, 2-deoxyglucose, 3-bromophyruvic acid, iodoacetate, fluoride, oxamate, ploglitazone, dichloroacetic acid, quinones, or other metabolism inhibitors such as, for example, dehydroepiandrosterone. Expression from the RDE controlled transcript can be increased by the addition of GAPDH (or other RDE binding protein) inhibitor that inhibits binding of the RDE by GAPDH (or other RDE binding protein). Such GAPDH inhibitors include, for example, CGP 3466B maleate or Heptelidic acid (both sold by Santa Cruz Biotechnology, Inc.), pentalenolactone, or 3-bromopyruvic acid.

Constructs encoding transcripts with RDEs can be expressed in eukaryotic cells to bind to RDE binding proteins and so reduce the ability of those RDE binding proteins to interact with native transcripts in the cell. The recombinant transcripts can compete for binding of RDE binding proteins and this can reduce the inhibition and/or activation of native transcripts within the eukaryotic cell by the RDE binding proteins. The constructs encoding transcripts with the RDEs can be used in this way to change when and how native transcripts are expressed in the eukaryotic cell. The eukaryotic cell can be a T-cell, natural killer cell, or B-cell and the recombinant transcript has RDEs that are shared with cytokine or cytotoxic transcripts (e.g., in their 3' untranslated regions). The recombinant transcript can compete for binding with the RDE binding proteins (e.g., GAPDH and/or other glycolytic enzymes described above) that regulate expression of the cytokine or cytotoxic polypeptide and change the threshold (e.g., glycolysis activity for GAPDH) needed to express the cytokine or cytotoxic polypeptide. This can be used to create super T-cell (aka Angry T-cells or Hornet T-cells) that will secrete higher amounts of cytokines and/or cytotoxic proteins (greater $C_{max}$) in response to stimulation of the immune cell (e.g., through a CAR or T-cell receptor). T-cells can be reprogrammed with a recombinant transcript encoding an RDE from an IL-2 transcript so that when the T-cell is stimulated by its T-cell receptor it produces more IL-2 and other effector polypeptides with faster kinetics. These reprogrammed T-cells can also produce other inflammatory cytokines and cytotoxic polypeptides (e.g., granzymes and/or performs) in larger amounts and with faster kinetics. Reprogramming T-cells and natural killer cells into such Angry/Hornet states can be useful for treating disease and disorders, including, for example, tumors, other cancers, and infectious diseases.

A subject can be diagnosed for certain diseases by identifying changes in the subject's RDEs. Such changes can cause gain or loss of function to the RDE. For example, deletions, chromosomal rearrangements, and certain base substitutions can cause the RDE to lose function (e.g., RNA binding proteins that normally interact with the RDE no longer bind). Such loss of function changes can alter expression of the transcript and result in aberrant expression. Detection of aberrant RDEs can be done using next generation nucleic acid sequencing, protein-RNA binding assays or RNA binding protein trap methods such as those described in Castello et al., Molc. Cell 63:696-710 (2016), which is incorporated by reference in its entirety for all purposes. These RNA binding assays can be used to diagnose change in function of a subject's RDEs. This aberrant expression can result in disease states such as cancer including, for example, adult T-cell leukemia/lymphoma, diffuse large B-cell lymphoma, and stomach adenocarcinoma (these cancers have variants in which the RDEs of the 3'-UTR for PD-L1 is altered leading to over expression of PD-L1) (Kataoka K et al, Nature (2016) 534:402, doi:10.1038/nature18294, which is incorporated by reference in its entirety for all purposes); inflammatory disease; autoimmune disease, such as, for example, systemic lupus erythematosus, type I diabetes, celiac disease (de Jong et al., Genes and Immunity (2016) 17, 75-78, which is incorporated by reference in its entirety for all purposes) (changes in the 3'-UTR of CTLA-4 that increased the length of the RDE correlated with autoimmunity), and rheumatoid arthritis (Tsuzaka et al. Modern Rheumatol. (2002) 12:167-173, which is incorporated by reference in its entirety for all purposes) (alternative splicing changed the RDE for T-cell receptor ζ chain and resulted in down regulation of expression); and neurological disorders and pain disorders (Foulkes and Wood, PLoS Genetics (2008) 4(7):e1000086, which is incorporated by reference in its entirety for all purposes).

Aberrant RDEs of a subject can be detected using sequencing technologies, amplification methods, hybridization based technologies, and other methods for detecting sequence changes. The RDEs can be detected by analysis of the subject's nucleic acids (mRNA and/or DNA). Sequencing technologies include, for example, sanger sequencing, other chain termination sequencing methods, Maxam and Gilbert sequencing, Polony sequencing, SOLID sequencing (sequencing by ligation), single molecule sequencing (e.g., Pacific Biosciences), ion torrent sequencing, pyrosequencing (e.g., 454 Life Sciences), sequencing by synthesis (Illumina), nanopore sequencing, etc. Amplification methods include, for example, polymerase chain reaction (PCR), real-time PCR, transcription mediated amplification technologies, reverse transcriptase PCR, ligase chain reaction, strand displacement amplification, cleavase invader, etc. Hybridization methods include, for example, Southerns, Northerns, DNA-DNA hybridization, DNA-RNA hybridization, RNA-RNA hybridization, fluorescent in situ hybridization, etc. In other aspects, changes in the interaction of RDEs with RDE binding proteins are identified using protein-RNA binding assays or RNA binding protein trap methods such as those described in Castello et al., Molc. Cell 63:696-710 (2016), which is incorporated by reference in its entirety for all purposes.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1. Control of T-Cell Effector Activity with a Smart-CAR

A Smart Car is made using the third generation anti-CD20 CAR cassette described in Budde 2013 (Budde et al. PLoS1, 2013 doi:10.1371/journal.pone.0082742, which is hereby incorporated-by-reference in its entirety for all purposes), and the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the 3XL2bulge9 control device is engineered into the anti-CD20 CAR cassette in an appropriate expression vector.

This anti-CD20 Smart CAR is transfected by routine methods into T-cells (Jurkat cells and/or primary human T-cells), and stable populations of T-cells are selected using appropriate antibiotics (or other selection schemes). T-cell populations with anti-CD20 Smart CARs (CD20$^-$/CD22$^-$/CD3$^+$) are activated by co-incubation with anti-CD3/CD28 beads.

Activated anti-CD20 Smart CAR T-cells are co-cultured with CD20$^+$/CD22$^+$/CD3$^-$ Ramos target cells at Smart CAR T-cell:Ramos target ratios of 2:1, 5:1, and 10:1. Ligand for the RNA control device, theophylline is added to the culture medium at concentrations in the range of 500 μM to 1 mM (lower or greater concentrations can be used to titrate Smart-CAR activity to the desired level). The Smart-CAR T-cells and the Ramos cells are grown together for 48 hours. Cultures are washed, and then stained with anti-CD22 and anti-CD3 reagents, followed by counting of CD22$^+$ (Ramos target cells) and CD3$^+$ cells (Smart CAR T-cells). These measurements will identify the target cell killing rate (e.g., half-life) and the proliferation rate of the Smart-CAR T-cells at different levels of Smart-CAR expression.

Example 2. Control of T-Cell Effector Activity with Combination Smart-CARs in a Human Subject Nucleic acids encoding orthogonal Smart CARs that have specificity for distinct TAAs and respond to distinct small molecule ligands are constructed and are packaged into lentiviral vectors. Each of these Smart CARs demonstrate in vitro cytotoxic T-cell effector function and antigen-dependent expansion in response to cognate ligand exposure, and individually have known therapeutic windows in human patients.

To treat a human subject with tumors that express the defined set of multiple TAAs that are recognized by this Smart CAR pool, autologous T-cells are harvested from a patient's peripheral blood by apheresis and transduced ex vivo with lentivirus encoding the cognate Smart CARs, either individually or in pools. Expanded Smart CAR CD4+ and/or CD8+ T-cells are then adoptively transferred back into the patient. Each Smart CAR is individually activated with its own cognate small molecule ligand to initiate tumor recognition and elimination. As each Smart CAR is individually controlled, therapeutic windows for each Smart CAR are adjusted to enforce maximal graft vs. tumor response, with tolerable graft vs. host response. If the escape phase of tumor immunoediting is reached, the Smart CAR targeting the lost TAA is inactivated by removal of its cognate ligand to limit further graft vs. host response for a Smart CAR that no longer provides graft vs. tumor benefits. By controlling Smart CAR toxicity and parallelizing a distributed attack on TAAs quickly, durable remissions for any tumor type are achieved.

Example 3. Control of T-Cell Effector Activity with a DE-CAR

A DE-CAR is made using the anti-CD20 CAR cassette described in Budde 2013 (Budde et al. PLoS1, 2013 doi: 10.1371/journal.pone.0082742, which is hereby incorporated-by-reference in its entirety for all purposes), and the destabilizing element (DE) ecDHFR described in Iwamoto 2010 (Iwamoto et al. Chemistry and Biology, 2010 doi: 10.1016/j.chembiol.2010.07.009, which is hereby incorporated by reference in its entirety for all purposes). The DE-CAR also can encode the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the DE of mutant scDHFR is engineered into the anti-CD20 CAR cassette in an appropriate expression vector. Alternatively, a nucleic acid encoding the 3XL2bulge9 control device is further engineered into the DE-anti-CD20 CAR cassette.

This anti-CD20 DE-CAR is transfected by routine methods into T-cells (Jurkat cells and/or primary human T-cells), and stable populations of T-cells are selected using appropriate antibiotics (or other selection schemes). T-cell populations with anti-CD20 DE-CARs or anti-CD20 Smart-DE-CARs (CD20$^-$/CD22$^-$/CD3$^+$) are activated by co-incubation with anti-CD3/CD28 beads.

Activated anti-CD20 DE-CAR T-cells or anti-CD20 Smart-DE-CAR T-cells are co-cultured with CD20$^+$/CD22$^+$/CD3$^-$ Ramos target cells at DE-CAR T-cell (or Smart-DE-CAR T-cell):Ramos target ratios of 2:1, 5:1, and 10:1. Ligand for the DE, trimethoprim, and/or ligand for the RNA control device, theophylline, is added to the culture medium at concentrations in the range of 500 μM to 1 mM (lower or greater concentrations can be used to titrate Smart-CAR activity to the desired level). The DE-CAR T-cells or Smart-DE-CAR T-cells and the Ramos cells are grown together for 48 hours. Cultures are washed, and then stained with anti-CD22 and anti-CD3 reagents, followed by counting of CD22$^+$ (Ramos target cells) and CD3$^+$ cells (DE-CAR and/or Smart-DE-CAR T-cells). These measurements will identify the target cell killing rate (e.g., half-life) and the proliferation rate of the Smart-CAR T-cells at different levels of Smart-CAR expression.

Example 4. Increasing T-Cell Effector Activity with a Smart-CAR

A Smart Car is made using the third generation anti-CD19 CAR cassette described in WO 2012/079000, which is hereby incorporated-by-reference in its entirety for all purposes), and the RNA control device, 3XL2bulge9 (Win and Smolke 2007 Proc. Natl. Acad. Sci. 104 (36): 14283-88, which is hereby incorporated by reference in its entirety for all purposes). A nucleic acid encoding the 3XL2bulge9 control device is engineered into the anti-CD19 CAR cassette in an appropriate expression vector.

The anti-CD19 Smart CAR and anti-CD19 CAR constructs are transfected by routine methods into different populations of T-cells (Jurkat cells and/or primary human T-cells), and stable populations of T-cells are selected using appropriate antibiotics (or other selection schemes). T-cell populations with anti-CD19 Smart CARs (CD19$^7$/CD22$^-$/CD3$^+$) and T-cell populations with anti-CD19 CARs (CD19$^-$/CD22$^-$/CD3$^+$) are activated by co-incubation with anti-CD3/CD28 beads.

Activated anti-CD19 Smart CAR T-cells are co-cultured with CD19$^+$/CD22$^+$/CD3$^-$ Ramos target cells at Smart CAR T-cell:Raji target ratios of 2:1, 5:1, and 10:1. Ligand for the RNA control device, theophylline is added to the culture medium at concentrations in the range of 2 μM to 2 mM (2 μM, 10 μM, 20 μM, 100 μM, 200 μM, 1 mM, and 2 mM). The Smart-CAR T-cells and the Raji cells are grown together for 48 hours. Cultures are washed, and then stained with anti-CD22 and anti-CD3 reagents, followed by counting of CD22$^+$ (Raji target cells) and CD3$^+$ cells (Smart CAR T-cells). These measurements will identify the target cell killing rate (e.g., half-life) and the proliferation rate of the Smart-CAR T-cells at different levels of Smart-CAR expression.

Activated anti-CD19 Smart CAR T-cells are co-cultured with CD19$^+$/CD22$^+$/CD3$^-$ Ramos target cells at Smart CAR T-cell:Raji target ratios of 2:1, 5:1, and 10:1. Ligand for the RNA control device, theophylline is added to the culture medium at concentrations in the range of 2 µM to 2 mM (2 µM, 10 µM, 20 µM, 100 µM, 200 µM, 1 mM, and 2 mM). The Smart-CAR T-cells and the Raji cells are grown together for 48 hours. Samples from culture media are taken and tested for IL-2 by ELISA.

As a control activated anti-CD19 CAR T-cells are co-cultured with CD19+/CD22+/CD3− Raji target cells at CAR T-cell:Raji target ratios of 2:1, 5:1, and 10:1. Ligand for the RNA control device, theophylline is added to the culture medium at concentrations in the range of 2 µM to 2 mM (2 µM, 10 µM, 20 µM, 100 µM, 200 µM, 1 mM, and 2 mM). The CAR T-cells and the Ramos cells are grown together for 48 hours. Cultures are washed, and then stained with anti-CD22 and anti-CD3 reagents, followed by counting of CD22+ (Raji target cells) and CD3+ cells (CAR T-cells). These measurements will identify the target cell killing rate (e.g., half-life) and the proliferation rate of the CAR T-cells at different levels of CAR expression.

As a control, activated anti-CD19 CAR T-cells are co-cultured with CD19+/CD22+/CD3− Raji target cells at CAR T-cell:Raji target ratios of 2:1, 5:1, and 10:1. Ligand for the RNA control device, theophylline is added to the culture medium at concentrations in the range of 2 µM to 2 mM (2 µM, 10 µM, 20 µM, 100 µM, 200 µM, 1 mM, and 2 mM). The CAR T-cells and the Raji cells are grown together for 48 hours. Samples from culture media are taken and tested for IL-2 by ELISA.

Example 5. Target Cell Killing by CD8+ T-Lymphocytes with a Smart-CAR

A Smart Car was made using the anti-CD19 CAR described in WO 2012/079000, which is hereby incorporated-by-reference in its entirety for all purposes, and the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the 3XL2bulge9 control device was engineered into the anti-CD19 CAR cassette in an expression vector.

The anti-CD19 Smart CAR and anti-CD19 CAR constructs are transfected by routine methods into different populations of T-cells (Jurkat cells and/or primary human T-cells), and stable populations of T-cells are selected using appropriate antibiotics (or other selection schemes). T-cell populations with anti-CD19 Smart CARs (CD20−/CD22−/CD3+) and T-cell populations with anti-CD19 CARs (CD20−/CD22−/CD3+) are activated by co-incubation with anti-CD3/CD28 beads.

T-cells with anti-CD19 Smart CARs or anti-CD19 CARs were incubated with theophylline at 0, 75 and 250 µM for 72 hours. Activated anti-CD19 Smart CAR T-cells or anti-CD19 CAR T-cells were co-cultured with CD19+/CD22+/CD3− Raji target cells at Smart CAR T-cell:Raji target ratios of 2:1, 5:1, and 10:1. Ligand for the RNA control device, theophylline is maintained in the culture medium at concentrations of 0 µM, 75 µM, and 250 µM. The Smart-CAR T-cells or CAR T-cells and the Raji cells are grown together for 18 hours. Cultures are washed, and then stained with anti-CD22 and anti-CD3 reagents, followed by counting of CD22+ (Raji target cells) and CD3+ cells (Smart CAR T-cells).

Figure 6:
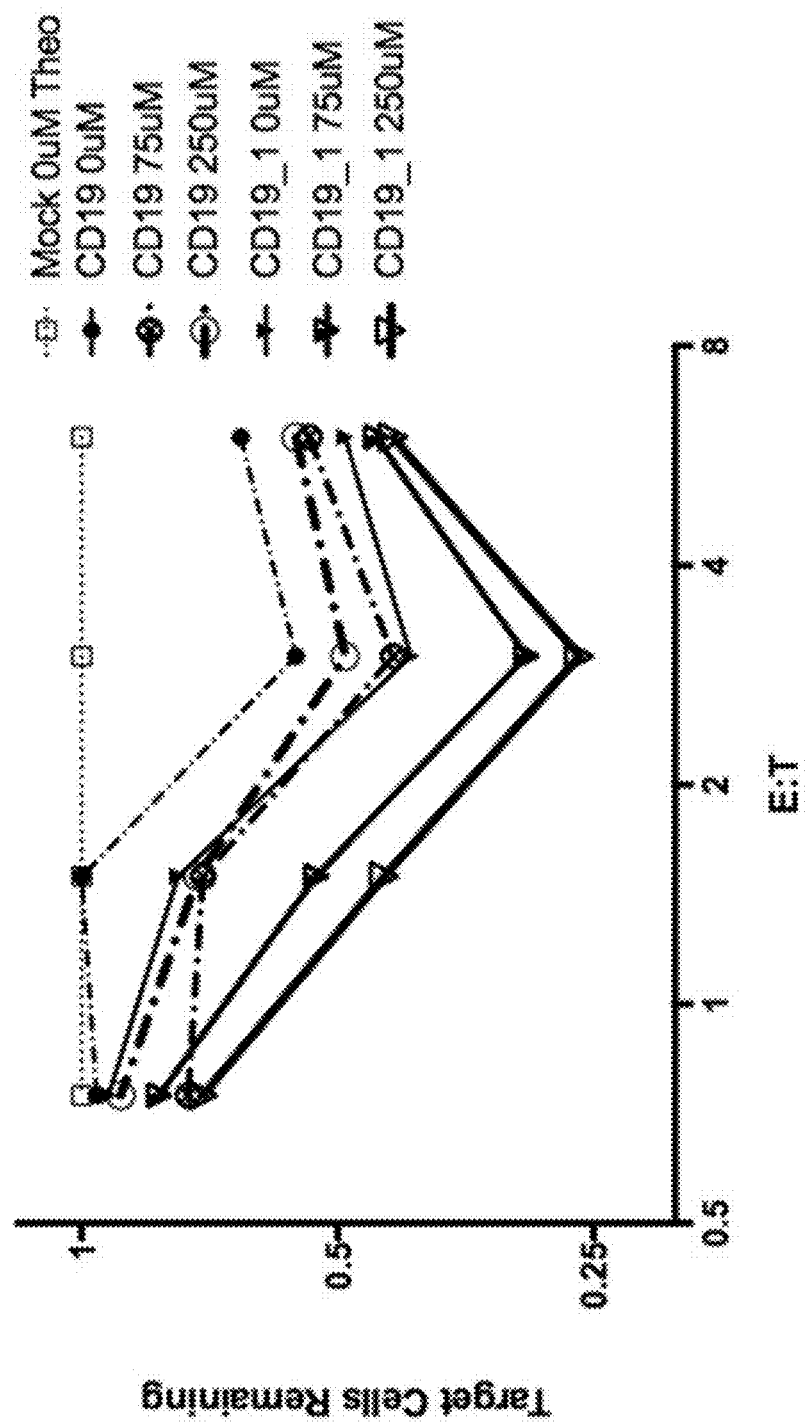
FIG. 6 provides a graph of cell killing activity for anti-CD19 CAR, CD8+ T-cells over time in the presence of different concentrations of theophylline (ligand for the RNA control device).

The results of this experiment are depicted in FIG. 6, which shows target cell killing graphed against time with individual curves for each theophylline concentration and for T-lymphocytes with anti-CD19 Smart CARs or T-lymphocytes with anti-CD19 CARs. This figure demonstrates an improvement in target cell killing with the theophylline controlled Smart CARs over the constitutively expressed CAR. The improvement was about 2 fold at 250 µM theophylline, and both 75 µM and 250 µM theophylline improved target cell killing over the constitutively expressed CAR. Both theophylline concentrations also showed about a two fold increase in cell killing over T-lymphocytes with the anti-CD19 Smart CAR grown without theophylline (these cells also killed target cells showing some basal level of CAR expression).

Example 6. Reducing T-Lymphocyte Exhaustion Markers for CD8+ T-Lymphocytes with CD-19 CARs A Smart Car was made using the anti-CD19 CAR described in WO 2012/079000, which is hereby incorporated-by-reference in its entirety for all purposes, and the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the 3XL2bulge9 control device was engineered into the anti-CD19 CAR cassette in an expression vector.

The anti-CD19 Smart CAR and anti-CD19 CAR constructs are transfected by routine methods into different populations of T-cells (Jurkat cells and/or primary human T-cells), and stable populations of T-cells are selected using appropriate antibiotics (or other selection schemes). T-cell populations with anti-CD19 Smart CARs (CD19−/CD22−/CD3+) and T-cell populations with anti-CD19 CARs (CD19−/CD22−/CD3+) are activated by co-incubation with anti-CD3/CD28 beads.

T-cells with anti-CD19 Smart CARs or anti-CD19 CARs are incubated with theophylline at 0, 75 and 250 µM for 72 hours. Activated anti-CD19 Smart CAR T-cells or anti-CD19 CAR T-cells are co-cultured with CD19+/CD22+/CD3− Raji target cells at Smart CAR T-cell:Raji target ratios of 2:1, 5:1, and 10:1. Ligand for the RNA control device, theophylline is maintained in the culture medium at concentrations of 0 µM, 75 µM, and 250 µM. The Smart-CAR T-cells or CAR T-cells and the Raji cells are grown together for 18 hours. Cultures are washed, and then stained with anti-CD22 and anti-CD3 reagents, followed by counting of CD22+ (Raji target cells) and CD3+ cells (Smart CAR T-cells). The cells are also stained with anti-PD-1, anti-TIM3 and/or anti-LAG-3 reagents to measure these T-lymphocyte exhaustion markers by ELISA or cell sorting.

The CD-19 Smart CAR T-lymphocytes will have lower levels of the exhaustion markers compared to the constitutively expressed CD-19 CAR T-lymphocytes. This reduction in exhaustion markers may be seen even prior to stimulation of the CD-19 CAR lymphocytes and CD-19 Smart CAR lymphocytes by CD-19 on target Raji cells.

Example 7. Control of T-Cell Effector Activity with an RDE-CAR

A RDE Car is made using the third generation anti-CD19 CAR cassette described in WO 2012/079000, which is hereby incorporated-by-reference in its entirety for all purposes), and the 3'-UTR of the gene encoding IL-2 (NCBI Reference Sequence Number: NM_000586.3), which is hereby incorporated by reference in its entirety for all purposes). A nucleic acid encoding the IL-2 3'-UTR is engineered into the anti-CD19 CAR cassette in an appropriate expression vector. The IL-2, 3'-UTR sequence used was:

(SEQ ID NO: 28)
taattaagtgcttcccacttaaaacatatcaggccttctATTTATTTAaa tATTTAaattttatATTTAttgttgaatgtatggtttgctacctattgta actattattcttaatcttaaaactataaatatggatcttttatgattctt tttgtaagccctaggggctctaaaatggtttcacttATTTAtcccaaaat ATTTAttattatgttgaatgttaaatatagtatctatgtagattggttag taaaactATTTAataaatttgataaatataaa The anti-CD19 RDE CAR and anti-CD19 CAR constructs are transfected by routine methods into different populations of T-cells (primary human T-cells), and stable populations of T-cells are selected using appropriate antibiotics (or other selection schemes). T-cell populations with anti-CD19 RDE CARs (CD19$^-$/CD22$^-$/CD3$^+$) and T-cell populations with anti-CD19 CARs (CD19$^-$/CD22$^-$/CD3$^+$) are activated by co-incubation with anti-CD3/CD28 beads and allowed to return to quiescent state after debeading.

Quiescent anti-CD19 RDE CAR T-cells are co-cultured with CD19$^+$/CD22$^+$/CD3$^-$ Raji target cells at RDE CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The RDE-CAR T-cells and the Raji cells are grown together for 24 hours. Cultures are washed, and then stained with anti-CD22 and anti-CD3 reagents, followed by counting of CD22$^+$ (Raji target cells) and CD3$^+$ cells (Smart CAR T-cells). These measurements will identify the target cell killing rate (e.g., half-life) and the proliferation rate of the RDE-CAR T-cells at different levels of RDE-CAR expression.

Activated anti-CD19 RDE CAR T-cells are co-cultured with CD19$^+$/CD22$^+$/CD3$^-$ Raji target cells at RDE CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The RDE-CAR T-cells and the Raji cells are grown together for 24 hours. Samples from culture media are taken and tested for IL-2 by ELISA.

As a control activated anti-CD19 CAR T-cells are co-cultured with CD19$^+$/CD22$^+$/CD3$^-$ Raji target cells at CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The CAR T-cells and the Raji cells are grown together for 24 hours. Cultures are washed, and then stained with anti-CD22 and anti-CD3 reagents, followed by counting of CD22$^+$ (Raji target cells) and CD3$^+$ cells (CAR T-cells).

As a control, activated anti-CD19 CAR T-cells are co-cultured with CD19$^+$/CD22$^+$/CD3$^-$ Raji target cells at CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The CAR T-cells and the Raji cells are grown together for 48 hours. Samples from culture media are taken and tested for IL-2 by ELISA.

Example 8. Removal of MicroRNA Binding Sites from an RDE

The AU-rich element from the 3'-UTR of IL-2 has mir-181 and mir 186 microRNA binding sites. Different combinations of the microRNA sites were removed from the 3'-UTR of IL-2. When the MIR186 micro-RNA sites were removed from the 3'-UTR of IL-2 the dynamic range of expression from constructs with this UTR increased 50 fold. The modified IL-2, 3'-UTR replaces CTT in the sequence with GAA and is shown below (the new GAA is underlined in the sequence):

(SEQ ID NO: 29)
taattaagtgcttcccacttaaaacatatcaggccttctATTTATTTAaa tATTTAaattttatATTTAttgttgaatgtatggtttgctacctattgta actattattcttaatcttaaaactataaatatggatcttttatgatt<u>GAA</u> tttgtaagccctaggggctctaaaatggtttcacttATTTAtcccaaaat

ATTTAttattatgttgaatgttaaatatagtatctatgtagattggttag taaaactATTTAataaatttgataaatataaa The AU-rich element from the 3'UTR of IFNg also has micro-RNA binding sites characterized as mir-125. The sequence of the IFNg RDE is:

(SEQ ID NO: 30)
tggttgtcctgcctgcaatatttgaattttaaatctaaatctATTTAtta atATTTAacattATTTAtatggggaatatattttagactcatcaatcaa ataagtATTTAtaatagcaacttttgtgtaatgaaaatgaatatctatta atatatgtattATTTAtaattcctatatcctgtgactgtctcacttaatc ctttgttttctgactaattaggcaaggctatgtgattacaaggctttatc tcaggggccaactaggcagccaacctaagcaagatcccatgggttgtgtg tttatttcacttgatgatacaatgaacacttataagtgaagtgatactat ccagttactgccggtttgaaaatatgcctgcaatctgagccagtgcttta atggcatgtcagacagaacttgaatgtgtcaggtgaccctgatgaaaaca tagcatctcaggagatttcatgcctggtgcttccaaatattgttgacaac tgtgactgtacccaaatggaaagtaactcatttgttaaaattatcaatat ctaatatatatgaataaagtgtaagttcacaacta Different combinations of the micro-RNA sites were removed from the 3'UTR of IFNg and tested for increased expression. When the mir125 micro-RNA sites were removed from the 3'-UTR of IFN-γ the expression rate from constructs with this UTR is increased.

Expression of GFP in T-cells, transfected with the RDE-GFP plus the microRNA sites, is compared to expression of GFP in T-cells with the RDE-GFP in which the microRNA sites have been removed, following activation with CD3/CD28 beads for 24 hours. The removal of the microRNA sites increased expression of the GFP by a factor of between 2-5 after 24 hours, relative to the cells with microRNA sites.

Example 9. Control of a Chimeric Antigen Receptor for AML

A CAR is made using the anti-CD20 CAR cassette described in Budde 2013 (Budde et al. PLoS1, 2013 doi: 10.1371/journal.pone.0082742, which is hereby incorporated-by-reference in its entirety for all purposes), with the anti-CD133 mAb 293C3-SDIE is used for the extracellular element (Rothfelder et al., 2015, ash.confex.com/ash/2015/webprogram/Paper81121.html, which is incorporated by reference in its entirety for all purposes) replacing the anti-CD20 extracellular domain. The nucleic acid encoding the anti-CD133 CAR also can include the 3'-UTR from IL-2 engineered to remove the MIR186 micro-RNA sites or the 3'-UTR of IFN-γ engineered to remove the MIR125 micro-RNA sites, as described in Example 11. A construct encoding the anti-CD20 CAR cassette is engineered to replace the anti-CD20 extracellular domain with the anti-CD133 element, and the 3'-UTR of IL-2 engineered to remove the MIR186 microRNA sites or the 3'-UTR of IFN-γ engineered to remove the MIR125 micro-RNA sites, is also engineered into the construct. The anti-CD133 CAR with or without the 3'-UTRs are cloned into appropriate expression vectors.

This anti-CD133 CAR or one of the anti-CD133 RDE-CARs (3'UTR of IL-2 or 3'-UTR of IFN-γ) are transfected by routine methods into T-lymphocytes (Jurkat cells and/or primary human T-lymphocytes), and stable populations of T-lymphocytes are selected using appropriate antibiotics (or other selection schemes). T-lymphocyte populations with anti-anti-CD133 CAR, or the anti-CD133 RDE CAR (CD20$^-$/CD22$^-$/CD3$^+$) are activated by co-incubation with anti-CD3/CD28 beads with the addition of a glycolysis inducer (e.g., glucose).

Activated anti-CD133 CAR, or the anti-CD133 RDE CAR T-lymphocytes are co-cultured with CD133$^+$/CD3$^-$ AML target cells (e.g., U937, MV4-11, MOLM-14, HL-60 and/or KG1a) at anti-CD133 CAR, or the anti-CD133 RDE CAR T-lymphocyte:AML target ratios of 2:1, 5:1, and 10:1. The anti-CD133 CAR or the anti-CD133 RDE CAR T-lymphocytes and the AML cells are grown together for 48 hours. Cultures are washed, and then stained with anti-CD133 and anti-CD3 reagents, followed by counting of CD133$^+$ (AML target cells) and CD3$^+$ cells (anti-CD133 CAR, or the anti-CD133 RDE CAR T-lymphocytes). These measurements will identify the target cell killing rate (e.g., half-life) and the proliferation rate of the anti-CD133 CAR or the anti-CD133 RDE CAR T-lymphocytes at different levels of CAR expression.

Example 10. An Off-Switch for Controlling T-Cell Effector Activity

A Smart-ZAP 70 mutant can be made using the Y319F ZAP 70 mutant described in Wang et al., Cold Spring Harb Perspect Biol 2:a002279 (2010), which is incorporated by reference in its entirety for all purposes, and a Tet RNA control device described in Example 9. A nucleic acid encoding the Tet-RNA control device is operably linked to a nucleic acid encoding the Y319F ZAP 70 mutant, and this construct is in an appropriate expression vector.

T-cells with the anti-CD19 RDE CAR and anti-CD19 CAR constructs of Example 8 are used in this example. The RNA control device Y319F ZAP 70 is transfected by routine methods into T-cells with the anti-CD19 RDE CAR and anti-CD19 CAR constructs made following Example 8, and stable populations of T-cells are selected using appropriate antibiotics (or other selection schemes). T-cell populations with anti-CD19 RDE CARs (CD19$^-$/CD22$^-$/CD3$^+$) and T-cell populations with anti-CD19 CARs (CD19$^-$/CD22$^-$/CD3$^+$) are activated by co-incubation with anti-CD3/CD28 beads.

Activated RNA control device Y319F ZAP 70 and anti-CD19 RDE CAR T-cells are co-cultured with CD19$^+$/CD22$^+$/CD3$^-$ Ramos target cells at RDE CAR T-cell:Raji target ratios of 2:1, 5:1, and 10:1. The glycolysis activator glucose is added to the culture medium at concentrations in the range of 1.0 mM to 10 mM (1 mM, 2, mM, 3 mM, 4 mM, 5 mM, 7.5 mM and 10 mM). Tetracycline in the range of 2 µM to 2 mM (2 µM, 10 µM, 20 µM, 100 µM, 200 µM, 1 mM, and 2 mM) is added or not added to cells (have cell cultures ±Tetracycline). The RNA control device Y319F ZAP 70+RDE-CAR T-cells and the Raji cells are grown together for 48 hours. Cultures are washed, and then stained with anti-CD22 and anti-CD3 reagents, followed by counting of CD22$^+$ (Raji target cells) and CD3$^+$ cells (Smart CAR T-cells). These measurements will identify the target cell killing rate (e.g., half-life) and the proliferation rate of the RNA control device Y319F ZAP 70+RDE-CAR T-cells versus the RDE-CAR T-cells at different levels of Y319F ZAP 70 expression and different levels of RDE-XAP expression.

Example 11. Payload Delivery to DLBCL Using an Anti-CD19 CAR T-Cell

The anti-CD19 Smart CAR T-lymphocytes and anti-CD19 CAR T-cell lymphocytes of Example 6 are used in this example. These CAR T-lymphocytes are further engineered to include a construct encoding a PD-1 inhibitor under the control of the 3'-UTR of IL2 that has been modified by removal of the MIR186 sites. PD-1 inhibitors expressed by the construct include, for example, Pembrolizumab (Keytruda®), Nivolumab (Opdivo®), Atezolizumab (Tecentriq®), BMS-936558, Lambrolizumab, or polypeptides derived from these drugs. Other PD-1 inhibitors that may be expressed by the construct include those disclosed in Herbst et al., J Clin Oncol., 31:3000 (2013); Heery et al., J Clin Oncol., 32:5s, 3064 (2014); Powles et al., J Clin Oncol, 32:5s, 5011 (2014); Segal et al., J Clin Oncol., 32:5s, 3002 (2014), or U.S. Pat. Nos. 8,735,553; 8,617,546; 8,008,449; 8,741,295; 8,552,154; 8,354,509; 8,779,105; 7,563,869; 8,287,856; 8,927,697; 8,088,905; 7,595,048; 8,168,179; 6,808,710; 7,943,743; 8,246,955; and U.S. Pat. No. 8,217,149.

T-cell populations with anti-CD19 Smart CARs/PD-1 (CD19−/CD22−/CD3+) and T-cell populations with anti-CD19 CARs/PD-1 (CD19−/CD22−/CD3+) are activated by co-incubation with anti-CD3/CD28 beads. T-cells with anti-CD19 Smart CARs/PD-1 inhibitor or anti-CD19 CARs/PD-1 inhibitor were incubated with theophylline at 0, 75 and 250 µM for 72 hours. Activated anti-CD19 Smart CAR/PD-1 T-cells or anti-CD19 CAR/PD-1 T-cells were co-cultured with CD19+/CD22+/CD3− Raji target cells at Smart CAR/PD-1 T-cell:Raji target ratios of 2:1, 5:1, and 10:1. Ligand for the RNA control device, theophylline is maintained in the culture medium at concentrations of 0 µM, 75 µM, and 250 µM. The Smart-CAR/PD-1 T-cells or CAR/PD-1 T-cells and the Raji cells are grown together for 18 hours. Cultures are washed, and then stained with anti-CD22 and anti-CD3 reagents, followed by counting of CD22+ (Raji target cells) and CD3+ cells (Smart CAR T-cells). Samples from culture media are also taken at 6, 12 and 18 hours, and tested for PD-1 inhibitor by ELISA.

Example 12. Payload Delivery to AML Using an Anti-CD133 CAR T-Cell

A CAR is made using the anti-CD20 CAR cassette described in Budde 2013 (Budde et al. PLoS1, 2013 doi: 10.1371/journal.pone.0082742, which is hereby incorporated-by-reference in its entirety for all purposes), with the anti-CD133 mAb 293C3-SDIE is used for the extracellular element (Rothfelder et al., 2015, ash.confex.com/ash/2015/webprogram/Paper81121.html, which is incorporated by reference in its entirety for all purposes) replacing the anti-CD20 extracellular domain. The anti-CD133 CAR also can encode the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the anti-CD20 CAR cassette is engineered to replace the anti-CD20 extracellular domain with the anti-CD133 element, and optionally the RNA control device is also engineered into the cassette. The anti-CD133 CAR with or without the RNA control device are cloned into appropriate expression vectors.

These anti-CD133 CAR and anti-CD133 Smart CAR constructs are transfected by routine methods into T-lymphocytes (Jurkat cells and/or primary human T-lymphocytes), and stable populations of T-lymphocytes are selected using appropriate antibiotics (or other selection schemes).

These CAR T-lymphocytes are further engineered to include a construct encoding a PD-1 inhibitor under the control of the RDE from the 3'-UTR of IL2 that has been modified by removal of a MIR186 site. PD-1 inhibitors expressed by the construct include, for example, Pembrolizumab (Keytruda®), Nivolumab (Opdivo®), Atezolizumab (Tecentriq®), BMS-936558, Lambrolizumab, or polypeptides derived from these drugs. Other PD-1 inhibitors that may be expressed by the construct include those disclosed in Herbst et al., J Clin Oncol., 31:3000 (2013); Heery et al., J Clin Oncol., 32:5s, 3064 (2014); Powles et al., J Clin Oncol, 32:5s, 5011 (2014); Segal et al., J Clin Oncol., 32:5s, 3002 (2014), or U.S. Pat. Nos. 8,735,553; 8,617,546; 8,008,449; 8,741,295; 8,552,154; 8,354,509; 8,779,105; 7,563,869; 8,287,856; 8,927,697; 8,088,905; 7,595,048; 8,168,179; 6,808,710; 7,943,743; 8,246,955; and U.S. Pat. No. 8,217,149.

T-lymphocyte populations with anti-CD133 CAR/PD-1 inhibitor or anti-CD133 Smart CAR/PD-1 inhibitor (CD20$^-$/CD22$^-$/CD3$^+$) are activated by co-incubation with anti-CD3/CD28 beads.

Activated anti-CD133 CAR/PD-1 inhibitor or anti-CD133 Smart CAR/PD-1 inhibitor T-lymphocytes are co-cultured with CD133$^+$/CD3$^-$ AML target cells (e.g., U937, MV4-11, MOLM-14, HL-60 and/or KG1a) at anti-CD133 CAR and/or anti-CD133 Smart CAR T-lymphocyte:AML target ratios of 2:1, 5:1, and 10:1. Ligand for the RNA control device, theophylline, is added to the culture medium at concentrations in the range of 500 µM to 1 mM (lower or greater concentrations can be used to titrate Smart-CAR activity to the desired level). The anti-CD133 CAR/PD-1 inhibitor and/or anti-CD133 Smart CAR/PD-1 inhibitor T-lymphocytes and the AML cells are grown together for 48 hours. Cultures are washed, and then stained with anti-CD133 and anti-CD3 reagents, followed by counting of CD133$^+$ (AML target cells) and CD3$^+$ cells (anti-CD133 CAR, anti-CD133 DE-CAR, anti-CD133 Smart CAR, and/or the anti-CD133 DE-Smart CAR T-lymphocytes). These measurements will identify the target cell killing rate (e.g., half-life) and the proliferation rate of the anti-CD133 CAR/PD-1 inhibitor and/or anti-CD133 Smart CAR/PD-1 inhibitor T-lymphocytes at different levels of CAR expression. Samples from culture media are also taken at 12, 24, 26 and 48 hours, and tested for PD-1 inhibitor by ELISA.

Example 13. Constructs for Expressing a CAR and a Second Transgene

Constructs were made using an anti-CD19 CAR cassette as described in WO 2012/079000, which is hereby incorporated-by-reference in its entirety for all purposes), and a GFP-RDE2 (3'-UTR from IL-2) insert. These two inserts/cassettes were placed on different lenti virus constructs or placed in the same bicistronic lenti virus construct. In the bicistronic construct, the inserts with the anti-CD19 CAR and the insert with the GFP-RDE are transcribed in opposite directions, and the control regions for each are located in between the two insert/cassettes. The control region for the GFP-RDE2 insert in the single construct lenti vector was MND (a synthetic promoter that contains the U3 region of a modified MoMuLV LTR with myeloproliferative sarcoma virus enhancer) which is described in Li et al., J. Neurosci. Methods 189:56-64 (2010), which is incorporated by reference in its entirety for all purposes. The control region for the GFP-RDE2 insert in the bicistronic lenti vector was MinP and the RDE used the endogenous 3'-UTR of IL-2. The control region of the anti-CD19 CAR cassette in both constructs was also MND. CD4+ T-cells were either doubly transduced with the individual anti-CD19 CAR lenti construct and the GFP-RDE2 lenti construct, or were singly transduced with the bicistronic construct with both the anti-CD19 CAR lenti construct and the GFP-RDE2 lenti construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The doubly transduced T-cells showed an increase in fluorescence when cultured with Raji target cells (activate CAR) of 19.5% to 42.5% (about 2 fold), and increase in fluorescence when cultured with CD3/CD28 beads (activate TCR) of 19.5% to 34.9% (about 1.8 fold). The doubly transformed T-cells showed a change in activated cells in the population when cultured with Raji cells of 0.9% to 56.9%, and when cultured with CD3/CD28 beads of 0.9% to 92.5%.

The singly transduced T-cells showed a change in activated cells in the population when cultured with Raji cells of 3.6% to 5.8%, and when cultured with CD3/CD28 beads of 3.6% to 6.6%.

Example 14. An RDE Construct for Expressing a Second Transgene

Constructs were made using an anti-CD19 CAR cassette as described in WO 2012/079000, which is hereby incorporated-by-reference in its entirety for all purposes), and a GFP-RDE1 (3'-UTR from IFNg) insert. These two inserts/cassettes were placed in the same lenti virus construct. The anti-CD19 CAR cassette and the insert with the GFP-RDE are transcribed in opposite directions, and the control regions for each are located in between the two insert/cassettes. The control region for the GFP-RDE insert was MinP and the RDE was the endogenous 3'-UTR of IFNg. The control region of the anti-CD19 CAR cassette was MND (as described above). CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The transduced T-cells showed an increase in fluorescence when cultured with Raji target cells (activate CAR) of 1.0% to 6.5% (about 6.5 fold), and increase in fluorescence when cultured with CD3/CD28 beads (activate TCR) of 1.0% to 4.4% (about 4.4 fold). The transformed T-cells showed a change in activated cells in the population when cultured with Raji cells of 0.9% to 84.8%, and when cultured with CD3/CD28 beads of 0.9% to 90.8%.

Example 15. A Modified RDE2 Construct for Expressing a Second Transgene

Constructs were made using an anti-CD19 CAR cassette as described in Examples 11 and 12, and a GFP-RDE2.1 (IL-2 RDE) insert. The RDE2.1 was modified to remove the MIR186 microRNA sites, altering nucleotides from the 3'-UTR of IL-2 which was used as RDE2.

These two inserts/cassettes were placed in the same lenti virus construct. The anti-CD19 CAR cassette and the insert with the GFP-RDE are transcribed in opposite directions, and the control regions for each are located in between the two insert/cassettes. The control region for the GFP-RDE insert was a MinP. The control region of the anti-CD19 CAR cassette in was MND (as described above). CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The transduced T-cells showed a change in activated cells in the population when cultured with Raji cells of 3.9% to 12.1%, and when cultured with CD3/CD28 beads of 3.9% to 11.1%.

Example 16. An RDE Construct for Expressing a Luciferase Transgene

Constructs were made using an anti-CD19 CAR cassette as described in WO 2012/079000, which is hereby incorporated-by-reference in its entirety for all purposes), and a Luciferase-RDE1 (3'-UTR of IFNg, Gold1) insert or a Luciferase-3'-UTR (a 3'-UTR that does not confer differential transgene translation in response to metabolic state of the cell, 3'-UTR). The anti-CD19 CAR cassette and the insert with the luciferase-RDE1 are transcribed in opposite directions, and the control regions for each are located in between the two insert/cassettes. The control region for the Luciferase-RDE1 insert and Luciferase-3'-UTR were either a MinP promoter or an NFAT promoter having the sequences of:

(MinP)
SEQ ID NO: 31
TAGAGGGTATATAATGGAAGCTCGACTTCCAG (NFAT)
SEQ ID NO: 32
GGAGGAAAAACTGTTTCATACAGAAGGCGTGGAGGAAAAACTGTTTCATA

CAGAAGGCGTGGAGGAAAAACTGTTTCATACAGAAGGCGTAGATCTAGAC

TCTAGAGGGTATATAATGGAAGCTCGAATTC

The control region of the anti-CD19 CAR cassette was the MND promoter. CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and luciferase expression in the T cells.

Figure 16:
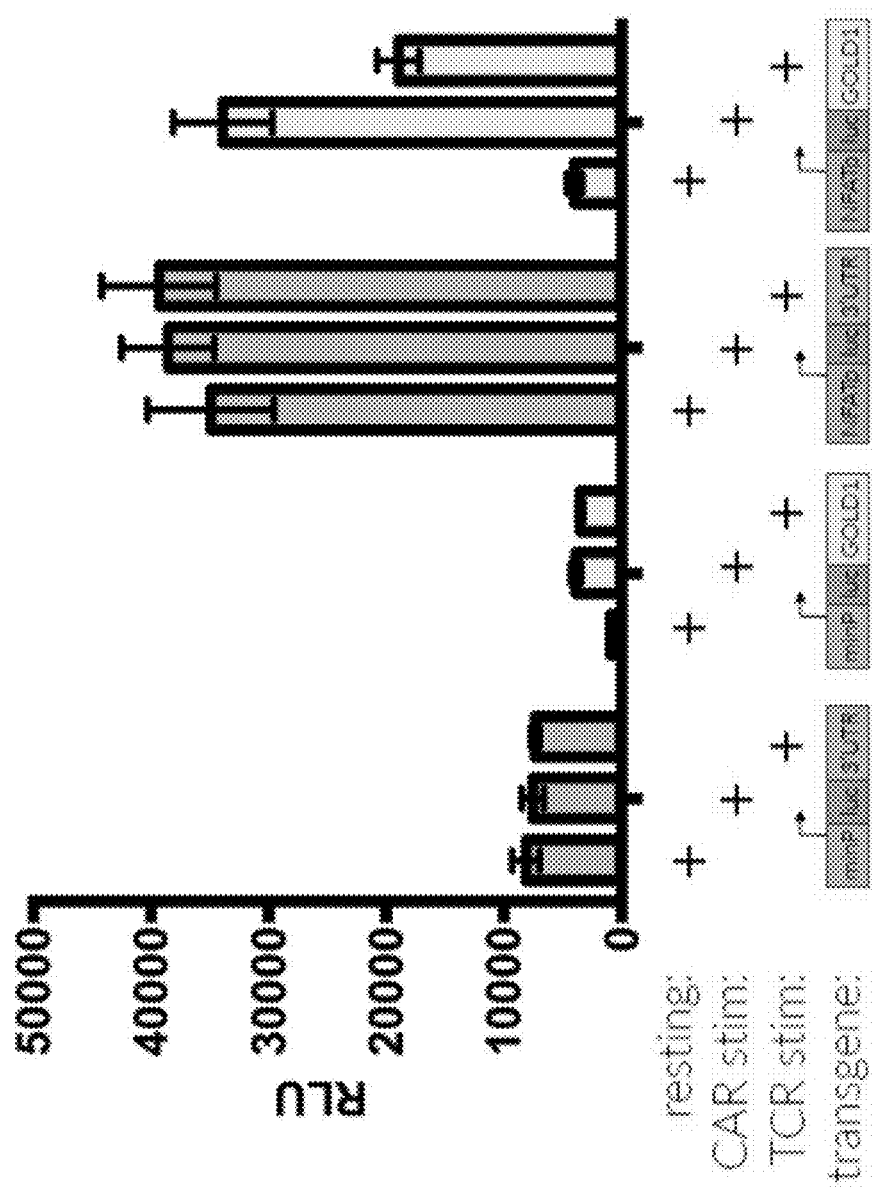
FIG. 16 shows a graph for the bioluminescence from T-cells with luciferase controlled by an RDE following activation of the T-cell by Raji target cells (activate CAR) or by CD3/CD28 beads (activate TCR) as compared to bioluminescence of T-cells at resting.

FIG. 16 shows that the transduced T-cells had an increase in bioluminescence when cultured with Raji target cells (activate CAR) or when cultured with CD3/CD28 beads (activate TCR) as compared to bioluminescence of T-cells at resting. The T-cells with a NFAT promoter and the 3'-UTR of IFNg (Gold1) showed a larger on-off response from CAR stimulation versus TCR stimulation. Under all conditions, T-cells with Gold1 had lower amounts of bioluminescence than T-cells under the same conditions (and same promoter) with Luciferase that was not controlled by the 3'UTR of IFNg (3'-UTR).

Example 17. Comparison of RDEs Controlling Luciferase

Constructs were made using an anti-CD19 CAR cassette as described in WO 2012/079000, which is hereby incorporated-by-reference in its entirety for all purposes), and a Luciferase-RDE1 (3' UTR of IFNg, Gold1) insert, a Luciferase-RDE2 (3'-UTR of IL-2, Gold2) insert, a Luciferase-RDE3 (3'-UTR of IL-2 modified as described above to remove the mir186 sites, Gold3), or a Luciferase-3'-UTR (a 3'-UTR that does not confer differential transgene translation in response to metabolic state of the cell, 3'-UTR). Combinations of these inserts/cassettes shown in FIG. 17 were placed in the similar lenti virus constructs. The anti-CD19 CAR cassette and the insert with the luciferase-RDE are transcribed in opposite directions, and the control regions for each are located in between the two insert/cassettes. The control region for the Luciferase-RDE insert and Luciferase-3'-UTR were either a MinP promoter or an NFAT promoter. The control region of the anti-CD19 CAR cassette was the MND promoter, and CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set CD19+ Raji B cells were incubated with the transduced T cells for 24 h. At 24 h, the T cells were stained for CD25 and CD69, which are activation markers, and subject to flow cytometry to measure these markers and luciferase expression in the T cells.

Figure 17:
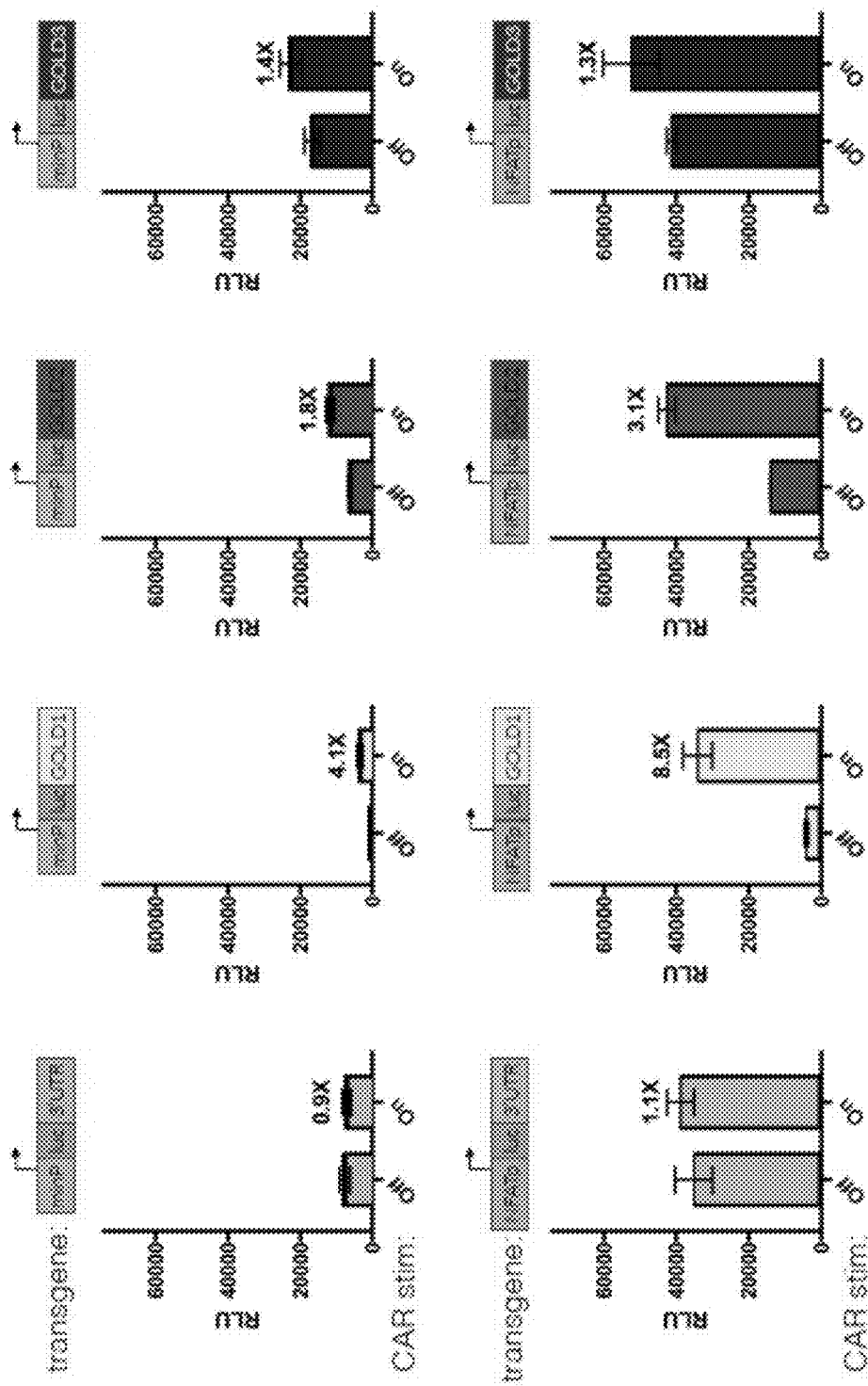
FIG. 17 shows a graph for bioluminescence from T-cells with luciferase controlled by the RDEs Gold1, Gold2, or Gold3 following activation of the T-cell by Raji target cells (activate CAR) as compared to bioluminescence of T-cells at resting.

FIG. 17 shows that the transduced T-cells had an increase in bioluminescence when cultured with Raji target cells (activate CAR) as compared to bioluminescence of T-cells at resting for constructs with RDE1 (Gold1), RDE2 (Gold2), or RDE3 (Gold3). The T-cells with a NFAT promoter and the RDE1 showed a larger on-off response than T-cells with a MinP promoter and the corresponding RDE. Under all conditions, T-cells with an RDE controlling luciferase had lower amounts of bioluminescence than T-cells with luciferase cassettes that were not controlled by an RDE. Combined with the MinP promoter, RDE1 gave a 4.1-fold increase in bioluminescence with CAR stimulation, RDE2 gave a 1.8-fold increase in bioluminescence, and RDE3 gave a 1.4-fold increase. Combined with the NFAT promoter, RDE1 gave a 8.5-fold increase in bioluminescence with CAR stimulation, RDE2 gave a 3.1-fold increase in bioluminescence, and RDE3 gave a 1.3-fold increase. With either promoter, the RDE3 construct gave the highest amount of bioluminescence, the RDE1 construct gave the lowest amount of bioluminescence, and the RDE2 construct gave an amount of bioluminescence between RDE3 and RDE1.

Example 18. An RDE Construct for Expressing IL-12

Constructs were made using an anti-CD19 CAR cassette as described in WO 2012/079000, which is hereby incorporated-by-reference in its entirety for all purposes), and an IL-12-RDE1 (3'-UTR of IFNg) insert or an IL-12 3'-UTR (a 3'-UTR that does not confer differential transgene translation in response to metabolic state of the cell). The anti-CD19 CAR cassette and the insert with the IL-12-RDE1 are transcribed in opposite directions, and the control regions for each are located in between the two insert/cassettes. The control region for the IL-12-RDE1 insert and IL-12 3'-UTR were either a minP promoter or an NFAT promoter. The control region of the anti-CD19 CAR cassette was the MND promoter. CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set, CD19+ Raji B cells were incubated with the transduced T cells for 24 h. At 24 h, the T cells were stained for CD25 and CD69, which are activation markers, and subject to flow cytometry to measure these markers. IL-12 expression in the T cells was measured by ELISA.

Figure 18:
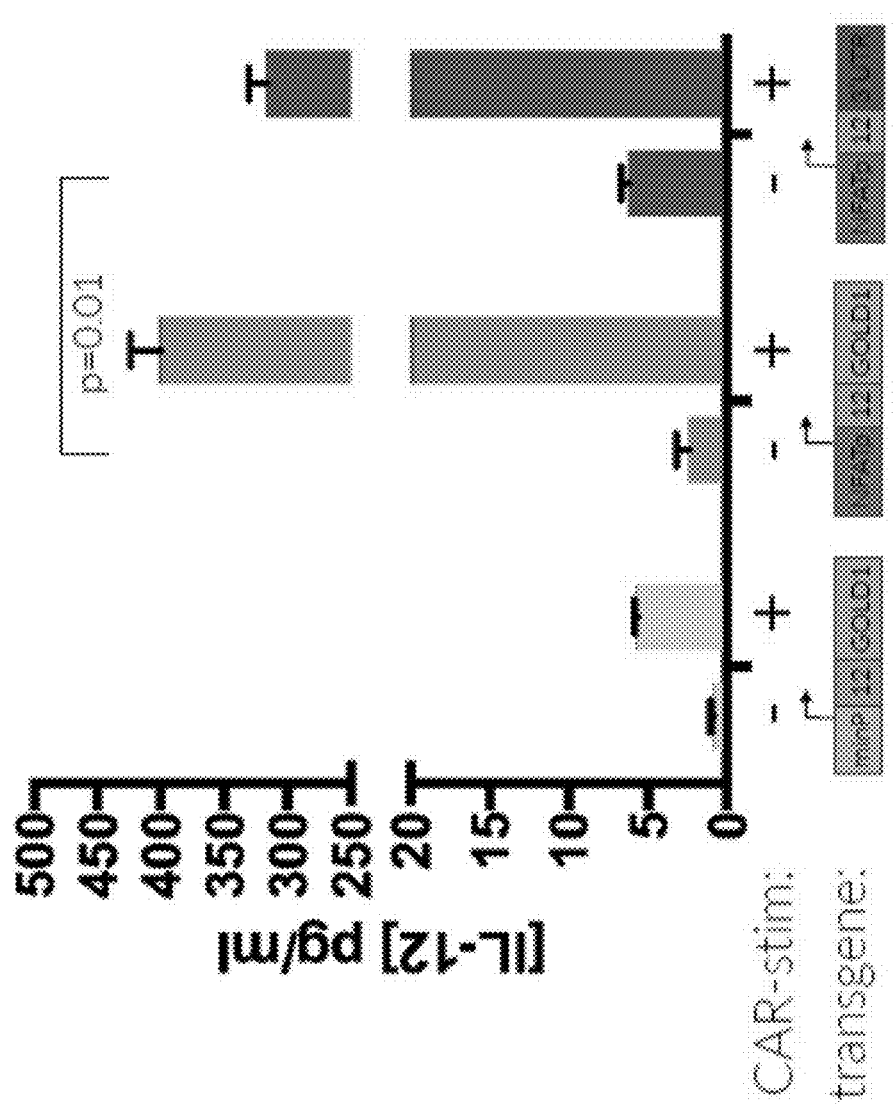
FIG. 18 shows a graph for the IL-12 expression from T-cells with IL-12 expression controlled by an RDE following activation of the T-cell by Raji target cells (activate CAR) as compared to IL-12 expression of T-cells at resting.

FIG. 18 shows that the transduced T-cells had an increase in IL-12 expression when cultured with Raji target cells (activate CAR) as compared to IL-12 expression of T-cells at resting using constructs controlled by the MinP promoter or NFAT promoter. T-cells with the NFAT promoter and RDE1 (Gold1) showed a 168-fold change in IL-12 expression form resting to CAR stimulation. T-cells with the NFAT promoter and a 3'-UTR (not responsive to CAR stimulation, 3'-UTR) showed a 50-fold change in expression, and a minP promoter with RDE1 (Gold1) showed a 6.3 fold change in expression.

Disclosure of Python Code for Calculating Time Dependent Effector Function

```
import numpy as np
from math import exp
# E is effector activity, i.e. number of cytokines, perforins,
    etc. that are produced
# nR=number of receptors
# nT=number of targets
# nRT=number of receptors and targets bound
# constants required for activation/decay calculations
c_act=1 # c_act=activation constant
c_inh=1 # c_inh=inhibition constant
c_eng=1 # c_eng=energy constant, a term available for
    metabolic function, currently not included
e_avail=1 # e_avail=energy available, a term available for
    metabolic function, currently not included
k1=1 # rxn constant for [r][t]→[rt]
k_1=1 # rxn constant for [rt]→[r][t]
k_car_to=0 # rate of car turnover
# constants required for ribozyme portion of model
k_rbz=1 # rxn constant for ribozyme
k_rbz_off=0.1 # rxn constant for ribozyme cleavage when in
    presence of
k_translation=1 # time/rate constant associated with trans-
    lation of
def activation(y, t): # code for activation
    E, nRT, nR, nT=y
    dEdt=nRT*c_act−c_inh*E*t*nRT #t included in this term
        to simulate antigen dependent exhaustion maybe move
        to Qm
    dnRTdt=k1*nR*nT−k_1*nRT
    dnRdt=k_1*nRT−k1*nR*nT−nR*k_car_to
    dnTdt=k_1*nRT−k1*nR*nT
    return dEdt, dnRTdt, dnRdt, dnTdt
def decay(y, t): #code for natural decay via turnover
    E, nRT, nR, nT=y
    dEdt=nRT*c_act−c_inh*E*t*nRT
    dnRTdt=k1*nR*nT−k_1*nRT
    dnRdt=k_1*nRT−k1*nR*nT−nR*k_car_to
    dnTdt=k_1*nRT−k1*nR*nT
    return dEdt, dnRTdt, dnRdt, dnTdt
# t0=npinispace(0, 1, 11) # drug dosing from 0→1
t1=np.linspace(0, 1, 11) # activation from 1→2
t2=np.linspace(1, 5, 31) # decay from 1→5
from scipy.integrate import odeint
y1=[0.01, 0.01, 5, 10]
sol1=odeint(activation, y1, t1)
y2=[sol1[10,0],sol1[10,1],sol1[10,2], sol1[10,3]]
sol2=odeint(decay, y2, t2)
import matplotlib.pyplot as plt
plt.plot(t1, sol1[:, 0], color='k', marker='o', label='E')
plt.plot(t1, sol1[:, 1], color='k', marker='+', label='nRT')
plt.plot(t1, sol1[:, 2], color='k', marker='*', label='nR')
plt.plot(t1, sol1[:, 3], color='k', marker='s', label='nT')
plt.plot(t2, sol2[:, 0], color='k', marker='o')
plt.plot(t2, sol2[:, 1], color='k', marker='+')
plt.plot(t2, sol2[:, 2], color='k', marker='*')
plt.plot(t2, sol2[:, 3], color='k', marker='s')
plt.legend(loc='best')
plt.xlabel('t')
plt.grid( )
plt. show( )
```

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for expressing a transgene, comprising the steps of:
   (a) obtaining a primary T-cell comprising a chimeric antigen receptor, and a heterologous nucleic acid comprising a polynucleotide encoding the transgene that is operably linked to a polynucleotide encoding a RNA destabilizing element (RDE), wherein the RDE is an AU rich element, wherein the heterologous nucleic acid is transcribed to make a transcript encoding the transgene operably linked to the RDE, wherein an RDE binding protein binds to the RDE and regulates expression of the transgene;
   (b) binding the primary T-cell to a target ligand for the chimeric antigen receptor at a target site in a subject wherein binding of the target ligand by the chimeric antigen receptor activates the primary T-cell, wherein activation of the primary T-cell changes a metabolic state of the primary T-cell and this changes binding of the RDE by the RDE binding protein; and
   (c) expressing the transgene wherein the amount of polypeptide made from the transgene is increased after activation of the cell by the chimeric antigen receptor.

2. The method of claim 1, wherein the transgene encodes a cytokine, a FasL, an antibody, a growth factor, a chemokine, an enzyme that cleaves a polypeptide or a polysaccharide, a granzyme, a perforin, a checkpoint inhibitor, a chimeric antigen receptor or a membrane bound receptor.

3. The method of claim 2, wherein the transgene encodes a cytokine.

4. The method of claim 3, wherein the cytokine is an IL-12.

5. The method of claim 1, wherein the primary T-cell displays an amount of 10 to 100,000 chimeric antigen receptors per primary T-cell.

6. The method of claim 5, wherein the primary T-cell displays 100 to 5,000 chimeric antigen receptors.

7. The method of claim 1, wherein the target cell is an AML, cell.

8. The method of claim 7, wherein the target ligand is a CD43.

9. The method of claim 8, further comprising the step of killing the AML cell.

10. The method of claim 1, wherein the RDE in the transcript is bound by a glycolytic enzyme selected from the group consisting of a glyceraldehyde phosphate dehydrogenase, an enolase, a phosphoglycerate kinase, a triose phosphate isomerase, an aldolase A or a phosphoglycerate mutase.

11. The method of claim 10, wherein the glycolytic enzyme is a glyceraldehyde phosphate dehydrogenase.

12. The method of claim 11, wherein the activation of the primary T-cell increases a glycolysis wherein the activation of the glycolysis results in a reduction of binding of the RDE in the transcript by the glyceraldehyde phosphate dehydrogenase.

13. The method of claim 12, further comprising the step of binding a second RDE binding protein to the RDE in the transcript.

14. The method of claim 13, wherein binding of the second RDE binding protein increases a half-life of the transcript, or a translation rate of the transcript.

\* \* \* \* \*

SEQUENCE LISTING

<160> NUMBER OF SEQ ID NOS: 32

<210> SEQ ID NO 1
<211> LENGTH: 98
<212> TYPE: RNA
<213> ORGANISM: Artificial Sequence
<220> FEATURE:
<223> OTHER INFORMATION: Tetracycline RNA control device

<400> SEQUENCE: 1
gcgcguccug gauuaaaaca uaccagauuu cgaucuggag aggugaagaa uacgaccacc     60
uaauccagcu gaugaguccc aaauaggacg aaacgcgc                            98

<210> SEQ ID NO 2
<211> LENGTH: 110
<212> TYPE: RNA
<213> ORGANISM: Artificial Sequence
<220> FEATURE:
<223> OTHER INFORMATION: New tetracycline RNA control device
<220> FEATURE:
<221> NAME/KEY: misc_feature
<222> LOCATION: (16)..(20)
<223> OTHER INFORMATION: n is a, c, g, or u
<220> FEATURE:
<221> NAME/KEY: misc_feature
<222> LOCATION: (70)..(74)
<223> OTHER INFORMATION: n is a, c, g, or u

<400> SEQUENCE: 2
gcgcguccug gauucnnnnn uaaaacauac cagauuucgg ucuggagagg ugaagaauac     60
gaccaccuan nnnnauccag cugaugaguc ccaaauagga cgaaacgcgc               110

<210> SEQ ID NO 3
<211> LENGTH: 31
<212> TYPE: RNA
<213> ORGANISM: Artificial Sequence
<220> FEATURE:
<223> OTHER INFORMATION: Aptamer for 6R-folinic acid

<400> SEQUENCE: 3
acgucgacuu auauugcaug guucgugacg u                                   31

<210> SEQ ID NO 4
<211> LENGTH: 37
<212> TYPE: RNA
<213> ORGANISM: Artificial Sequence
<220> FEATURE:
<223> OTHER INFORMATION: Alternative apatamer for 6R-folinic acid

<400> SEQUENCE: 4
cgaaccggcc uuauauugca uggugcguug cggcucg                             37

<210> SEQ ID NO 5
<211> LENGTH: 66
<212> TYPE: RNA
<213> ORGANISM: Artificial Sequence
<220> FEATURE:
<223> OTHER INFORMATION: New aptamer for 6R-folinic acid

<400> SEQUENCE: 5
gcugucaccg gaugcuuggu acguuauauu cagccgguc ugaugagucc gugaggacga     60
aacagc                                                               66

<210> SEQ ID NO 6
<211> LENGTH: 76

```
<212> TYPE: RNA
<213> ORGANISM: Artificial Sequence
<220> FEATURE:
<223> OTHER INFORMATION: Aptamer for 6R-folinic acid

<400> SEQUENCE: 6
gcugucaccg gauggcguug cgugguacgu uauauuccgg ccaucugguc ugaugaguccc      60 gugaggacga aacagc                                                     76

<210> SEQ ID NO 7
<211> LENGTH: 67
<212> TYPE: RNA
<213> ORGANISM: Artificial Sequence
<220> FEATURE:
<223> OTHER INFORMATION: Aptamer for 6R-folinic acid

<400> SEQUENCE: 7
gcugucaccg gauugcgugg uacguuauau uccguccggu cugaugaguc cgugaggacg      60
aaacagc                                                               67

<210> SEQ ID NO 8
<211> LENGTH: 5
<212> TYPE: RNA
<213> ORGANISM: Artificial Sequence
<220> FEATURE:
<223> OTHER INFORMATION: AU repeat element

<400> SEQUENCE: 8 auuua                                                                  5

<210> SEQ ID NO 9
<211> LENGTH: 13
<212> TYPE: RNA
<213> ORGANISM: Artificial Sequence
<220> FEATURE:
<223> OTHER INFORMATION: AU rich element

<400> SEQUENCE: 9
auuuauuuau uua                                                         13

<210> SEQ ID NO 10
<211> LENGTH: 5
<212> TYPE: RNA
<213> ORGANISM: Artificial Sequence
<220> FEATURE:
<223> OTHER INFORMATION: GU rich repeat element

<400> SEQUENCE: 10 uuguu                                                                  5

<210> SEQ ID NO 11
<211> LENGTH: 7
<212> TYPE: RNA
<213> ORGANISM: Artificial Sequence
<220> FEATURE:
<223> OTHER INFORMATION: GU rich repeat element

<400> SEQUENCE: 11 uggggau                                                                7

<210> SEQ ID NO 12
<211> LENGTH: 5
<212> TYPE: RNA
<213> ORGANISM: Artificial Sequence
<220> FEATURE:
```

```
<223> OTHER INFORMATION: U rich repeat element

<400> SEQUENCE: 12 guuug                                                                 5

<210> SEQ ID NO 13
<211> LENGTH: 7
<212> TYPE: RNA
<213> ORGANISM: Artificial Sequence
<220> FEATURE:
<223> OTHER INFORMATION: GU rich element

<400> SEQUENCE: 13 uuuguuu                                                               7

<210> SEQ ID NO 14
<211> LENGTH: 9
<212> TYPE: RNA
<213> ORGANISM: Artificial Sequence
<220> FEATURE:
<223> OTHER INFORMATION: U rich element
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (5)..(6)
<223> OTHER INFORMATION: n is a, c, g, or u

<400> SEQUENCE: 14 nnuunnuuu                                                             9

<210> SEQ ID NO 15
<211> LENGTH: 7
<212> TYPE: RNA
<213> ORGANISM: Artificial Sequence
<220> FEATURE:
<223> OTHER INFORMATION: U rich element

<400> SEQUENCE: 15 uuuauuu                                                               7

<210> SEQ ID NO 16
<211> LENGTH: 7
<212> TYPE: RNA
<213> ORGANISM: Artificial Sequence
<220> FEATURE:
<223> OTHER INFORMATION: U rich element

<400> SEQUENCE: 16 uuuuuuu                                                               7

<210> SEQ ID NO 17
<211> LENGTH: 5
<212> TYPE: RNA
<213> ORGANISM: Artificial Sequence
<220> FEATURE:
<223> OTHER INFORMATION: RDE element

<400> SEQUENCE: 17 uuaga                                                                 5

<210> SEQ ID NO 18
<211> LENGTH: 5
<212> TYPE: RNA
<213> ORGANISM: Artificial Sequence
```

```
<220> FEATURE:
<223> OTHER INFORMATION: RDE element

<400> SEQUENCE: 18 aguuu                                                                    5

<210> SEQ ID NO 19
<211> LENGTH: 9
<212> TYPE: RNA
<213> ORGANISM: Artificial Sequence
<220> FEATURE:
<223> OTHER INFORMATION: RDE element

<400> SEQUENCE: 19 uuauuuauu                                                                9

<210> SEQ ID NO 20
<211> LENGTH: 4
<212> TYPE: RNA
<213> ORGANISM: Artificial Sequence
<220> FEATURE:
<223> OTHER INFORMATION: RDE element

<400> SEQUENCE: 20 uuga                                                                     4

<210> SEQ ID NO 21
<211> LENGTH: 7
<212> TYPE: RNA
<213> ORGANISM: Artificial Sequence
<220> FEATURE:
<223> OTHER INFORMATION: RDE element

<400> SEQUENCE: 21 ugggggau                                                                 7

<210> SEQ ID NO 22
<211> LENGTH: 9
<212> TYPE: RNA
<213> ORGANISM: Artificial Sequence
<220> FEATURE:
<223> OTHER INFORMATION: RDE element

<400> SEQUENCE: 22 cugcugcug                                                                9

<210> SEQ ID NO 23
<211> LENGTH: 5
<212> TYPE: RNA
<213> ORGANISM: Artificial Sequence
<220> FEATURE:
<223> OTHER INFORMATION: RDE element

<400> SEQUENCE: 23 auuga                                                                    5

<210> SEQ ID NO 24
<211> LENGTH: 18
<212> TYPE: PRT
<213> ORGANISM: Thoseaasigna virus 2A

<400> SEQUENCE: 24

Glu Gly Arg Gly Ser Leu Leu Thr Cys Gly Asp Val Glu Glu Asn Pro
1               5                   10                  15

Gly Pro
```

<210> SEQ ID NO 25
<211> LENGTH: 19
<212> TYPE: PRT
<213> ORGANISM: Porcine teschovirus-1

<400> SEQUENCE: 25

```
Ala Thr Asn Phe Ser Leu Leu Lys Gln Ala Gly Asp Val Glu Glu Asn
1               5                   10                  15

Pro Gly Pro
```

<210> SEQ ID NO 26
<211> LENGTH: 20
<212> TYPE: PRT
<213> ORGANISM: Equine rhinitis A virus

<400> SEQUENCE: 26

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 27
<211> LENGTH: 22
<212> TYPE: PRT
<213> ORGANISM: foot and mouth disease virus

<400> SEQUENCE: 27

```
Val Lys Gln Thr Leu Asn Phe Asp Leu Leu Lys Leu Ala Gly Asp Val
1               5                   10                  15

Glu Ser Asn Pro Gly Pro
            20
```

<210> SEQ ID NO 28
<211> LENGTH: 282
<212> TYPE: DNA
<213> ORGANISM: Homo sapiens

<400> SEQUENCE: 28

```
taattaagtg cttcccactt aaaacatatc aggccttcta tttatttaaa tatttaaatt      60
ttatatttat tgttgaatgt atggtttgct acctattgta actattattc ttaatcttaa     120
aactataaat atggatcttt tatgattctt tttgtaagcc ctaggggctc taaaatggtt     180
tcacttattt atcccaaaat atttattatt atgttgaatg ttaaatatag tatctatgta     240
gattggttag taaaactatt taataaattt gataaatata aa                        282
```

<210> SEQ ID NO 29
<211> LENGTH: 282
<212> TYPE: DNA
<213> ORGANISM: Homo sapiens

<400> SEQUENCE: 29

```
taattaagtg cttcccactt aaaacatatc aggccttcta tttatttaaa tatttaaatt      60
ttatatttat tgttgaatgt atggtttgct acctattgta actattattc ttaatcttaa     120
aactataaat atggatcttt tatgattgaa tttgtaagcc ctaggggctc taaaatggtt     180
tcacttattt atcccaaaat atttattatt atgttgaatg ttaaatatag tatctatgta     240
gattggttag taaaactatt taataaattt gataaatata aa                        282
```

```
<210> SEQ ID NO 30
<211> LENGTH: 585
<212> TYPE: DNA
<213> ORGANISM: Homo sapiens

<400> SEQUENCE: 30
tggttgtcct gcctgcaata tttgaatttt aaatctaaat ctatttatta atatttaaca      60
ttatttatat ggggaatata tttttagact catcaatcaa ataagtattt ataatagcaa     120
cttttgtgta atgaaaatga atatctatta atatatgtat tatttataat tcctatatcc     180
tgtgactgtc tcacttaatc ctttgttttc tgactaatta ggcaaggcta tgtgattaca     240
aggctttatc tcaggggcca actaggcagc caacctaagc aagatcccat gggttgtgtg     300
tttatttcac ttgatgatac aatgaacact tataagtgaa gtgatactat ccagttactg     360
ccggtttgaa aatatgcctg caatctgagc cagtgcttta atggcatgtc agacagaact     420
tgaatgtgtc aggtgaccct gatgaaaaca tagcatctca ggagatttca tgcctggtgc     480
ttccaaatat tgttgacaac tgtgactgta cccaaatgga aagtaactca tttgttaaaa     540
ttatcaatat ctaatatata tgaataaagt gtaagttcac aacta                     585

<210> SEQ ID NO 31
<211> LENGTH: 32
<212> TYPE: DNA
<213> ORGANISM: Artificial Sequence
<220> FEATURE:
<223> OTHER INFORMATION: MinP promoter

<400> SEQUENCE: 31
tagagggtat ataatggaag ctcgacttcc ag                                    32

<210> SEQ ID NO 32
<211> LENGTH: 131
<212> TYPE: DNA
<213> ORGANISM: Artificial Sequence
<220> FEATURE:
<223> OTHER INFORMATION: NFAT promoter

<400> SEQUENCE: 32
ggaggaaaaa ctgtttcata cagaaggcgt ggaggaaaaa ctgtttcata cagaaggcgt      60
ggaggaaaaa ctgtttcata cagaaggcgt agatctagac tctagagggt atataatgga     120
agctcgaatt c                                                          131
```